United States Patent
Liu et al.

(10) Patent No.: US 10,874,610 B2
(45) Date of Patent: Dec. 29, 2020

(54) EXTRACELLULAR VESICLE-BASED DIAGNOSTICS AND ENGINEERED EXOSOMES FOR TARGETED THERAPEUTICS AGAINST CANCER

(71) Applicants: Northwestern University, Evanston, IL (US); Case Western Reserve University, Cleveland, OH (US)

(72) Inventors: Huiping Liu, Chicago, IL (US); Erika K. Ramos, Chicago, IL (US); Nurmaa K. Dashzeveg, Chicago, IL (US); Golam Kibria, Chicago, IL (US)

(73) Assignees: Northwestern University, Evanston, IL (US); Case Western Reserve University, Cleveland, OH (US)

( * ) Notice: Subject to any disclaimer, the term of this patent is extended or adjusted under 35 U.S.C. 154(b) by 169 days.

(21) Appl. No.: 15/788,709

(22) Filed: Oct. 19, 2017

(65) Prior Publication Data

US 2018/0104187 A1     Apr. 19, 2018

Related U.S. Application Data

(60) Provisional application No. 62/409,921, filed on Oct. 19, 2016.

(51) Int. Cl.

| | | |
|---|---|---|
| *A61K 9/127* | (2006.01) | |
| *G01N 33/574* | (2006.01) | |
| *A61K 31/7105* | (2006.01) | |
| *C07K 14/705* | (2006.01) | |
| *A61K 38/00* | (2006.01) | |

(52) U.S. Cl.
CPC ............ *A61K 9/127* (2013.01); *A61K 9/1277* (2013.01); *A61K 31/7105* (2013.01); *C07K 14/70503* (2013.01); *C07K 14/70596* (2013.01); *G01N 33/57415* (2013.01); *G01N 33/57484* (2013.01); *G01N 33/57488* (2013.01); *A61K 38/00* (2013.01); *C07K 2319/03* (2013.01); *C07K 2319/70* (2013.01)

(58) Field of Classification Search
CPC ...................................................... A61K 9/127
USPC ......................................................... 435/7.23
See application file for complete search history.

(56) References Cited

U.S. PATENT DOCUMENTS

2015/0024961 A1    1/2015   Klass et al.

FOREIGN PATENT DOCUMENTS

| EP | 2889623 | 7/2015 |
|---|---|---|
| WO | 2010056337 | 5/2010 |
| WO | 2010065968 | 6/2010 |
| WO | 2010070276 | 6/2010 |
| WO | 2012115885 | 8/2012 |
| WO | 2016024918 | 2/2016 |
| WO | 2016033695 | 3/2016 |
| WO | 2016201064 | 12/2016 |
| WO | 2017087940 | 5/2017 |

OTHER PUBLICATIONS

Ohno et al (Molecular Therapy, 2013, 21(1): 185-191).*
Xitong et al (Gene, 2016, 575: 377-384).*
Wang Z, Gerstein M, & Snyder M (2009) RNA-Seq: a revolutionary tool for transcriptomics. Nature reviews 10(1):57-63.
Weiskopf, K., et al., Engineered SIRPalpha variants as immunotherapeutic adjuvants to anticancer antibodies. Science, 2013. 341(6141): p. 88-91.
Willingham, S.B., et al., The CD47-signal regulatory protein alpha (SIRPa) interaction is a therapeutic target for human solid tumors. Proc Natl Acad Sci U S A, 2012. 109(17): p. 6662-6667.
Wisniewski JR, Zougman A, Nagaraj N, & Mann M (2009) Universal sample preparation method for proteome analysis. Nat Methods 6(5):359-362.
Zhang, L., et al., Nanoparticles in medicine: therapeutic applications and developments. Clin Pharmacol Ther, 2008. 83(5): p. 761-769.
International Search Report and Written Opinion for PCT Appl. PCT/US2017/057479, dated Mar. 8, 2018, 22 pages.
Al-Hajj, M., et al., Prospective identification of tumorigenic breast cancer cells. Proc Natl Acad Sci U S A, 2003. 100(7): p. 3983-3988.
Alvarez-Erviti, L., et al., Delivery of siRNA to the mouse brain by systemic injection of targeted exosomes. Nat Biotechnol, 2011. 29(4): p. 341-345.
Azmi AS, Bao B, & Sarkar FH (2013) Exosomes in cancer development, metastasis, and drug resistance: a comprehensive review. Cancer Metastasis Rev 32(3-4):623-642.
Bockhorn, J., et al., MicroRNA-30c inhibits human breast tumour chemotherapy resistance by regulating TWF1 and IL-11. Nat Commun, 2013. 4: p. 1393.
Bockhorn, J., et al., MicroRNA-30c targets cytoskeleton genes involved in breast cancer cell invasion. Breast Cancer Res Treat, 2013. 137(2): p. 373-382.
Chao, M. P. et al. Anti-CD47 antibody synergizes with rituximab to promote phagocytosis and eradicate non-Hodgkin lymphoma. Cell 142, 699-713, doi:10.1016/j.cell.2010.07.044 (2010).
Chao, M. P. et al. Calreticulin is the dominant pro-phagocytic signal on multiple human cancers and is counterbalanced by CD47. Sci Transl Med 2, 63ra94, doi:10.1126/scitranslmed.3001375 (2010).
Chao, M.P., et al., Extranodal dissemination of non-Hodgkin lymphoma requires CD47 and is inhibited by anti-CD47 antibody therapy. Blood, 2011. 118(18): p. 4890-4901.
Chao, M. P., Weissman, I. L. & Majeti, R. The CD47-SIRPalpha pathway in cancer immune evasion and potential terapeutic implications. Curr Opin Immunol 24, 225-232, doi:10.1016/j.coi.2012. 01.010 (2012).

(Continued)

*Primary Examiner* — Sean E Aeder
(74) *Attorney, Agent, or Firm* — Quarles & Brady LLP

(57) ABSTRACT

This invention is related to use of exosomes for biomarker analysis for early detecting and characterizing of disease progression of cancer. Further, the invention provides bio-engineered exosomes for use in methods of targeting and treating cancer.

12 Claims, 48 Drawing Sheets
(34 of 48 Drawing Sheet(s) Filed in Color)
Specification includes a Sequence Listing.

(56) References Cited

OTHER PUBLICATIONS

Chao, M. P., Majeti, R. & Weissman, I. L. Programmed cell removal: a new obstacle in the road to developing cancer. Nature reviews. Cancer 12, 58-67, doi:10.1038/nrc3171 (2012).
Dalerba, P. et al. Phenotypic characterization of human colorectal cancer stem cells. Proc Natl Acad Sci U S A 104, 10158-10163, doi:10.1073/pnas.0703478104 (2007).
Dragovic, R. A. et al. Sizing and phenotyping of cellular vesicles using Nanoparticle Tracking Analysis. Nanomedicine: nanotechnology, biology, and medicine 7, 780-788, doi:10.1016/j.nano.2011.04.003 (2011).
Godar, S. et al. Growth-inhibitory and tumor-suppressive functions of p53 depend on its repression of CD44 expression. Cell 134, 62-73, doi:10.1016/j.cell.2008.06.006 (2008).
Harding, C.V., J.E. Heuser, and P.D. Stahl, Exosomes: looking back three decades and into the future. J Cell Biol, 2013. 200(4): p. 367-371.
Hoshino A, et al. (2015) Tumour exosome integrins determine organotropic metastasis. Nature 527(7578):329-335.
Iero, M. et al. Tumour-released exosomes and their implications in cancer immunity. Cell death and differentiation 15, 80-88, doi:10.1038/sj.cdd.4402237 (2008).
Jaiswal, S. et al. CD47 is upregulated on circulating hematopoietic stem cells and leukemia cells to avoid phagocytosis. Cell 138, 271-285, doi:10.1016/j.cell.2009.05.046 (2009).
Kahlert, C. & Kalluri, R. Exosomes in tumor microenvironment influence cancer progression and metastasis. Journal of molecular medicine 91, 431-437, doi:10.1007/s00109-013-1020-6 (2013).
Kershaw, M. H. & Smyth, M. J. Immunology. Making macrophages eat cancer. Science 341, 41-42, doi:10.1126/science.1241716 (2013).
Kibria G, et al. (2016) A rapid, automated surface protein profiling of single circulating exosomes in human blood. Sci Rep 6:36502.
Lacroix, R. et al. Standardization of platelet-derived microparticle enumeration by flow cytometry with calibrated beads: results of the International Society on Thrombosis and Haemostasis SSC Collaborative workshop. Journal of thrombosis and haemostasis : JTH 8, 2571-2574, doi:10.1111/j.1538-7836.2010.04047.x (2010).
Li, C. et al. Identification of pancreatic cancer stem cells. Cancer research 67, 1030-1037, doi:10.1158/0008-5472.CAN-06-2030 (2007).
Liu H., et al., Cancer stem cells from human breast tumors are involved in spontaneous metastases in orthotopic mouse models. Proc Natl Acad Sci U S A, 2010. 107(42): p. 18115-18120.
Liu, H., MicroRNAs in breast cancer initiation and progression. Cell Mol Life Sci, 2012.
Lotvall, J. et al. Minimal experimental requirements for definition of extracellular vesicles and their functions: a position statement from the International Society for Extracellular Vesicles. Journal of extracellular vesicles 3, 26913, doi:10.3402/jev.v3.26913 (2014).
Mani, S. A. et al. The epithelial-mesenchymal transition generates cells with properties of stem cells. Cell 133, 704-715, doi:10.1016/j.cell.2008.03.027 (2008).
Marcucci F, Bellone M, Caserta CA, & Corti A (2014) Pushing tumor cells towards a malignant phenotype: stimuli from the microenvironment, intercellular communications and alternative roads. Int J Cancer 135(6):1265-1276.
Majeti, R., et al., CD47 is an adverse prognostic factor and therapeutic antibody target on human acute myeloid leukemia stem cells. Cell, 2009. 138(2): p. 286-299.
McCabe MT, et al. (2012) EZH2 inhibition as a therapeutic strategy for lymphoma with EZH2-activating mutations. Nature 492(7427):108-112.
Melo SA, et al. (2015) Glypican-1 identifies cancer exosomes and detects early pancreatic cancer. Nature 523 (7559):177-182.
Momen-Heravi, E et al. Current methods for the isolation of extracellular vesicles. Biological chemistry 394, 1253-1262, doi:10.1515/hsz-2013-0141 (2013).
Paltridge JL, Belle L, & Khew-Goodall Y (2013) The secretome in cancer progression. Biochim Biophys Acta 1834 (11):2233-2241.
Pospichalova, V. et al. Simplified protocol for flow cytometry analysis of fluorescently labeled exosomes and microvesicles using dedicated flow cytometer. Journal of extracellular vesicles 4, 25530, doi:10.3402/jev.v4.25530 (2015).
Prince, M. E. et al. Identification of a subpopulation of cells with cancer stem cell properties in head and neck squamous cell carcinoma. Proc Natl Acad Sci U S A 104, 973-978, doi:10.1073/pnas.0610117104 (2007).
Ramos, E. K., et al. (2017) New opportunities and challenges to defeat cancer stem cells. Tends in Cancer, 3(11):780-796.
Ruoslahti, E., S.N. Bhatia, and M.J. Sailor, Targeting of drugs and nanoparticles to tumors. J Cell Biol, 2010. 188(6): p. 759-768.
Samaeekia R, et al. miR-206 Inhibits Stemness and Metastasis of Breast Cancer by Targeting MKL1/IL11 Pathway. Clin Cancer Res. 2017;23(4):1091-1103.
Schlatzer DM, Sugalski J, Dazard JE, Chance MR, & Anthony DD (2012) A quantitative proteomic approach for detecting protein profiles of activated human myeloid dendritic cells. J Immunol Methods 375(1-2):39-45.
Schorey JS & Bhatnagar S (2008) Exosome function: from tumor immunology to pathogen biology. Traffic 9(6):871-881.
Shimono, Y., et al., Downregulation of miRNA-200c links breast cancer stem cells with normal stem cells. Cell, 2009. 138(3): p. 592-603.
Silva, J. et al. Analysis of exosome release and its prognostic value in human colorectal cancer. Genes, chromosomes & cancer 51, 409-418 (2012).
Simhadri, V. R. et al. Dendritic cells release HLA-B-associated transcript-3 positive exosomes to regulate natural killer function. PloS one 3, e3377, doi:10.1371/journal.pone.0003377 (2008).
Skog, J. et al., Glioblastoma microvesicles transport RNA and proteins that promote tumour growth and provide diagnostic biomarkers. Nat Cell Biol, 2008. 10(12): p. 1470-1476.
Svensson KJ & Belting M (2013) Role of extracellular membrane vesicles in intercellular communication of the tumour microenvironment. Biochem Soc Trans 41(1):273-276.
Thery, C., Amigorena, S., Raposo, G. & Clayton, A. Isolation and characterization of exosomes from cell culture supernatants and biological fluids. Current protocols in cell biology/editorial board, Juan S. Bonifacino . . . [et al.] chapter 3, Unit 3 22, doi:10.1002/0471143030.cb0322s30 (2006).
Valadi, H., et al., Exosome-mediated transfer of mRNAs and microRNAs is a novel mechanism of genetic exchange between cells. Nat Cell Biol, 2007. 9(6): p. 654-659.
van der Pol, E. et al. Optical and non-optical methods for detection and characterization of microparticles and exosomes. Journal of thrombosis and haemostasis: JTH 8, 2596-2607, doi:10.1111/j.1538-7836.2010.04074.x (2010).
van der Pol, E. et al. Particle size distribution of exosomes and microvesicles determined by transmission electron microscopy, flow cytometry, nanoparticle tracking analysis, and resistive pulse sensing. Journal of thrombosis and haemostasis : JTH 12, 1182-1192, doi:10.1111/jth.12602 (2014).
Verweij, F.J., et al., LMP1 association with CD63 in endosomes and secretion via exosomes limits constitutive NF-kappaB activation. EMBO J, 2011. 30(11): p. 2115-2129.
Vire E, et al. (2006) The Polycomb group protein EZH2 directly controls DNA methylation. Nature 439(7078):871-874.

\* cited by examiner

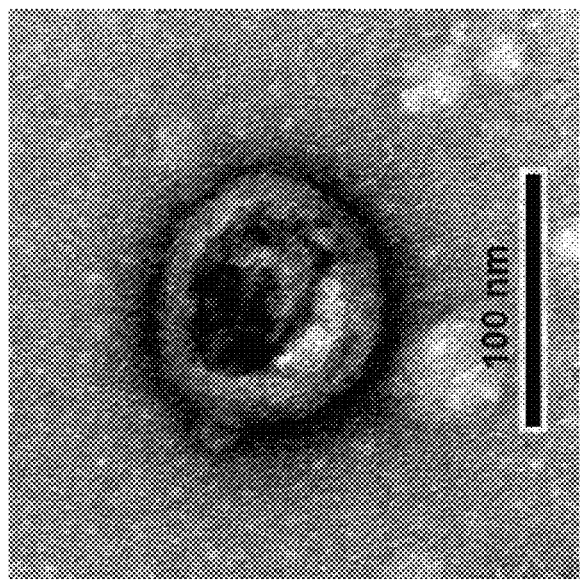
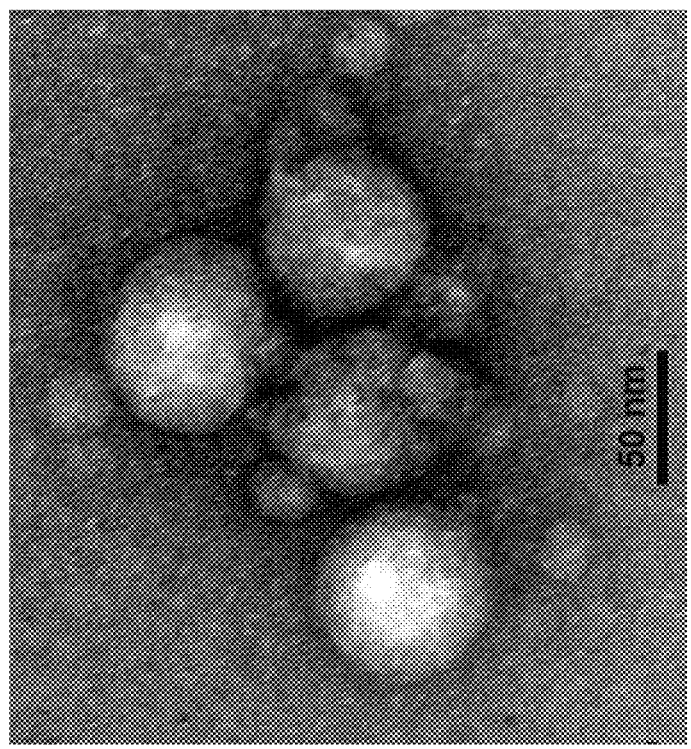
FIG. 4

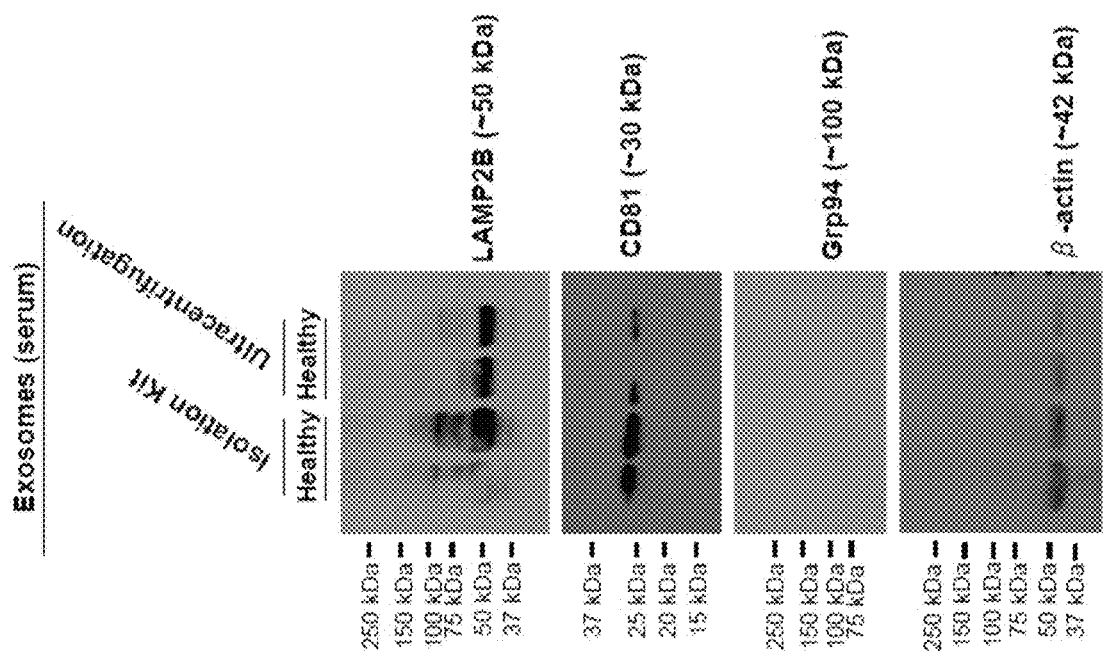

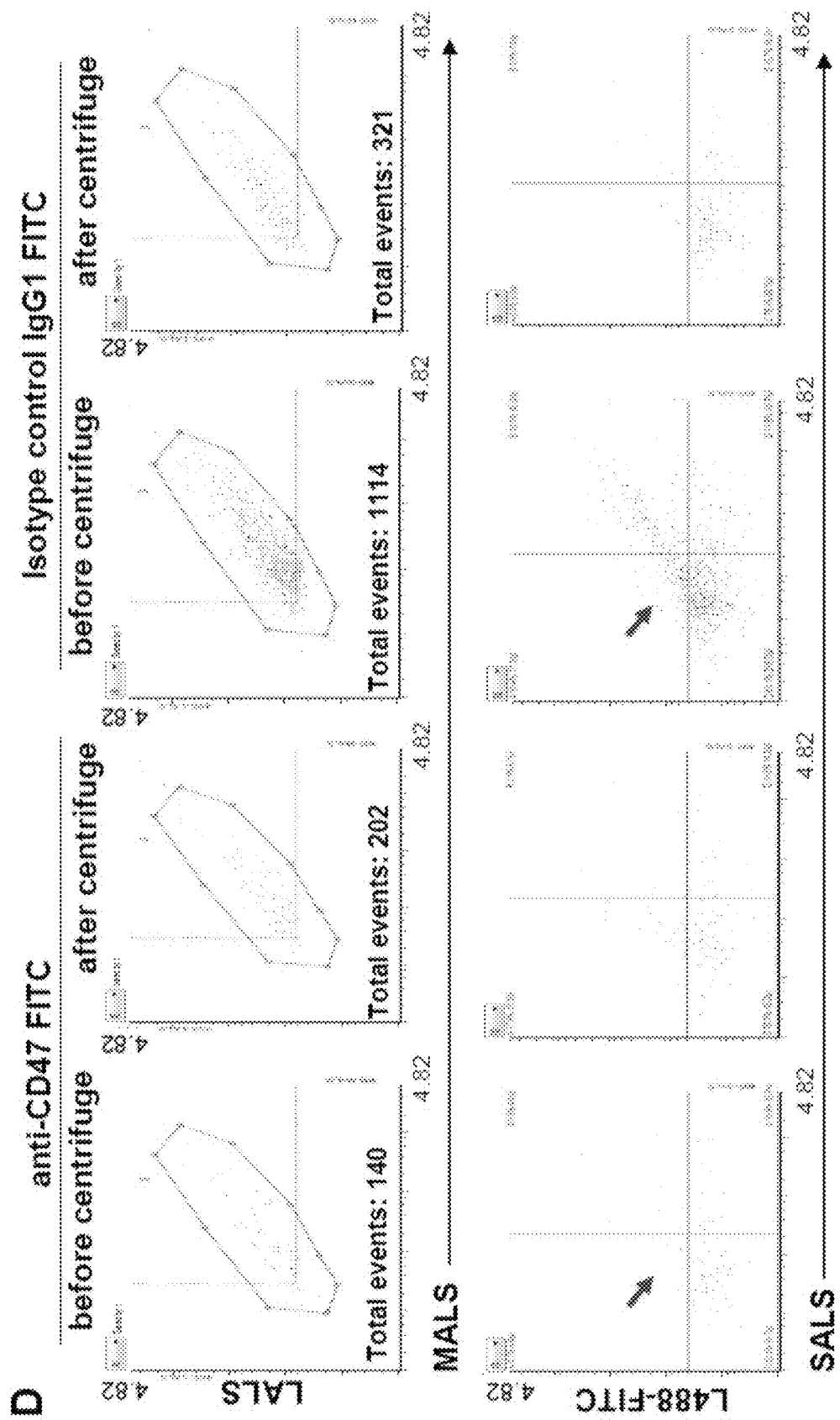
FIGS. 7A-7D COTINUED

FIG. 11

Clinical information of the female breast cancer patients and healthy controls (female) used in this study.

| Parameters | Breast Cancer Patients | Healthy Control |
|---|---|---|
| Total population | 60 | 60 |
| Age (years) | 48±10 | 50±7 |
| Sex | Female | Female |
| Tumor size (cm) | 4.7±2.4 | - |
| Her2+ | 43 | - |
| ER+ | 38 | - |
| PR+ | 28 | - |
| Treatment status (prior to blood drawn) | | |
| Untreated | 39 | - |
| Resection | 15 | - |
| Hormonal therapy | 1* | - |
| Masectomy | 3 | - |
| Unknown | 3 | - |

HER2+: HER2 positive; ER+: Estrogen receptor positive; PR+: Progesterone receptor positive; * indicates patient received hormonal therapy in addition to resection.

FIGS. 13A-13E
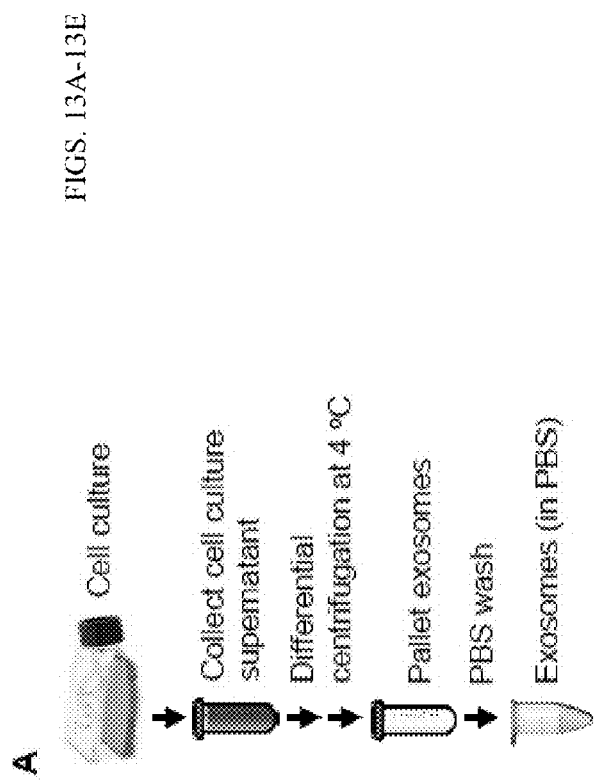
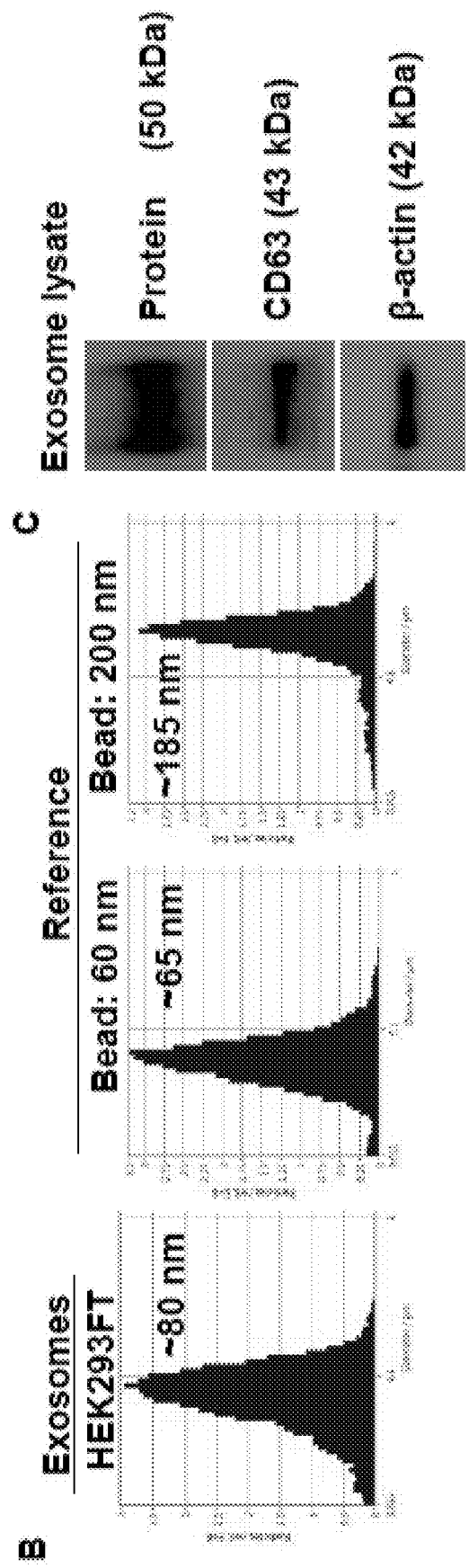

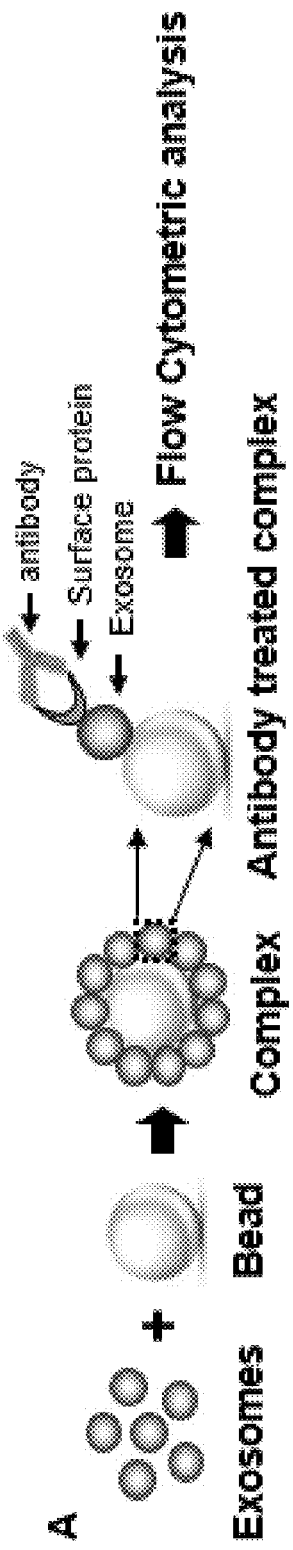
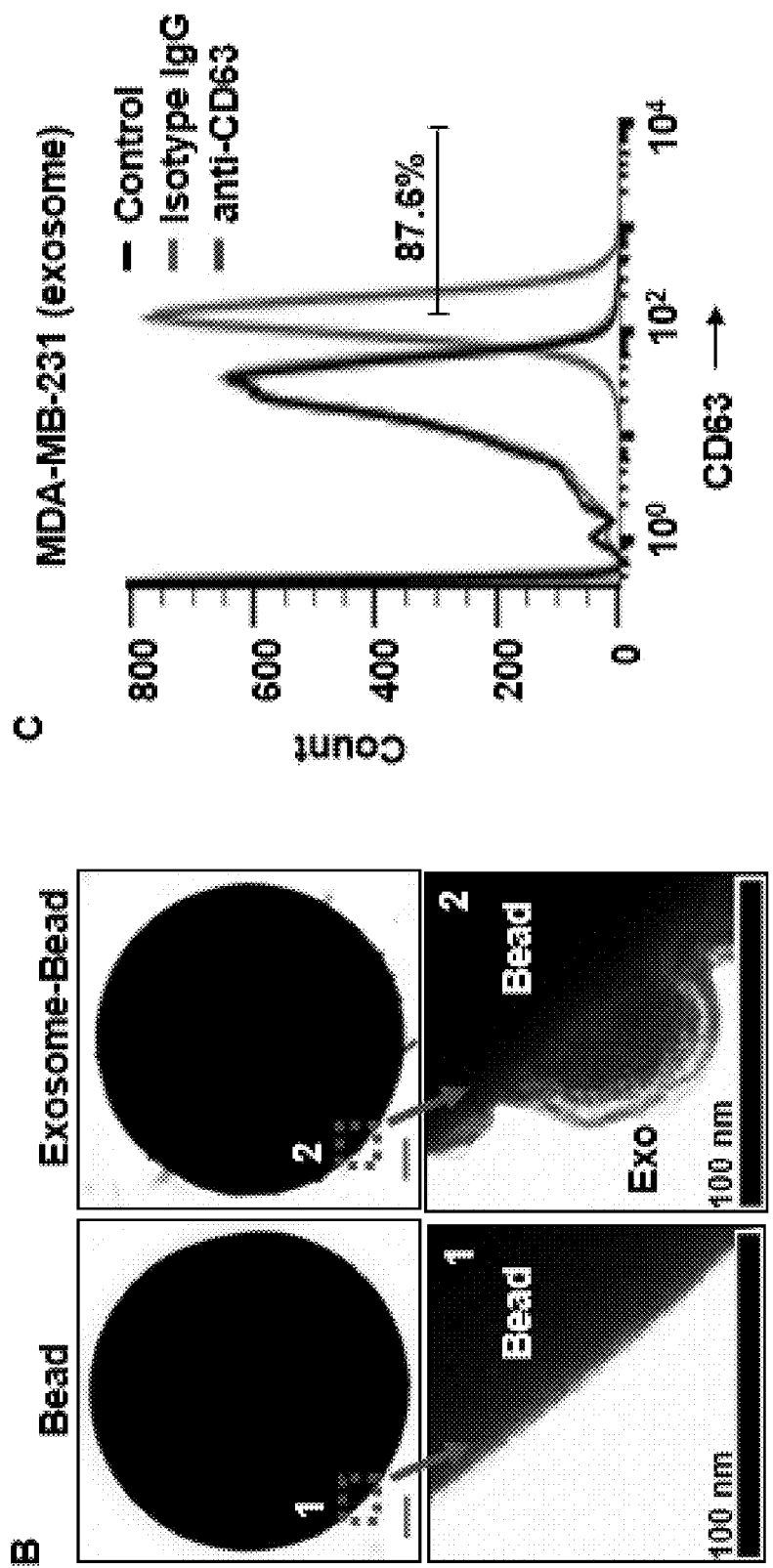
FIGS. 19A-19E

FIG. 23

| Symbol | Entrez.Gene.Name | Location | logFC | FDR |
|---|---|---|---|---|
| ACTN4 | actinin, alpha 4 | Cytoplasm | 2.063 | 0.026 |
| AGRN | agrin | Plasma Membrane | 6.394 | 0.001 |
| AHNAK | AHNAK nucleoprotein | Nucleus | 2.530 | 0.001 |
| ANXA6 | annexin A6 | Plasma Membrane | 6.710 | 0.000 |
| ARF6 | ADP ribosylation factor 6 | Plasma Membrane | 2.839 | 0.046 |
| ATP1B1 | ATPase, Na+/K+ transporting, beta 1 polypeptide | Plasma Membrane | 2.313 | 0.022 |
| CLTC | clathrin, heavy chain (Hc) | Plasma Membrane | 2.915 | 0.001 |
| CTNNB1 | catenin beta 1 | Nucleus | 3.593 | 0.041 |
| CTNND1 | catenin delta 1 | Nucleus | 3.668 | 0.041 |
| CYFIP1 | cytoplasmic FMR1 interacting protein 1 | Cytoplasm | 5.594 | 0.001 |
| DIP2B | disco interacting protein 2 homolog B | Cytoplasm | 5.220 | 0.014 |
| DYNC1H1 | dynein, cytoplasmic 1, heavy chain 1 | Cytoplasm | 4.802 | 0.033 |
| EHD1 | EH domain containing 1 | Cytoplasm | 5.752 | 0.000 |
| EHD4 | EH domain containing 4 | Plasma Membrane | 4.537 | 0.041 |
| EPCAM | epithelial cell adhesion molecule | Plasma Membrane | 2.637 | 0.041 |
| ERBB2 | erb-b2 receptor tyrosine kinase 2 | Plasma Membrane | 5.192 | 0.046 |
| FAM129B | family with sequence similarity 129 member B | Cytoplasm | 2.552 | 0.041 |
| FASN | fatty acid synthase | Cytoplasm | 4.473 | 0.001 |
| FKBP4 | FK506 binding protein 4 | Nucleus | 4.751 | 0.041 |
| GDI2 | GDP dissociation inhibitor 2 | Cytoplasm | 4.032 | 0.000 |
| GNA11 | guanine nucleotide binding protein (G protein), alpha 11 (Gq class) | Plasma Membrane | 4.959 | 0.007 |
| GNAS | GNAS complex locus | Plasma Membrane | 3.242 | 0.018 |
| IGSF3 | immunoglobulin superfamily member 3 | Plasma Membrane | 5.061 | 0.044 |
| IQGAP1 | IQ motif containing GTPase activating protein 1 | Cytoplasm | 5.386 | 0.000 |
| KRT8 | keratin 8, type II | Cytoplasm | 4.918 | 0.041 |
| MYO1C | myosin IC | Cytoplasm | 3.405 | 0.000 |
| NCKAP1 | NCK associated protein 1 | Plasma Membrane | 5.100 | 0.014 |
| NRAS | neuroblastoma RAS viral (v-ras) oncogene homolog | Plasma Membrane | 3.195 | 0.041 |
| PGK1 | phosphoglycerate kinase 1 | Cytoplasm | 2.090 | 0.014 |
| PLXNB2 | plexin B2 | Plasma Membrane | 5.709 | 0.001 |
| RAB5B | RAB5B, member RAS oncogene family | Cytoplasm | 4.358 | 0.041 |
| RAC1 | ras-related C3 botulinum toxin substrate 1 | Plasma Membrane | 2.146 | 0.018 |
| RAP1B | RAP1B, member of RAS oncogene family | Cytoplasm | 2.210 | 0.041 |
| RAP2B | RAP2B, member of RAS oncogene family | Plasma Membrane | 5.216 | 0.026 |
| SNAP23 | synaptosome associated protein 23kDa | Plasma Membrane | 4.612 | 0.026 |

FIG. 24

Representative CSC Markers expressed in different cancer types.

| Tumor Type | CSC Markers |
|---|---|
| Solid tumors | |
| Brain | CD133, CD49f, CD90, CD44 |
| Breast | CD44, CD24 (negative/low), EpCAM, ALDH |
| Colon | CD133, CD44, CD44v6, CD166, EpCAM, CD24, Lgr5 |
| Gastric | ALDH1, CD24/CD44, CD54/CD44, EpCAM/CD44, CD71-negative, CD90, CD133 |
| Lung | Sca1, CD34, CCA, CD133, ABCG2 |
| Melanoma | CD271, CD20 |
| Pancreatic | CD133, CD44, EpCAM, CD24 |
| Prostate | CD133, CD44, CD24 (negative) |
| Skin | SOX2 |
| Hematologic malignancies | |
| Acute myeloid leukemia | CD34, CD38 |
| Leukemia | CD34, CD38-negative, CD71-negative, CD90-negative, CD117-negative, CD123 |
| Metastases | |
| Pancreas | CD133, CXCR4 |
| Breast | CD44, CD36 |
| Melanoma | CD44, CD36 |
| Lung | CD109 |
| Colon | CD110, LGR5 |

FIG. 25

Figure 25. Sequence of the fusion protein LAMP2B-mSIRPα (XPepα) designed and required for the development of breast cancer stem cell targeted therapeutic bioengineered exosomes.

Cloning arm 1 : ▓▓▓▓▓▓▓GTACAAAAAAGCAGGCT (SEQ ID NO:1)

Gene sequence: (SEQ ID NO:2)

ACC ATG GTG TGC TTC CGC CTC TTC CCG GTT CCG GGC TCA GGG CTC GTT CTG
GTC TGC CTA GTC CTG GGA GCT GTG CGG TCT TAT GCA GGA GGT GGC AGT GGA
GGT GGC AGT GAG GAG GAG CTG CAG ATT ATT CAG CCT GAC AAG TCC GTG TTG
GTT GCA GCT GGA GAG ACA GCC ACT CTG CGC TGC ACT ATT ACC TCT CTG TTT
CCT GTG GGG CCC ATC CAG TGG TTC AGA GGA GCT GGA CCA GGC CGG GTT TTA
ATC TAC AAT CAA CGC CAA GGC CCT TTC CCC CGG GTA ACA ACT GTT TCA GAC
ACT ACA AAG AGA AAC AAC ATG GAC TTT TCC ATC CGC ATC GGT AAC ATC ACC
CCA GCA GAT GCC GGC ACC TAC TAC TGT ATT AAG TTC CGG AAA GGG AGC CCC
GAT GAC GTG GAG TTT AAG TCT GGA GCA GGC ACT GAG CTG TCT GTG CGC GCC
AAA CCC TCT GCC CCC GGA GGT AGT GGC GGA GGT AGT GGC CTA ATC CCA ATT
ATA GTT GGT GCT GGT CTT TCA GGC TTG ATT ATC GTT ATA GTG ATT GCT TAC
GTA ATT GGC AGA AGA AAA AGT TAT GCT GGA TAT CAG ACT CTG TAA

Cloning arm 2 : ACCCAGCTTT▓▓▓▓▓▓▓▓▓▓▓▓ (SEQ ID NO:3)

FIG. 25 continued

SEQ ID NO:4
SIRPa Signal peptide coding region
SIRPa variant-linkage coding region
Lamp2B transmembrane domain and cytoplasmic tail coding region CTTTCCTGCGTTATCCCCTGATTCTGTGGATAACCGTATTACCGCCTTTGAGTGAGCTG
ATACCGCTCGC
CGCAGCCGAACGACCGAGCGCAGCGAGTCAGTGAGCGAGGAAGCGGAAGAGCGCCCAAT
ACGCAAACCGC
CTCTCCCCGCGCGTTGGCCGATTCATTAATGCAGCTGGCACGACAGGTTTCCCGACTGG
AAAGCGGGCAG
TGAGCGCAACGCAATTAATACGCGTACCGCTAGCCAGGAAGAGTTTGTAGAAACGCAAA
AAGGCCATCCG
TCAGGATGGCCTTCTGCTTAGTTTGATGCCTGGCAGTTTATGGCGGGCGTCCTGCCCGC
CACCCTCCGGG
CCGTTGCTTCACAACGTTCAAATCCGCTCCCGGCGGATTTGTCCTACTCAGGAGAGCGT
TCACCGACAAA
CAACAGATAAAACGAAAGGCCCAGTCTTCCGACTGAGCCTTTCGTTTTATTTGATGCCT
GGCAGTTCCCT
ACTCTCGCGTTAACGCTAGCATGGATGTTTTCCCAGTCACGACGTTGTAAAACGACGGC
CAGTCTTAAGC
TCGGGCCCCAAATAATGATTTTATTTTGACTGATAGTGACCTGTTCGTTGCAACACATT
GATGAGCAATG
CTTTTTTATAATGCCAACTTTGTACAAAAAAGCAGGCT

FIG. 25 continued

```
ACCCAGCTTTCTTGTACAAAGTTGGCATTATAAGAAAGCATTGCTTATCAATTT
GTTGCAACGAACAGGTCACTATCAGTCAAAATAAAATCATTATTTGCCATCCAGCTGAT
ATCCCCTATAG
TGAGTCGTATTACATGGTCATAGCTGTTTCCTGGCAGCTCTGGCCCGTGTCTCAAAATC
TCTGATGTTAC
ATTGCACAAGATAAAATAATATCATCATGAACAATAAAACTGTCTGCTTACATAAACAG
TAATACAAGGG
GTGTTATGAGCCATATTCAACGGGAAACGTCGAGGCCGCGATTAAATTCCAACATGGAT
GCTGATTTATA
TGGGTATAAATGGGCTCGCGATAATGTCGGGCAATCAGGTGCGACAATCTATCGCTTGT
ATGGGAAGCCC
GATGCGCCAGAGTTGTTTCTGAAACATGGCAAAGGTAGCGTTGCCAATGATGTTACAGA
TGAGATGGTCA
GACTAAACTGGCTGACGGAATTTATGCCTCTTCCGACCATCAAGCATTTTATCCGTACT
CCTGATGATGC
ATGGTTACTCACCACTGCGATCCCCGGAAAAACAGCATTCCAGGTATTAGAAGAATATC
CTGATTCAGGT
GAAAATATTGTTGATGCGCTGGCAGTGTTCCTGCGCCGGTTGCATTCGATTCCTGTTTG
TAATTGTCCTT
TTAACAGCGATCGCGTATTTCGTCTCGCTCAGGCGCAATCACGAATGAATAACGGTTTG
GTTGATGCGAG
TGATTTTGATGACGAGCGTAATGGCTGGCCTGTTAACAAGTCTGGAAAGAAATGCATA
AACTTTTGCCA
TTCTCACCGGATTCAGTCGTCACTCATGGTGATTTCTCACTTGATAACCTTATTTTTGA
CGAGGGGAAAT
TAATAGGTTGTATTGATGTTGGACGAGTCGGAATCGCAGACCGATACCAGGATCTTGCC
ATCCTATGGAA
CTGCCTCGGTGAGTTTTCTCCTTCATTACAGAAACGGCTTTTTCAAAAATATGGTATTG
ATAATCCTGAT
ATGAATAAATTGCAGTTTCATTTGATGCTCGATGAGTTTTTCTAATCAGAATTGGTTAA
TTGGTTGTAAC
ACTGGCAGAGCATTACGCTGACTTGACGGGACGGCGCAAGCTCATGACCAAAATCCCTT
AACGTGAGTTA
CGCGTCGTTCCACTGAGCGTCAGACCCCGTAGAAAGATCAAGGATCTTCTTGAGATC
CTTTTTTTCTG
CGCGTAATCTGCTGCTTGCAAACAAAAAAACCACCGCTACCAGCGGTGGTTTGTTTGCC
GGATCAAGAGC
TACCAACTCTTTTTCCGAAGGTAACTGGCTTCAGCAGAGCGCAGATACCAAATACTGTT
CTTCTAGTGTA
GCCGTAGTTAGGCCACCACTTCAAGAACTCTGTAGCACCGCCTACATACCTCGCTCTGC
TAATCCTGTTA
```

FIG. 25 continued

CCAGTGGCTGCTGCCAGTGGCGATAAGTCGTGTCTTACCGGGTTGGACTCAAGACGATA
GTTACCGGATA
AGGCGCAGCGGTCGGGCTGAACGGGGGGTTCGTGCACACAGCCCAGCTTGGAGCGAACG
ACCTACACCGA
ACTGAGATACCTACAGCGTGAGCTATGAGAAAGCGCCACGCTTCCCGAAGGGAGAAAGG
CGGACAGGTAT
CCGGTAAGCGGCAGGGTCGGAACAGGAGAGCGCACGAGGGAGCTTCCAGGGGAAACGC
CTGGTATCTTT
ATAGTCCTGTCGGGTTTCGCCACCTCTGACTTGAGCGTCGATTTTTGTGATGCTCGTCA
GGGGGGCGGAG
CCTATGGAAAAACGCCAGCAACGCGGCCTTTTTACGGTTCCTGGCCTTTTGCTGGCCTT
TTGCTCACATG
TT

Restriction Enzyme Site Summary

| Name | Frequency | Position |
|---|---|---|
| AarI | 1 | 3497 (12865) |
| Acc65I | 1 | 8280 (12865) |
| AhdI | 1 | 11946 (12865) |

FIG. 25 continued

| Enzyme | Count | Positions |
|---|---|---|
| BaeI | 1 | 2743 (12865) |
| BaeI' | 1 | 2776 (12865) |
| BsaBI | 1 | 5549 (12865) |
| BsaXI | 5 | 2206 (2118),▓▓▓▓▓▓▓,9452 (844),10296 (632),10928 (4143) |
| BsmBI | 1 | 4776 (12865) |
| BspEI | 3 | ▓▓▓▓▓▓▓,4950 (3708),8658 (8484) |
| BstZ17I | 1 | 10674 (12865) |
| Bsu36I | 1 | 8276 (12865) |
| CspCI | 1 | 630 (12865) |
| CspCI' | 1 | 665 (12865) |
| EcoRV | 4 | ▓▓▓▓▓▓▓,7525 (860),8385 (79),8464 (8878) |
| FseI | 1 | 10314 (12865) |
| HpaI | 1 | 6307 (12865) |
| KpnI | 1 | 8284 (12865) |
| MauBI | 1 | 10074 (12865) |
| MluI | 1 | 232 (12865) |
| MreI | 1 | 5165 (12865) |
| NdeI | 1 | 488 (12865) |
| PacI | 1 | 2579 (12865) |
| PciI | 1 | 11053 (12865) |
| PflMI | 2 | ▓▓▓▓▓▓▓,7782 (9189) |
| PmeI | 1 | 8861 (12865) |
| PvuI | 1 | 12316 (12865) |
| SfiI | 1 | 9862 (12865) |
| SgrDI | 1 | 2 (12865) |
| SmaI | 3 | ▓▓▓▓▓▓▓,9932 (196),10128 (6908) |
| SnaBI | 2 | 594 (3852),▓▓▓▓▓▓▓ |
| SspI | 1 | (12749) 12750 (116) |
| TstI | 1 | (3599) 3600 (9266) |
| TstI' | 1 | (3567) 3568 (9298) |
| XbaI | 2 | (3838) 3839 (1211),5050 (7816) |
| XhoI | 1 | (8142) 8143 (4723) |
| XmaI | 3 | ▓▓▓▓▓▓▓,9930 (196),10126 (6908) |

Expected Vector sequence (12,865 bp): (SEQ ID NO:5)

gtcgacggatcgggagatctcccgatccccctatggtgcactctcagtacaatctgctctgatgccgcatagttaagccagtatctgctccctgc
ttgtgtgttggaggtcgctgagtagtgcgcgagcaaaatttaagctacaacaaggcaaggcttgaccgacaattgcatgaagaatctgcttag
ggttaggcgttttgcgctgcttcgcgatgtacgggccagatatacgcgttgacattgattattgactagttattaatagtaatcaattacggggtc
attagttcatagcccatatatggagttccgcgttacataacttacggtaaatggcccgcctggctgaccgcccaacgacccccgcccattgac
gtcaataatgacgtatgttcccatagtaacgccaatagggactttccattgacgtcaatgggtggactatttacggtaaactgcccacttggca
gtacatcaagtgtatcatatgccaagtacgccccctattgacgtcaatgacggtaaatggcccgcctggcattatgcccagtacatgaccttac
gggactttcctacttggcagtacatctacgtattagtcatcgctattaccatggtgatgcggttttggcagtacaccaatgggcgtggatagcg
gtttgactcacggggatttccaagtctccaccccattgacgtcaatgggagtttgttttggcaccaaaatcaacgggactttccaaaatgtcgta

FIG. 25 continued acaactccgccccattgacgcaaatgggcggtaggcgtgtacggtgggaggtctctgtactgggtctctctggttagaccagatctgagcct
gggagctctctggctaactagggaacccactgcttaagcctcaataaaagcttgccttgagtgcttcaagtagtgtgtgcccgtctgttgtgtga
ctctggtaactagagatccctcagacccttttagtcagtgtggaaaatctctagcagtggcgcccgaacagggacttgaaagcgaaaggga
aaccagaggagctctctcgacgcaggactcggcttgctgaagcgcgcacggcaagaggcgaggggcggcgactggtgagtacgccaa
aaattttgactagcggaggctagaaggagagagatgggtgcgagagcgtcagtattaagcgggggagaattagatcgcgatgggaaaaa
attcggttaaggccaggggggaaagaaaaaatataaattaaaacatatagtatgggcaagcagggagctagaacgattcgcagttaatcctg
gcctgttagaaacatcagaaggctgtagacaaatactgggacagctacaaccatcccttcagacaggatcagaagaacttagatcattatata
atacagtagcaaccctctattgtgtgcatcaaaggatagagataaaagacaccaaggaagctttagacaagatagaggaagagcaaaaca
aaagtaagaccaccgcacagcaagcggccgctgatcttcagacctggaggaggagatatgagggacaattggagaagtgaattatataaa
tataaagtagtaaaaattgaaccattaggagtagcacccaccaaggcaaagagaagagtggtgcagagagaaaaaagagcagtgggaat
aggagctttgttccttgggttcttgggagcagcaggaagcactatgggcgcagcgtcaatgacgctgacggtacaggccagacaattattgt
ctggtatagtgcagcagcagaacaatttgctgagggctattgaggcgcaacagcatctgttgcaactcacagtctggggcatcaagcagctc
caggcaagaatcctggctgtggaaagatacctaaaggatcaacagctcctggggatttggggttgctctggaaaactcatttgcaccactgc
tgtgccttggaatgctagttggagtaataaatctctggaacagatttggaatcacacgacctggatggagtgggacagagaaattaacaatta
cacaagcttaatacactccttaattgaagaatcgcaaaaccagcaagaaaagaatgaacaagaattattggaattagataaatgggcaagttt
gtggaattggtttaacataacaaattggctgtggtatataaaattattcataatgatagtaggaggcttggtaggtttaagaatagttttgctgtac
tttctatagtgaatagagttaggcagggatattcaccattatcgtttcagacccacctcccaaccccgagggggacccgacaggcccgaagga
atagaagaagaaggtggagagagagacagagacagatccattcgattagtgaacggatcggcactgcgtgcgccaattctgcagacaaat
ggcagtattcatccacaatttaaaagaaaagggggggattgggggggtacagtgcaggggaaagaatagtagaaataatagcaacagacat
acaaactaaagaattacaaaaacaaattacaaaaattcaaaattttcgggtttattacagggacagcagagatccagtttggttaattaacccgt
gtcggctccagatctggcctccgcgccgggttttggcgcctcccgcgggcgcccccctcctcacggcgagcgctgccacgtcagacgaa
gggcgcagcgagcgtcctgatccttccgcccggacgctcaggacagcggcccgctgctcataagactcggccttagaacccagtatca
gcagaaggacattttaggacgggacttgggtgactctagggcactggttttcttttccagagagcggaacaggcgaggaaaagtagtcccct
ctcggcgattctgcggagggatctccgtggggcggtgaacgccgatgattatataaggacgcgccgggtgtggcacagctagttccgtcg
cagccgggatttgggtcgcggttcttgtttgtggatcgctgtgatcgtcacttggtgagtagcgggctgctgggctggccggggctttcgtgg
ccgccgggccgctcggtgggacggaagcgtgtggagagaccgccaagggctgtagtctgggtccgcgagcaaggttgccctgaactgg
gggttgggggagcgcacaaaatggcggctgttcccgagtcttgaatggaagacgcttgtgaggcgggctgtgaggtcgttgaaacaag
gtgggggcatggtggcggcaagaacccaaggtcttgaggccttcgctaatgcgggaaagctcttattcgggtgagatgggctggggc
accatctggggaccccctgacgtgaagtttgtcactgactggagaaactcgggttgtcgtctgttgcgggggcggcagttatggcggtgccg
ttgggcagtgcacccgtacctttgggagcgcgcgcccctcgtcgtgtcgtgacgtcacccgttctgttggcttataatgcagggtggggccac
ctgccggtaggtgtcggtaggcttttctccgtcgcaggacgcagggttcgggcctagggtaggctctcctgaatcgacaggcgccggac
ctctggtgaggggagggataagtgaggcgtcagtttctttggtcggttttatgtacctatcttcttaagtagctgaagctccggttttgaactatg
cgctcggggttggcgagtgtgttttgtgaagttttttaggcaccttttgaaatgtaatcatttgggtcaatatgtaattttcagtgttagactagtaaa
ttgtccgctaaattctggccgttttggcttttttgttagacgaagcttgggctgcaggtcgactctagagcggccccgaattatcacaagtttG
TACAAAAAAGCAGGCTACC▓▓GTGTGCTTCCGCCTCTTCCCGGTTCCGGGCTCAGG
GCTCGTTCTGGTCTGCCTAGTCCTGGGAGCTGTGCGGTCTTATGCAGGAGGTGGCAG
TGGAGGTGGCAGTGAGGAGGAGCTGCAGATTATTCAGCCTGACAAGTCCGTGTTGG
TTGCAGCTGGAGAGACAGCCACTCTGCGCTGCACTATTACCTCTCTGTTTCCTGTGG
GGCCCATCCAGTGGTTCAGAGGAGCTGGACCAGGCCGGGTTTTAATCTACAATCAAC
GCCAAGGCCCTTTCCCCCGGGTAACAACTGTTTCAGACACTACAAAGAGAAACAAC
ATGGACTTTTCCATCCGCATCGGTAACATCACCCCAGCAGATGCCGGCACCTACTAC
TGTATTAAGTTCCGGAAAGGGAGCCCCGATGACGTGGAGTTTAAGTCTGGAGCAGG
CACTGAGCTGTCTGTGCGCGCCAAACCCTCTGCCCCCGGAGGTAGTGGCGGAGGTA

FIG. 25 continued

GTGGCCTAATCCCAATTATAGTTGGTGCTGGTCTTTCAGGCTTGATTATCGTTATAGT
GATTGCTTACGTAATTGGCAGAAGAAAAAGTTATGCTGGATATCAGACTCTGTAAAC
CCAGCTTTcttgtacaaagtggtgatcgcgttctaccgggtaggggaggcgcttttcccaaggcagtctggagcatgcgcttagcag
ccccgctgggcacttggcgctacacaagtggcctctggcctcgcacacattccacatccaccggtaggcgccaaccggctccgttctttggt
ggccccttcgcgccaccttctactcctcccctagtcaggaagttccccccgccccgcagctcgcgtcgtgcaggacgtgacaaatggaag
tagcacgtctcactagtctcgtgcagatggacagcaccgctgagcaatggaagcgggtaggcctttggggcagcggccaatagcagcttt
gctccttcgctttctgggctcagaggctgggaagggggtgggtccgggggcgggctcaggggcgggctcaggggcggggcgggcgccc
gaaggtcctccggaggcccggcattctgcacgcttcaaaagcgcacgtctgccgcgctgttctcctcttcctcatctccgggcctttcgacct
gcagcccaagcttactctagaggatcaaacttaagcttggcaatccggtactgttggtaaagccaccatggaagatgccaaaaacattaaga
agggcccagcgccattctacccactcgaagacggggaccgccggcgagcagctgcacaaagccatgaagcgctacgccctggtgcccg
gcaccatcgcctttaccgacgcacatatcgaggtggacattacctacgccgagtacttcgagatgagcgttcggctggcagaagctatgaa
gcgctatgggctgaatacaaaccatcggatcgtggtgtgcagcgagaatagcttgcagttcttcatgcccgtgttgggtgccctgttcatcgg
tgtggctgtggccccagctaacgacatctacaacgagcgcgagctgctgaacagcatgggcatcagccagcccaccgtcgtattcgtgag
caagaaagggctgcaaaagatcctcaacgtgcaaaagaagctaccgatcatacaaaagatcatcatcatggatagcaagaccgactacca
gggcttccaaagcatgtacaccttcgtgacttcccatttgccaccggcttcaacgagtacgacttcgtgcccgagagcttcgaccgggaca
aaaccatcgccctgatcatgaacagtagtggcagtaccggattgcccaagggcgtagccctaccgcaccgcaccgcttgtgtccgattcag
tcatgcccgcgaccccatcttcggcaaccagatcatccccgacaccgctatcctcagcgtggtgccatttcaccacggcttcggcatgttcac
cacgctgggctacttgatctgcggctttcgggtcgtgctcatgtaccgcttcgaggaggagctattcttgcgcagcttcaagactataagatt
caatctgccctgctggtgcccacactatttagcttcttcgctaagagcactctcatcgacaagtacgacctaagcaacttgcacgagatcgcc
agcggcggggcgccgctcagcaaggaggtaggtgaggccgtggccaaacgcttccacctaccaggcatccgccagggctacggcctg
acagaaacaaccagcgccattctgatcacccccgaaggggacgacaagcctggcgcagtaggcaaggtggtgcccttcttcgaggctaa
ggtggtggacttggacaccggtaagacactgggtgtgaaccagcgcggcgagctgtgcgtccgtggccccatgatcatgagcggctacg
ttaacaaccccgaggctacaaacgctctcatcgacaaggacggctggctgcacagcggcgacatcgcctactgggacgaggacgagca
cttcttcatcgtggaccggctgaagagcctgatcaaatacaagggctaccaggtagccccagccgaactggagagcatcctgctgcaaca
ccccaacatcttcgacgccggggtcgccggcctgcccgacgacgatgccggcgagctgccccgccgcagtcgtcgtgctggaacacggt
aaaaccatgaccgagaaggagatcgtggactatgtggccagccaggttacaaccgccaagaagctgcgcggtggtgttgtgttcgtggac
gaggtgcctaaaggactgaccggcaagttggacgcccgcaagatccgcgagattctcattaaggccaagaagggcggcaagatcgccgt
ggcctctgctgcctctgccatggtgagcaagggcgaggagctgttcaccggggtggtgcccatcctggtcgagctggacggcgacgtaa
acggccacaagttcagcgtgtccggcgagggcgagggcgatgccacctacggcaagctgaccctgaagttcatctgcaccaccggcaa
gctgcccgtgccctggcccacccttgtgaccaccctgacctacggcgtgcagtgcttcagccgctaccccgaccacatgaagcagcacg
acttcttcaagtccgccatgcccgaaggctacgtccaggagcgcaccatcttcttcaaggacgacggcaactacaagacccgcgccgagg
tgaagttcgagggcgacaccctggtgaaccgcatcgagctgaagggcatcgacttcaaggaggacggcaacatcctggggcacaagct
ggagtacaactacaacagccacaacgtctatatcatggccgacaagcagaagaacggcatcaaggtgaacttcaagatccgccacaacat
cgaggacggcagcgtgcagctcgccgaccactaccagcagaacacccccatcggcgacggccccgtgctgctgcccgacaaccacta
cctgagcacccagtccgccctgagcaaagaccccaacgagaagcgcgatcacatggtcctgctggagttcgtgaccgccgcgggatca
ctctcggcatggacgagctgtacaagtaaagcggccgcgacgctagagggcccgtttaattcgatatcaagcttatcgataatcaacctctg
gattacaaaatttgtgaaagattgactggtattcttaactatgttgctccttttacgctatgtggatacgctgctttaatgccttttgtatcatgctattg
cttcccgtatggctttcattttctcctccttgtataaatcctggttgctgtctctttatgaggagttgtggcccgttgtcaggcaacgtggcgtggtg
tgcactgtgtttgctgacgcaaccccccactggttggggcattgccaccacctgtcagctcctttccgggactttcgctttccccctccctattgc
cacggcggaactcatcgccgcctgccttgcccgctgctggacaggggctcggctgttgggcactgacaattccgtggtgttgtcggggaa
aatcatcgtcctttccttggctgctcgcctgtgttgccacctggattctgcgcgggacgtccttctgctacgtccttcggccctcaatccaagcg
gaccttccttcccgcggcctgctgccggctctgcgggcctcttccgcgtctttcgccttcgccctcagacgagtcggatctccctttgggcgct
ccccgcatcgatgtcgacctcgagaccggccgaactcgaagacctagaaaaaacattggagcaatcacaagtagcaatacagcagctac

FIG. 25 continued caatgctgattgtgcctggctagaagcacaagaggaggaggaggtgggttttccagtcacacctcaggtacctttaagaccaatgacttaca
aggcagctgtagatcttagccacttttaaaagaaaaggggggactggaagggctaattcactcccaacgaagacaagatatccttgatctgt
ggatctaccacacacaaggctacttccctgattggcagaactacacaccagggccagggatcagatatccactgacctttggatggtgctac
aagctagtaccagttgagcaagagaaggtagaagaagccaatgaaggagagaacacccgcttgttacaccctgtgagcctgcatgggatg
gatgacccggagagagaagtattagagtggaggtttgacagccgcctagcatttcatcacatggcccgagagctgcatccggactgtactg
ggtctctctggttagaccagatctgagcctgggagctctctggctaactagggaacccactgcttaagcctcaataaagcttgccttgagtgct
tcaagtagtgtgtgcccgtctgttgtgtgactctggtaactagagatccctcagacccttttagtcagtgtggaaaatctctagcagggcccgtt
taaacccgctgatcagcctcgactgtgccttctagttgccagccatctgttgtttgcccctccccgtgccttccttgaccctggaaggtgccac
tcccactgtcctttcctaataaaatgaggaaattgcatcgcattgtctgagtaggtgtcattctattctgggggtggggtggggcaggacagc
aagggggaggattgggaagacaatagcaggcatgctggggatgcggtgggctctatggcttctgaggcggaaagaaccagctggggct
ctaggggtatccccacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcggggcatcccttaggg
ttccgatttagtgctttacggcacctcgaccccaaaaaacttgattagggtgatggttcacgtagtgggccatcgcccctgatagacggtttttcg
ccctttgacgttggagtccacgttctttaatagtggactcttgttccaaactggaacaacactcaaccctatctcggtctattcttttgatttataag
ggattttggggatttcggcctattggttaaaaaatgagctgatttaacaaaaatttaacgcgaattaattctgtggaatgtgtgtcagttagggtgt
ggaaagtccccaggctccccagcaggcagaagtatgcaaagcatgcatctcaattagtcagcaaccaggtgtggaaagtccccaggctcc
ccagcaggcagaagtatgcaaagcatgcatctcaattagtcagcaaccatagtcccgcccctaactccgcccatcccgcccctaactccgc
ccagttccgcccattctccgccccatggctgactaatttttttatttatgcagaggccgaggccgcctcggcctctgagctattccagaagtag
tgaggaggcttttttggaggcctaggcttttgcaaaaagctcccgggagcttgtatatccattttcggatctgatcagcacgtgttgacaattaat
catcggcatagtatatcggcatagtataatacgacaaggtgaggaactaaaccatggccaagttgaccagtgccgttccggtgctcaccgc
gcgcgacgtcgccggagcggtcgagttctggaccgaccggctcggttctcccgggacttcgtggaggacgacttcgccggtgtggtcc
gggacgacgtgaccctgttcatcagcgcggtccaggaccaggtggtgccggacaacaccctggcctgggtgtgggtgcgcggcctgga
cgagctgtacgccgagtggtcggaggtcgtgtccacgaacttccgggacgcctccgggccggccatgaccgagatcggcgagcagccg
tgggggcgggagttcgccctgcgcgacccggccggcaactgcgtgcacttcgtggccgaggagcaggactgacacgtgctacgagattt
cgattccaccgccgccttctatgaaaggttgggcttcggaatcgttttccgggacgccggctggatgatcctccagcgcggggatctcatgc
tggagttcttcgcccacccccaacttgttattgcagcttataatggttacaaataaagcaatagcatcacaaatttcacaaataaagcattttttca
ctgcattctagttgtggtttgtccaaactcatcaatgtatcttatcatgtctgtataccgtcgacctctagctagagcttggcgtaatcatggtcata
gctgtttcctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctgcattaatgaatcggccaacgcgc
ggggagaggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaaggccag
gaaccgtaaaaaggccgcgttgctggcgtttttccataggctccgcccccctgacgagcatcacaaaaatcgacgctcaagtcagaggtgg
cgaaacccgacaggactataaagataccaggcgtttccccctggaagctccctcgtgcgctctcctgttccgaccctgccgcttaccggata
cctgtccgcctttctcccttcgggaagcgtggcgctttctcaatgctcacgctgtaggtatctcagttcggtgtaggtcgttcgctccaagctgg
gctgtgtgcacgaaccccccgttcagcccgaccgctgcgccttatccggtaactatcgtcttgagtccaacccggtaagacacgacttatcg
ccactggcagcagccactggtaacaggattagcagagcgaggtatgtaggcggtgctacagagttcttgaagtggtggcctaactacggct
acactagaaggacagtatttggtatctgcgctctgctgaagccagttaccttcggaaaaagagttggtagctcttgatccggcaaacaaacca
ccgctggtagcggtggtttttttgtttgcaagcagcagattacgcgcagaaaaaaaggatctcaagaagatcctttgatcttttctacggggtct
gacgctcagtggaacgaaaactcacgttaagggattttggtcatgagattatcaaaaaggatcttcacctagatccttttaaattaaaaatgaag
ttttaaatcaatctaaagtatatatgagtaaacttggtctgacagttaccaatgcttaatcagtgaggcacctatctcagcgatctgtctatttcgtt
catccatagttgcctgactccccgtcgtgtagataactacgatacgggagggcttaccatctggccccagtgctgcaatgataccgcgagac
ccacgctcaccggctccagatttatcagcaataaaccagccagccggaagggccgagcgcagaagtggtcctgcaactttatccgcctcc
atccagtctattaattgttgccgggaagctagagtaagtagttcgccagttaatagtttgcgcaacgttgttgccattgctacaggcatcgtggt

FIG. 25 continued gtcacgctcgtcgtttggtatggcttcattcagctccggttcccaacgatcaaggcgagttacatgatcccccatgttgtgcaaaaaagcggtt
agctccttcggtcctccgatcgttgtcagaagtaagttggccgcagtgttatcactcatggttatggcagcactgcataattctcttactgtcatg
ccatccgtaagatgcttttctgtgactggtgagtactcaaccaagtcattctgagaatagtgtatgcggcgaccgagttgctcttgcccggcgt
caatacgggataataccgcgccacatagcagaactttaaaagtgctcatcattggaaaacgttcttcggggcgaaaactctcaaggatcttac
cgctgttgagatccagttcgatgtaacccactcgtgcacccaactgatcttcagcatcttttactttcaccagcgtttctgggtgagcaaaaaca
ggaaggcaaaatgccgcaaaaaagggaataagggcgacacggaaatgttgaatactcatactcttccttttcaatattattgaagcatttatc
agggttattgtctcatgagcggatacatatttgaatgtatttagaaaaataaacaataggggttccgcgcacatttccccgaaaagtgccacct
gac

EXTRACELLULAR VESICLE-BASED DIAGNOSTICS AND ENGINEERED EXOSOMES FOR TARGETED THERAPEUTICS AGAINST CANCER

CROSS-REFERENCE TO RELATED APPLICATIONS

This application claims priority to U.S. Provisional Application 62/409,921 filed Oct. 19, 2016, the contents of which are incorporated by reference in its entirety.

STATEMENT REGARDING FEDERALLY SPONSORED RESEARCH

This invention was made with government support under R00 CA160638 awarded by the National Institutes of Health and W81XWH-16-1-0021 awarded by the U.S. Army Medical Research and Materiel Command (Army/MRMC). The government has certain rights in the invention.

BACKGROUND OF THE INVENTION

The field of the invention is related to cancer diagnostics and treatment. More particularly, the invention relates to exosomes and/or other extracellular vesicles (EVs) specific for cancer.

EVs are cell-derived vesicles with a closed double-layer membrane structure[1-3]. They carry various molecules (proteins, lipids, and RNAs) on their surface as well as in the lumen[1-3]. Exosomes and other EVs play a critical role in intercellular communication and cellular content transfer, e.g. mRNAs and microRNAs, in both physiological and pathological settings, such as tumor development and progression[4-7]. The exosomal surface proteins can mediate organ-specific homing of circulating exosomes, and their contents show potential to serve as novel biomarkers[8-10], thereby assisting the diagnosis and prognosis prediction of human diseases, such as cancer. Approaches to detect and characterize exosomes and other EVs may include: (1) electron microscopy (EM) to assess structure and size; (2) nanoparticle tracking analysis (NTA)[3] to reveal size and zeta potential; (3) protein analysis via immunofluorescence staining, western blotting, ELISA, and mass spectrometry, (4) RNA analysis using array platforms, RNA sequencing, and PCR, and (5) analysis of lipids, sugar, and other components by biochemical assays. Among these approaches, EM provides high-resolution imaging but is neither convenient nor affordable for high throughput molecular profiling of large numbers of circulating exosome samples for potential clinical applications. NTA utilizes light scattering and Brownian motion[3] to measure particle size but does not differentiate between vesicles within a size range of 5× orders of magnitude due to the low dynamic range of the camera[11]. In addition, NTA is not suitable for molecular profiling of exosomes because of low sensitivity to fluorescent signals.

Based on the statistics documented by American Cancer Society (http://www.cancer.org), the lifetime risk of developing cancer is 1 in 2 for men and 1 in 3 for women. And the lifetime risk of dying from cancer is 1 in 4 in men and 1 in 5 in women. The most frequent cancers are breast cancer in women and prostate cancer in men which are second leading cancers causing deaths. Breast cancer accounts for an estimated 230,000 newly diagnosed cases and about 40,000 deaths annually in USA (1.3 million new cases and 450,000 deaths every year worldwide). Lung cancer is the second leading cancer but the most devastating cancer in both men and women. Metastasis causes 90% of solid tumor-related deaths. Therefore prevention, detection and treatment of early and advanced diseases hold the key to reduce cancer mortality. To achieve those goals, better understanding of cancer and metastasis, novel biomarkers, and effective targeted therapies are demanded.

Cancer stem cells (CSCs) are a subset of cancer cells with tumor initiating capacity and stem cell properties, and considered the roots of cancer, seeds of metastasis, and sources of therapy resistance. However, it is challenging to detect CSCs, monitor residual CSC activities and remove CSCs through existing diagnostic and therapeutic approaches. There still is a need to identify CSC-related biomarkers in liquid biopsies such as circulating exosomes/EVs as well as to develop innovative CSC-targeted therapeutics.

SUMMARY OF THE INVENTION

The present invention overcomes the aforementioned drawbacks by providing single exosome/EV micro flow profile-based cancer biomarkers as well as engineered extracellular vesicles and exosomes to target specific cancer cell populations.

In one aspect, the invention provides a method of detecting cancer in a patient comprising: (a) obtaining a sample from the patient; (b) isolating extracellular vesicles from the sample; and (c) detecting expression of at least one cancer marker in the isolated extracellular vesicles.

In another aspect, the invention provides a method of bioengineering EVs or exosomes for targeting cancer cells, the method comprising: (a) expressing a fusion protein comprising a segment of an exosome protein fused to a cancer stem cell (CSC) targeting peptide in a host cell; and (b) isolating secreted EVs or exosomes comprising the fusion protein.

In another aspect, the invention provides bioengineered exosome made by the methods described herein.

In yet another aspect, the invention provides a bioengineered exosome comprising a fusion protein comprising a segment of an exosome protein fused to a CSC targeting peptide. In some aspects, the segment of the exosome protein comprises the transmembrane domain.

In a further aspect, the invention provides a therapeutic bioengineered exosome comprising a bioengineered exosome comprising a fusion protein comprising a segment of an exosome protein including the transmembrane domain fused to a CSC targeting peptide and at least one RNA oligonucleotide or chemotherapeutic agent.

In yet another aspect, the invention provides a method of treating a patient with cancer, the method comprising administering an effective amount of the therapeutic bioengineered exosome described herein.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4. Picture depicting the exosome-isolation kit-purified exosomes from human serum (healthy) under Transmission Electron Microscopy (TEM). Exosomes were isolated from the serum after depletion of cell debris and apoptotic bodies per manufacturer's manual.

FIG. 6. Pictures depicting immunoblot comparison of the expression of markers on exosomes isolated from human serum (healthy) by differential ultracentrifugation and by the exosome-isolation kit. Exosomal markers LAMP2B (~50 kDa) and CD81 (~30 kDa) were detected in exosomes (5 mg lysates). Grp94 (~100 kDa) and β-actin (~42 kDa) serve as a negative control and loading control, respectively.

FIG. 11. Table depicting Clinical Information of the female breast cancer patient and healthy control (female) used in this study.

FIG. 23 is a table showing the genes up-regulated in exosomes secreted by breast cancer cells (MDAMB-231, MCF-7, SKBR-3, BT-474) as compared to normal breast epithelial cells (MCF-10A, MCF-12A). The expression of HER2 was detected only in exosomes secreted by SKBR-3 and BT-474.

FIG. 24 shows representative CSC markers expressed in different cancer types.

DETAILED DESCRIPTION OF THE INVENTION

Figures 1A, 1B, 1C, 1D, 1E, 1F:
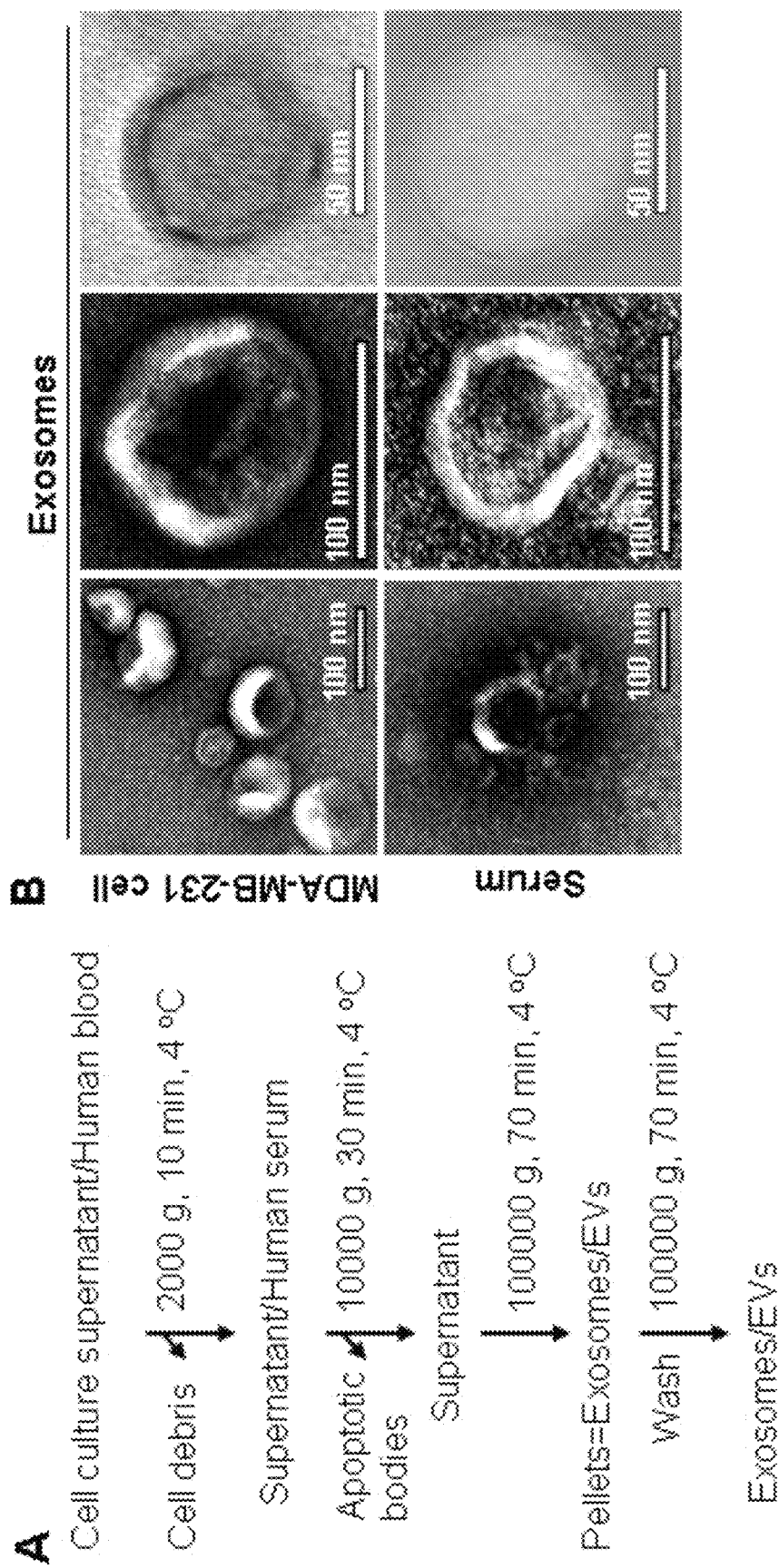
FIGS. 1A-1F. Isolation and characterization of exosomes from cell culture supernatant and human blood. A. Depicts the exosome purification procedure by ultracentrifugation. Blood was centrifuged at 3200 RPM for 15 min at 4° C. to collect serum or for 15 minutes at 2,000×g to collect plasma sample plasma. As mentioned in the first step, the cell culture supernatant was centrifuged at 2000 g, 10 min, 4° C. to remove cell debris. B. Picture representation of observation of the morphology of exosomes under Transmission Electron Microscopy (TEM), indicating the diameter of isolated exosomes in the 50-100 nm range. C. ZetaView NTA analysis of MDA-MB-231 cell-derived exosomes with the size distribution (mean diameter 89±33 nm and mode 87 nm) and surface charge (−30 mV). D. Immunoblot of exosomal markers CD81 (~30 kDa), CD63 (~55 kDa), and LAMP2B (~50 kDa) in exosomes (5 μg lysates) isolated from the serum of breast cancer patients and healthy control. Grp94 (~100 kDa) and β-actin (~42 kDa) serve as a negative control and a loading control, respectively. E. Immunoblot of Grp94 with 5 μg protein of MDA-MB-231 cell lysates (Cell) and the exosomes derived from these cells (Exosome, no Grp94 detection). F. Picture representation of detection of CD63 in intact MDA-MB-231 exosomes by immunofluorescence staining.
Figures 1A, 1B, 1C, 1D, 1E, 1F:
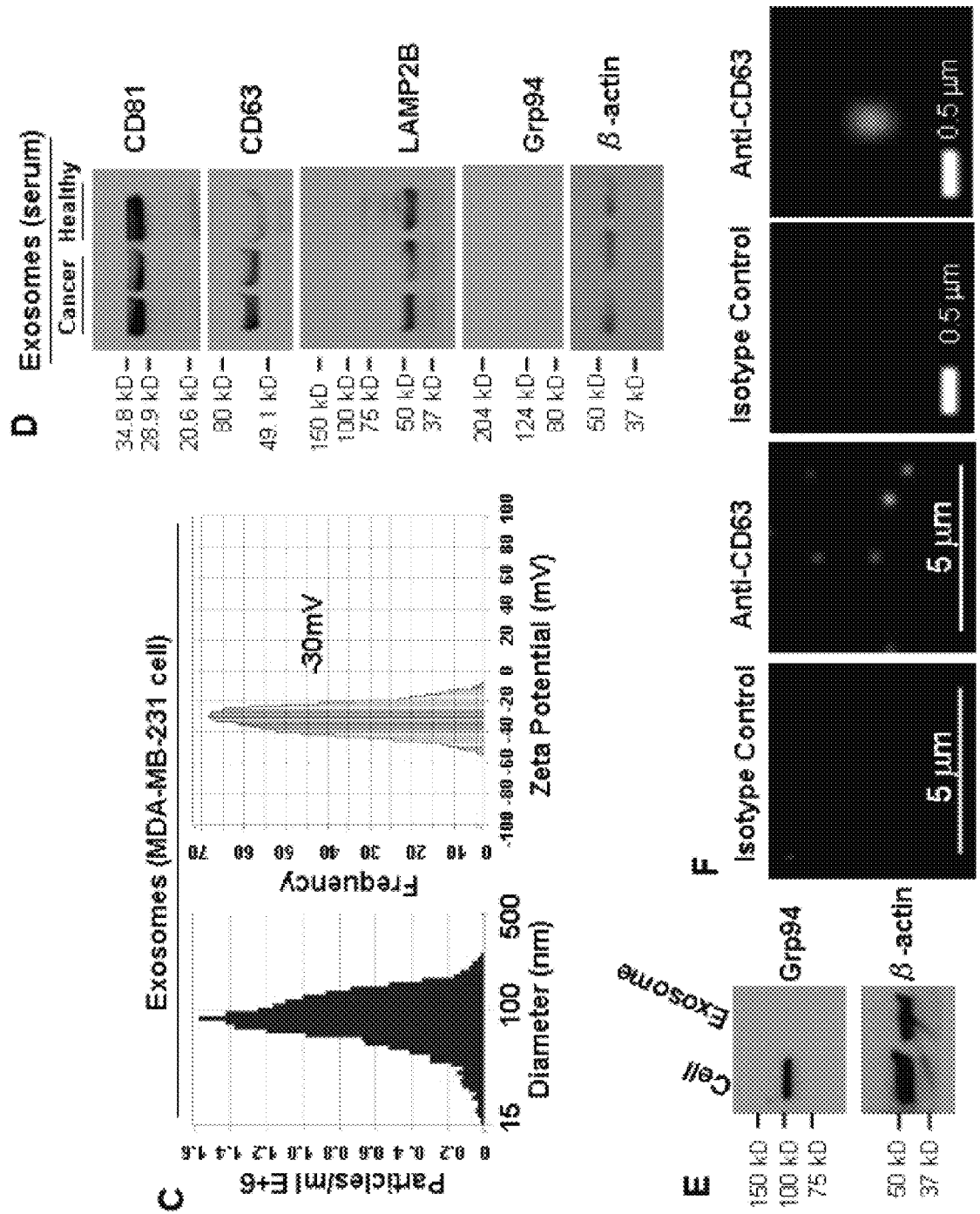

Embodiments of the present disclosure provide the use of extracellular vesicles and exosomes for cancer detection and diagnosis, cancer targeting and treatment. In one embodiment, the present disclosure describes a newly identified list of proteins differentially contained in cancer cell EVs/exosomes versus the normal cell EVs/exosomes as shown in FIG. 23. The inventors have also developed a novel method of detecting and profiling circulating exosomes and EVs from a subject at single vesicle levels in order to detect, diagnose and monitor disease development and progression. In one example, an expression profile of proteins on EVs and exosomes from patients with cancer can be used to distinguish the population with cancer from the healthy controls.

EVs are cell-derived vesicles with a closed double-layer membrane structure[1-3]. According to their size and density, EVs mainly include exosomes (30-150 nm), micro vesicles (MVs) (100-1000 nm), and apoptotic bodies or cancer related oncocomes (1-10 µm). Exosomes include multi-vesicle body (MVB)-derived EVs carrying specific markers such as CD63, CD9, CD81 and/or TSG101. EVs exist in virtually all body fluids of human, animals, bacteria, and plants, such as blood, urine, saliva, beer, milk, etc. EVs and exosomes are able to carry various molecules, such as proteins, lipids and RNAs on their surface as well as within their lumen. The EV and exosomal surface proteins can mediate organ-specific homing of circulating EVs and exosomes. As used herein, the term "extracellular vesicles" or "EVs" includes all cell-derived vesicles with a closed double-layer membrane structure derived from multivescular bodies or from the plasma membrane, including exosomes, microvesicles, and oncocomes.

As demonstrated in the Examples, the contents of EVs and exosomes are able to serve as novel biomarkers for assisting in the diagnosis, prognosis, and prediction of human diseases, such as cancer. The methods described herein may be used to monitor dynamic changes of exosome and EV contents to provide new ways of monitoring diseases. Further, the ability of EVs and exosomes to carry various molecules on their surface and within their lumen make them a useful tool for targeted drug delivery within a subject. Notably, the specific features of nano size, biological compatibility, small RNA content, immune regulating molecules, and structural stability make exosomes a novel class of nano drug delivery systems or immune regulation systems.

Approaches to detect and characterize exosomes and other EVs include: (1) electron microscopy (EM) to assess structure and size; (2) nanoparticle tracking analysis (NTA)[3] to reveal size and zeta potential; (3) protein analysis via immunofluorescence staining, western blotting, ELISA, and mass spectrometry, (4) RNA analysis using array platforms, RNA sequencing, and PCR, and (5) analysis of lipids, sugar, and other components by biochemical assays. Among these approaches, EM provides high-resolution imaging but is neither convenient nor affordable for high throughput molecular profiling of large numbers of circulating exosome samples for potential clinical applications. NTA utilizes light scattering and Brownian motion[3] to measure particle size but does not differentiate between vesicles within a size range of 5× orders of magnitude due to the low dynamic range of the camera[11]. In addition, NTA is not suitable for molecular profiling of exosomes because of low sensitivity to fluorescent signals. While all the EV or exosomal components potentially serve as molecular biomarkers of circulating vesicles in human disease, it is pivotal and necessary to improve high throughput profiling of surface molecules such as proteins in exosomes and other EVs, which could be readily detectable and serve as clinically relevant biomarkers. The present invention provides a method for readily detecting and profiling surface molecules of EVs and exosomes which can be used as biomarkers for specific diseases, specifically cancer.

The present invention provides a rapid and high throughput profiling of surface molecules at a single exosome/EV level. Although flow cytometry is a commonly used optical method to analyze cells based on the light scattering and fluorescence-activated mechanisms, conventional flow cytometers are only capable of detecting particles at a minimal size of 200-500 nm that is beyond the size of exosomes and small MVs. In addition, they are ineffective at discriminating particles that differ by 100-200 nm or less[2,12]. In conventional flow cytometry, the background signal is often high in the <200 nm size range, due to contaminating particles in the sheath buffer. Furthermore, the detectable level of immunolabeling signal is limiting in such small particles. Recently, latex beads in micrometer sizes have been used to bind to multiple exosomes to enhance the ability to detect exosomes stained with fluorophore-conjugated antibodies by conventional flow cytometry[10]. However, this bead-based approach does not provide single exosome profiling and therefore fails to discriminate between different subsets of exosomes, which may result in the loss of distinctive signatures with potential diagnostic importance. The present invention provides methods of detecting and profiling circulating exosomes and EVs from a subject at single vesicle levels in order to detect, diagnose and monitor disease development and progression. In one example, an expression profile of proteins on EVs and exosomes from patients with cancer can be used to distinguish the population with cancer from the healthy controls.

Cancer stem cells (CSCs) are a subset of cancer cells with tumor initiating capacity and stem cell properties, and considered the roots of cancer, seeds of metastasis, and sources of therapy resistance. Our laboratory has contributed to the findings that CD44$^+$CD24$^{-/low}$ breast cancer stem cells (BCSCs), which play a major role in breast tumor metastasis and therapy resistance. However, it has been challenging to detect CSCs, monitor residual CSC activities and remove CSCs through existing diagnostic and therapeutic approaches. The current invention provides in one embodiment a means for identifying CSC-related biomarkers in liquid biopsies such as circulating exosomes/EVs as well as innovative CSC-targeted therapeutics using CSC-specific EVs and exosomes.

In one embodiment, the disclosure provides bioengineered exosomes and EVs that express a fusion protein containing a cancer targeting peptide, e.g. a cancer stem cell targeting peptide and a segment of an exosome protein. In one embodiment, the fusion protein is XPepα comprising the transmembrane and cytoplasmic tail of exosome specific peptide Lamp2B with the extracellular domain replaced by mutant SIRPα extracellular domain, as demonstrated in the vector sequence in FIG. 25. The exosomes may be loaded with a RNA oligonucleotide or chemotherapeutic agent to provide a therapeutic exosome.

In one embodiment, the disclosure provides a method of detecting cancer specific exosomes/EVs from patients comprising: (a) obtaining a sample from the patient; (b) isolating the extracellular vesicles from the sample; and (c) detecting expression of at least one cancer marker in the isolated EVs. In one embodiment, the extracelluar vesicles are exosomes.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject. In a preferred embodiment, the subject is a human having or suspected of having cancer.

The term sample refers to a sample obtained from a subject. Suitable samples include a body fluid sample, such as, for example, blood, urine, cerebral spinal fluid, plasma, breast milk, saliva, or tissue samples (biopsy sample, tumor sample, breast tumor, other tumor tissues or normal tissues, among others).

In some embodiments, the EVs or exosomes that are isolated express one or more proteins that are preferentially expressed on cancer cells, for example, proteins that are preferentially expressed in cancer stem cells (CSCs). Suitable markers that are associated with cancer stem cells are known in the art and include, but are not limited to, for example, CD24, CD29, CD41, CD44, CD44V6, CD47, CD49b, CD49f, CD59, CD66, CD109 etc. Further, suitable CSC markers include the markers present in FIG. 24, for example, but not limited to the following: for solid tumors: e.g. brain cancer or tumors comprise markers CD133, CD49f, CD90, CD44, for solid breast cancer or tumors comprise markers CD44, CD24 (negative/low), EpCAM, ALDH; for solid colon cancer or tumors CD133, CD44, CD44v6, CD166, EpCAM, CD24, Lgr5; for gastric cancer or tumors comprise markers ALDH1, CD24/CD44, CD54/CD44, EpCAM/CD44, CD71-negative, CD90, CD133; for lung cancer comprise markers Sca1, CD34, CCA, CD133, ABCG2; for melanoma comprise markers CD271, CD20; for pancreatic cancer comprise markers CD133, CD44, EpCAM, CD24; for prostate cancer comprise markers CD133, CD44; for skin cancer comprise markers SOX2; for hematologic malignancies, for example, but not limited to, acute myeloid leukemia comprise markers CD34, CD38; for leukemia comprise markers CD34, CD38-negative, CD71-negative, CD90-negative, CD117-negative, CD123; for metastases, including but not limited to, for example, pancreas metastases include markers CD133, CXCR4; breast metastases include markers CD44, CD36; melanoma metastases include markers CD44, CD36; lung metastases include markers CD109 and colon metastases include markers CD110, LGR5. (See Erika K. Ramos et al. New Opportunities and Challenges to Defeat Cancer Stem Cells. *Trends in Cancer*, 2017, article in press, incorporated by reference in its entirety).

Suitable CSC markers for breast cancer include the markers listed in FIG. 23, including, but not limited to, ACTN4, AGR4, AHNAK, AN A6, ARF6, ATP1B1, CLTC, CTNNB1, CTNND1, C FIP1, DIP2B, D NC1H1, EHD1, EHD4, EPCAM, ERBB2, FAM129B, FASN, FKBP4, GDI2, GNA11, GNAS, IGSF3, IQGAP1, KRT8, M 1C, NCKAP1, NRAS, PGK1, PL NB2, RABSB, RAC1, RAP1B, RAP2B, SNAP23.

Suitably, in one method, the proteins that are preferentially expressed in cancer EVs are determined or identified by comparing EVs isolated from patients having cancer with EVs isolated from healthy, non-cancerous patients. In some embodiments, comparing EVs of healthy and cancer patients allows for identification of an EV protein profile that is associated with such cancer.

In some embodiments, the EVs are derived from and isolated from cancer stem cells (CSCs). In some embodiments, the EVs are exosomes, and in some embodiments, the exosomes are about 30 to about 150 nm in size, alternatively about 30 to about 100 nm in size.

Suitable methods of isolating EVs and exosomes are known in the art and include, but are not limited to, for example ultracentrifugation or exosome isolation kits which are commercially available (e.g. Total Exosome Isolation Kit from ThermoFisher Scientific).

In one embodiment, the EVs are isolated from a sample using beads or microspheres. The beads or microspheres are allowed to bind to the EVs and an antibody specific to a cancer antigen can be use for flow analysis of the sample. In some embodiments, bead-assisted flow cytometry is used to characterize the EVs derived from the subject.

EVs may be identified by the expression of one or more exosomal markers on the exosomes surface. Suitable exosomal markers include, but are not limited to, for example, CD63, CD81, CD9, LAMP2B, Tsg101, or Alix. In some embodiments, the methods are used with extracellular vesicles besides exosomes, in which case one or more of the exosome-specific markers may not be present.

In some embodiments, the EVs do not express Grp94.

In some embodiments, the detection of one or more cancer cell marker on the one or more EVs is by the novel micro flow cytometer (MFC) described in the Examiner which is performed in an automatic, sensitive, and high throughput manner, wherein the protein expression on individual EVs/exosomes is quantitatively measured and its association with cancer status analyzed. The MFC complements systemic mass spectrometry analysis, RNA sequencing, low-throughput but high resolution TEM known in the art.

In some embodiments, step (c) comprises determining a differential expression profile for at least one cancer marker in the samples from patients having cancer as compared to control healthy population known to not have cancer. In some embodiments, the differential expression profile includes at least two cancer cell markers, alternatively at least three cancer cell markers.

The methods described herein can be used for the detection, diagnosis, targeting and treatment of a subject having cancer, suitably solid tumor cancers, hematologic cancers and metastatic cancers. The terms "cancer," "tumor" and "cancerous" refer to or describe the physiological condition in mammals in which a population of cells are characterized by unregulated cell growth. A cancer may be a non-solid tumor type or a solid tumor. Examples of cancer include, but are not limited to, carcinoma, lymphoma, blastoma, sarcoma, and leukemia. More particular examples of such cancers include breast cancer, prostate cancer, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, colon cancer, colorectal cancer, gastric cancer, endometrial or uterine carcinoma, salivary gland carcinoma, kidney cancer, liver cancer, vulval cancer, thyroid cancer, hepatic carcinoma and various types of head and neck cancer, hematologic malignancies, acute myeloid leukemia, lymphoma and leukemia, metastases of the pancreas, breast, lung, colon, and melanoma, among others.

In a preferred embodiment, patients have or are suspected of having cancer. The circulating exosome/EV profiling approaches at single vesicle levels and collective levels (mass spectrometry) as described herein can be used for the identification of surface markers associated with diagnoses, prognoses and treatment of cancer. In a preferred embodiment, the cancer is selected from breast cancer, brain cancer, colon cancer, gastic cancer, lung cancer, melanoma, pancreatic cancer, prostate cancer, and skin cancer. In another embodiment, the cancer is a hematologic malignancy, for example, acute myeloid leukemia or leukemia.

In a preferred embodiment, the patient is suspected of or has breast cancer. In this embodiment, the chosen CSC relevant markers are CD47, CD44, HER2, EGFR, EpCAM and others.

In some embodiments, the cancer stem cell markers on individual EVs/exosomes within the isolated EVs/exosomes are detected. Suitable methods of detecting markers on individual exosomes include but are not limited to micro flow cytometry as described herein. This novel method of micro flow cytometry allows for the detection of markers on individual exosomes and EVs. This new method has advantages over prior methods of detecting EVs, such as florescent microscopy (FM), Transmission Electron Microscopy (TEM), nanoparticle tracking analysis (NTA). While these methods may also be used to detect EVs, these methods are time consuming, expensive for high-throughput molecular profiling of large number of circulating exosomes. FM is time consuming and provides false positive signal. TEM provides high-resolution imaging but is neither convenient nor affordable for high-throughput molecular profiling of large numbers of circulating exosome samples for potential clinical applications. NTA requires a very specific density of nanoparticles and it is not suitable for molecular profiling of exosomes. It is only with the methods of the present invention that a fast, high throughput system of profiling individual EVs has been developed.

The present disclosure also provides bioengineering EVs/exosomes and methods of making bioengineered EVs/exosomes for targeting cancer cells. A suitable method of making bioengineered EVs/exosomes comprises the steps of: (a) expressing a fusion protein comprising a segment of an exosome protein fused to a cancer targeting peptide (e.g. cancer stem cell targeting peptide) in a host cell; and (b) isolating secreted EVs/exosomes comprising the fusion protein. In a preferred embodiment, the EVs are exosomes but the methods can be used to produce bioengineered EVs in the same manner as producing exosomes.

One skilled in the art would be able design a suitable fusion protein for making of bioengineered EVs/exosomes using known cancer targeting peptides, including known CSC targeting peptides and segment of an exosome protein.

Suitably, the segment of the exosome protein includes at least a portion of the transmembrane domain of the exosome protein and a portion of the extracellular domain that is fused to the cancer targeting peptide, allowing for the fusion protein to be expressed on the surface of the exosome with the cancer targeting peptide on the extracellular side of the lipid bilayer. For example, a suitable transmembrane fragment of the LAMP2 peptide or other exosome specific transmembrane proteins can be used in the making of fusion proteins. The sequence of the fusion protein within an expression vector (20 kDa) is presented in FIG. 25.

In one embodiment, a fusion protein CSC targeting peptide is the mutant form of signal-regulatory protein alpha (SIRPα) fused to a fragment of LAMP2 exosome protein comprising at least a portion of the transmembrane domain for specifically targeting breast cancer cells. An example of the fusion gene sequence is found in FIG. 25.

In some embodiments, the method of producing bioengineered EVs/exosomes comprises transducing the host cell with a vector encoding for the fusion protein, for example, in a preferred embodiment, a viral vector. The vector allows for expression of the fusion protein within the host cell, allowing for the isolation from the host cell supernatant of bioengineered EVs/exosomes comprising the fusion protein. The lentiviral vector sequence is found in FIG. 25.

The present disclosure also provides a recombinant expression cassette comprising a polynucleotide according to embodiments of the present disclosure under the control of a transcriptional promoter allowing the regulation of the transcription of the polynucleotide in a host cell. The polynucleotide can also be linked to appropriate control sequences allowing the regulation of its translation in a host cell.

The present disclosure also provides a recombinant vector (e.g., a recombinant expression vector) comprising a polynucleotide fusion protein according to the present disclosure. Advantageously, the recombinant vector is a recombinant expression vector comprising an expression cassette according to the present disclosure.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

In some embodiments, the expression vector is a viral vector. Suitable viral vectors are known in the art and include, but are not limited to, for example, an adenovirus vector; an adeno-associated virus vector; a pox virus vector, such as a fowlpox virus vector; an alpha virus vector; a baclovirial vector; a herpes virus vector; a retrovirus vector, such as a lentivirus vector; a Modified Vaccinia virus Ankara vector; a Ross River virus vector; a Sindbis virus vector; a Semliki Forest virus vector; and a Venezuelan Equine Encephalitis virus vector. In a preferred embodiment, the viral vector is a lentiviral vector, an adenovirus vector or an adeno-associated virus vector.

The term "host cell" refers to a cell that is able to express the fusion protein via the expression vector. Suitable host cells include, for example, human primary cells or human cell lines. Suitable host cells include, but are not limited to, for example, mesenchymal stem cells (MSCs) or HEK293 cells, immature dendritic cells.

The present disclosure provides bioengineered EVs/exosomes comprising a fusion protein comprising a segment of an exosome protein fused to a cancer targeting peptide, e.g. a CSC targeting peptide as described herein. For example, the bioengineered EVs/exosome may express on its surface the fusion protein comprising a mutant form of signal-regulatory protein alpha (mSIRPα) and the exosome protein is a fragment of LAMP2 comprising at least the transmembrane domain. In a preferred embodiment, the exosome protein is LAMP2B.

Figure 25:
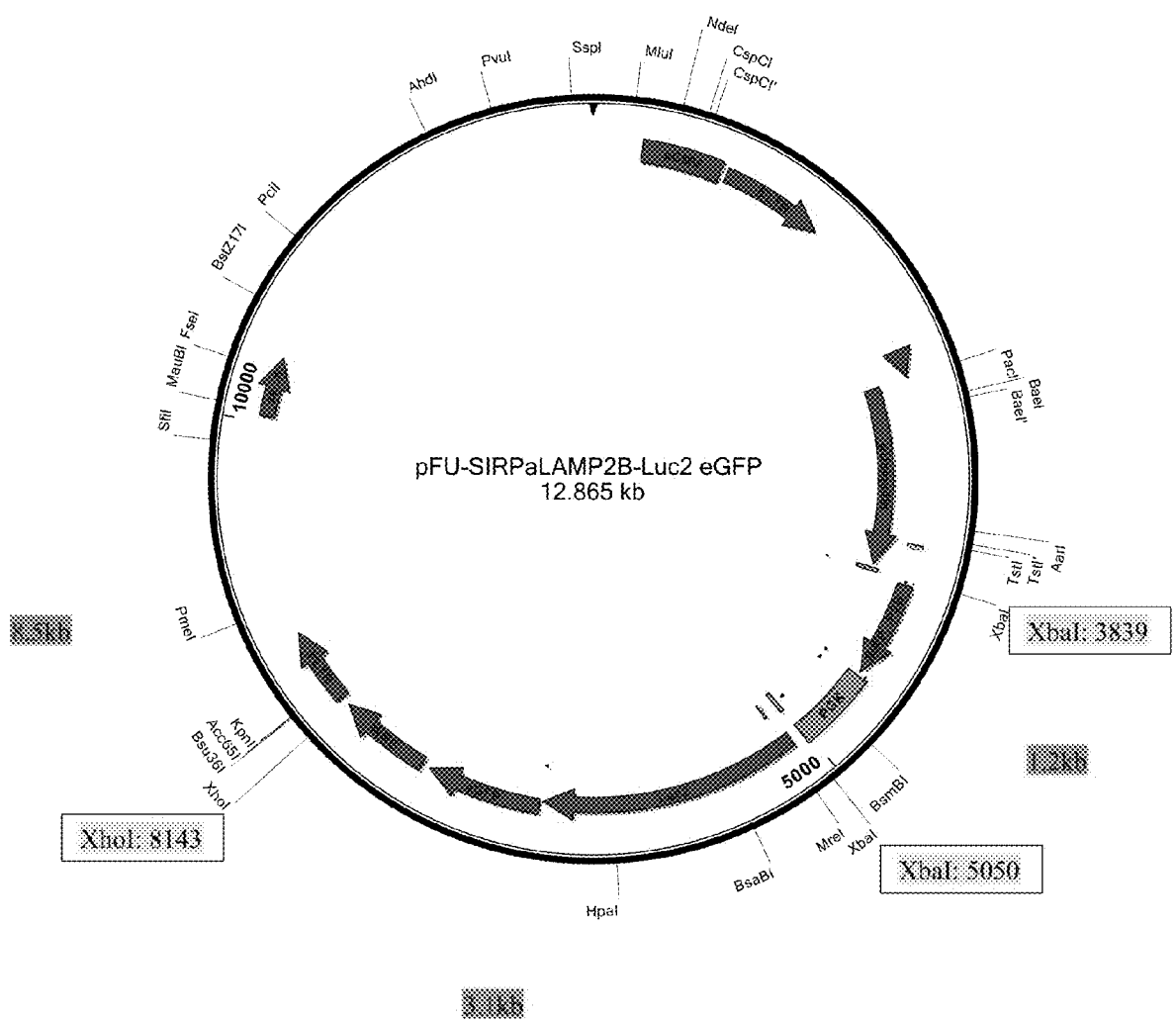
FIG. 25 shows the sequence of the fusion protein LAMP2B-mSIRPα (XPepα) designed and used for the development of breast cancer stem cell targeted therapeutic bioengineered exosomes.

In one embodiment, the fusion protein comprises SEQ ID NO:2. A suitable vector containing and able to express XPepα fusion protein in cells to produce extracellular vesicles is shown in FIG. 25.

In some embodiments, the bioengineered EVs/exosomes are therapeutic bioengineered EVs/exosomes that comprise the bioengineered exosomes described herein and at least one RNA oligonucleotide or chemotherapeutic agent.

The RNA oligonucleotides may be an asRNA, siRNA, or miRNA. A single-stranded RNA (antisense RNA (asRNA)) is complementary to a messenger RNA (mRNA) strand transcribed within a cell, the asRNA and are from about 15 to about 30 bp long. siRNA consists of two RNA strands, an antisense (or guide) strand and a sense (or passenger) strand, which form a duplex from about 19 to about 25 bp in length, usually with a 3' dinucleotide overhang. A microRNA (miRNA) is a small non-coding RNA molecule (containing about 20 to about 30 nucleotides) that functions in RNA silencing and post-transcriptional regulation of gene expression. Suitable aSRNA, siRNA and miRNA that can be used to specifically target cancers are known in the art. For example, in one embodiment of treating breast cancer, the miRNA is miR-200 or miR30c, miR206. Other suitable siRNA and miRNA for use in the present invention are disclosed in the following papers, the contents of which are incorporated by reference in their entirety: Bockhorn J, et al. MicroRNA-30c inhibits Human Breast Tumor Chemotherapy Resistance by regulating TWF1 and IL-11. *Nature Communications*. 2013; 4:1393, Samaeekia R, et al. miR-206 Inhibits Stemness and Metastasis of Breast Cancer by Targeting MKL1/IL11 Pathway. *Clin Cancer Res*. 2017; 23(4):1091-1103., Shimono Y, et al. Downregulation of miRNA-200c links breast cancer stem cells with normal stem cells. *Cell*. 2009; 138(3):592-603, Liu H. MicroRNAs in breast cancer initiation and progression. *Cell Mol Life Sci*. 2012; 69(21):3587-99.

In another embodiment, the therapeutic bioengineered EVs/exosomes may be loaded with a chemotherapeutic agent. By the term "loaded" the EVs/exosomes may contain the chemotherapeutic agent within its lipid bilayer or may be covalently or non-covalently linked to the chemotherapeutic agent by means known in the art. Suitable chemotherapeutic agents for use in the therapeutic bioengineered EVs/exosomes include, but are not limited to, for example. doxorubicin, cisplatin, paclitaxel, 5-fluorouracil, bevacizumab. Among others. Suitable chemotherapeutic agents would be identifiable and used in the present methods by one skilled in the art.

In one embodiment, suitable chemotherapeutic agents for treatment of breast cancer include, but are not limited to, for example, anastrozole (Arimidex®), bevacizumab (Avastin®), capecitabine (Xeloda®), cisplatin (Platinol®), cyclophosphamide (Cytoxan®), doxorubicin (Adriamycin®), exemestane (Aromasin®), 5-fluorouracil (5-FU), gemcitabine (Gemzar®), ixabepilone (Ixempra®), letrozole (Ferrara®), paclitaxel (Taxol®) and trastuzumab (Herceptin®).

The therapeutic bioengineered exosomes can specifically target a cancer cell by the cancer targeting peptide which is part of the fusion protein expressed by such exosomes. Thus, such bioengineered exosomes can be specifically targeted to carry the chemotherapeutic agent or RNA oligonucleotides to the specific cancer cells within a patient. Not to be bound by any theory, but the ability to specifically target RNA oligonucleotides or chemotherapeutic agents to the CSCs will allow for the reduction the cancer stem cells, which are believed to be the cells that result in the overproliferation of the cancer within a patient.

The present disclosure also provides methods of treating a patient with cancer. The method comprises administering an effective amount of the therapeutic bioengineered exosome in order to reduce, inhibit or limit the growth of the cancer.

The term "treat," "treating" or "treatment" of cancer encompasses, but is not limited to, reducing, inhibiting or limiting the growth of cancer cells, reducing, inhibiting or limiting metastasis of the cancer cells or invasiveness of the cancer cells or metastasis or reducing, inhibiting or limiting one or more symptoms of the cancer or metastasis thereof. As used herein, the term "inhibits growth of cancer cells" or "inhibiting growth of cancer cells" refers to any slowing of the rate of cancer cell proliferation and/or migration, arrest of cancer cell proliferation and/or migration, killing of cancer cells, or reducing cell viability, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, and reduce the presence of a tumor.

The terms "effective amount" or "therapeutically effective amount" refer to an amount sufficient to effect beneficial or desirable biological and/or clinical results. In one embodiment, the "effective amount" is an amount sufficient to inhibit, reduce or limit the growth cancer cells as compare with the observed or predicted rate of growth of an untreated control cancer.

In some embodiments, the bioengineered EVs/exosomes are administered with a pharmaceutically acceptable carrier. The term "pharmaceutically acceptable carrier" refers any carrier, diluent or excipient that is compatible with the other ingredients of the formulation and not deleterious to the recipient. A pharmaceutically acceptable carrier can be selected on the basis of the selected route of administration and standard pharmaceutical practice. The exosomes may be formulated into dosage forms according to standard practices in the field of pharmaceutical preparations. See Alphonso Gennaro, ed., Remington's Pharmaceutical Sciences, 18th Ed., (1990) Mack Publishing Co., Easton, Pa. Suitable dosage forms may comprise, but are not limited to, for example, solutions, parenteral solutions, injectable solutions, troches, suppositories, or suspensions. In a preferred embodiment, the exosomes are administered by intravenous or parenteral administration. In another embodiment, the exosomes are administered by direct injection into the tumor.

For parenteral administration, the active agent may be mixed with a suitable carrier or diluent such as, but not limited to, water, an oil (e.g., a vegetable oil), ethanol, saline solution (e, g., phosphate buffer saline or saline), aqueous dextrose (glucose) and related sugar solutions, glycerol, or a glycol such as propylene glycol or polyethylene glycol, or a carrier that is suitable for maintaining the viability of the dendritic cells. Stabilizing agents, antioxidant agents and preservatives may also be added. Suitable antioxidant agents include, but are not limited to, sulfite, ascorbic acid, citric acid and its salts, and sodium EDTA. Suitable preservatives include, but are not limited to, benzalkonium chloride, methyl- or propyl-paraben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component.

Kits

This disclosure provides kits. The kits can be suitable for use in the methods described herein.

In one aspect, a kit can include a first vector configured to express a fusion protein described herein comprising a cancer targeting peptide fused to a segment of an exosome protein. The kit may further comprise host cells capable of expressing the fusion protein from the vector. In one embodiment, the vector is a viral vector. In some embodiments, instructions on how to produced bioengineered exosomes are provided.

A further aspect provides a kit for treating a patient with cancer, the kit comprising a therapeutic bioengineered exosome described herein.

The present invention has been described in terms of one or more preferred embodiments, and it should be appreciated that many equivalents, alternatives, variations, and modifications, aside from those expressly stated, are possible and within the scope of the invention.

The following non-limiting examples are included for purposes of illustration only, and are not intended to limit the scope of the range of techniques and protocols in which the compositions and methods of the present invention may find utility, as will be appreciated by one of skill in the art and can be readily implemented.

EXAMPLES

Example 1: Rapid, Automated Surface Protein Profiling of Single Circulating Exosomes in Human Blood Circulating exosomes provide a promising approach to assess novel and dynamic biomarkers in human disease, due to their stability, accessibility and representation of molecules from source cells. However, this potential has been stymied by lack of approaches for molecular profiling of individual exosomes, which have a diameter of 30-150 nm. This Example demonstrates a rapid analysis approach to evaluate heterogeneous surface protein expression in single circulating exosomes from human blood. A differential CD47 expression in blood-derived individual circulating exosomes is correlated with breast cancer status, demonstrating a great potential of individual exosome profiles in biomarker discovery. The sensitive and high throughput platform of single exosome analysis can also be applied to characterizing exosomes derived from other patient fluids.

This Example provides a new, automated analytic approach utilizing a micro flow cytometer[13], and present data on its use to profile protein expressions of individual exosomes isolated from cell lines and human blood of breast cancer patients and healthy controls, as a proof of principle. We first assessed the expression of an exosomal marker, CD63, in cell-line derived exosomes following a rapid staining preparation and automated reading/counting procedure. Then we expanded to measure two cancer-related surface proteins, CD44[14-10] and CD47[20-24] in human blood-derived exosome specimens to assess correlations of these markers on exosomes with cancer status[14]. CD44 is a known marker for breast tumor initiating cells and is involved in tumor progression[14-19]. The expression of CD47 on the surface of the cancer cells prevents recognition by macrophages and natural killers, thereby inhibiting their ability to engulf and destroy those cancer cells[25,26].

Results

Figure 5:
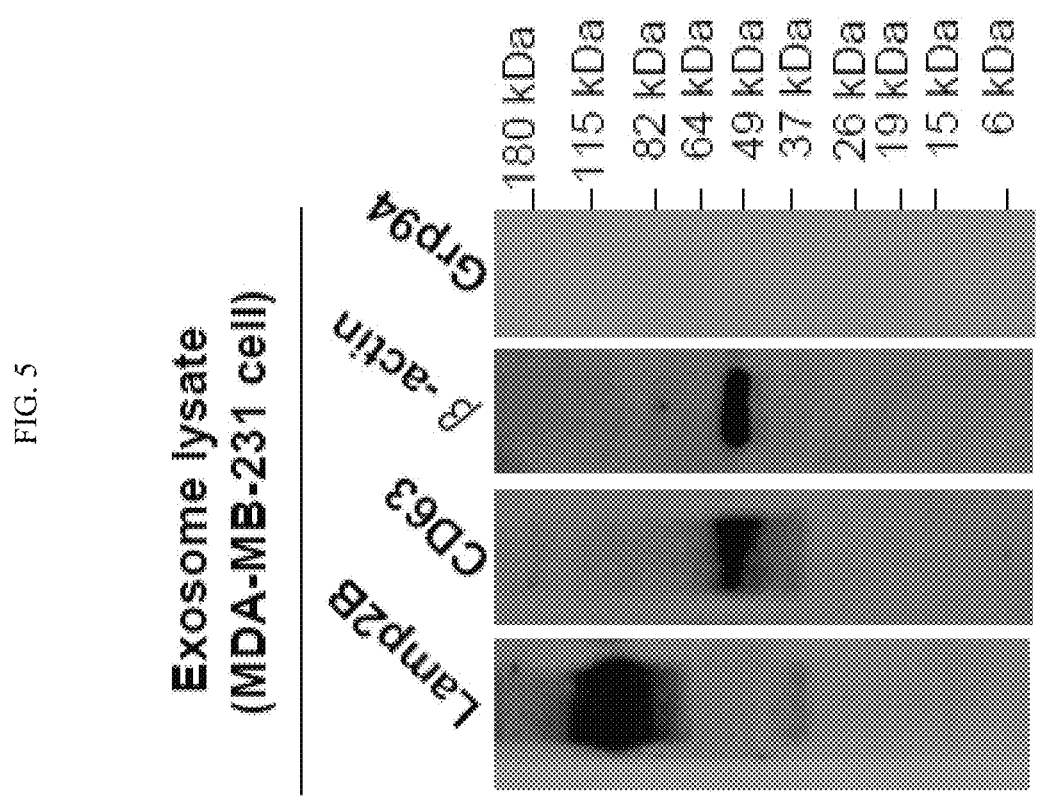
FIG. 5. Picture of gel depicting evaluation of the expression of exosomal markers on cell derived exosomes. Western blots of 5 μg exosome lysates for the exosomal markers LAMP2B (~100 kDa) and CD63 (~55 kDa). Grp94 (~100 kDa) and β-actin (~42 kDa) serves as a negative control and loading control, respectively.

Exosomes from breast cancer MDA-MB-231 cells and human serum samples were mainly isolated by differential ultracentrifugation[27] (FIG. 1A) unless specified in this report, which remains the most widely used and unbiased purification method[28]. In addition to differential ultracentrifugation method, we also isolated exosomes following a different method using the exosome-isolation kit from ThermoFisher Scientific. Both methods consistently purified exosomes with a double-layer membrane structure and a size range of about 50 to about 100 nm as observed by TEM (FIG. 1B, FIG. 4). According to the guidelines of the International Society of Extracellular Vesicles (ISEV) for the characterization of exosomes[29], multiple approaches were used to characterize the physical features and molecular markers of the isolated extracellular vesicles in order to identify these as exosomes. Measured by NTA (ZetaView), the mean size of exosomes was 89±33 nm and the surface charge of exosomes was about −30 mV (FIG. 1C), indicating the presence of negatively charged molecules on the surface of exosomes. Immunoblotting and immunofluorescence staining analyses of purified exosomes (without bead conjugation) confirmed the presence of at least three exosomal markers such as CD63, CD81 and LAMP2B[28,30], as well as the absence of Grp94 expression in the exosomes isolated from the serum (FIG. 1D) and cultured cells (FIG. 1E-F, FIG. 5). Additionally, the presence of CD81 and LAMP2B, as well as the absence of Grp94 markers were also observed in the exosomes isolated from human serum using the exosome-isolation kit (FIG. 6).

Figures 2A, 2B, 2C, 2D, 2E, 2F, 2G, 2H:
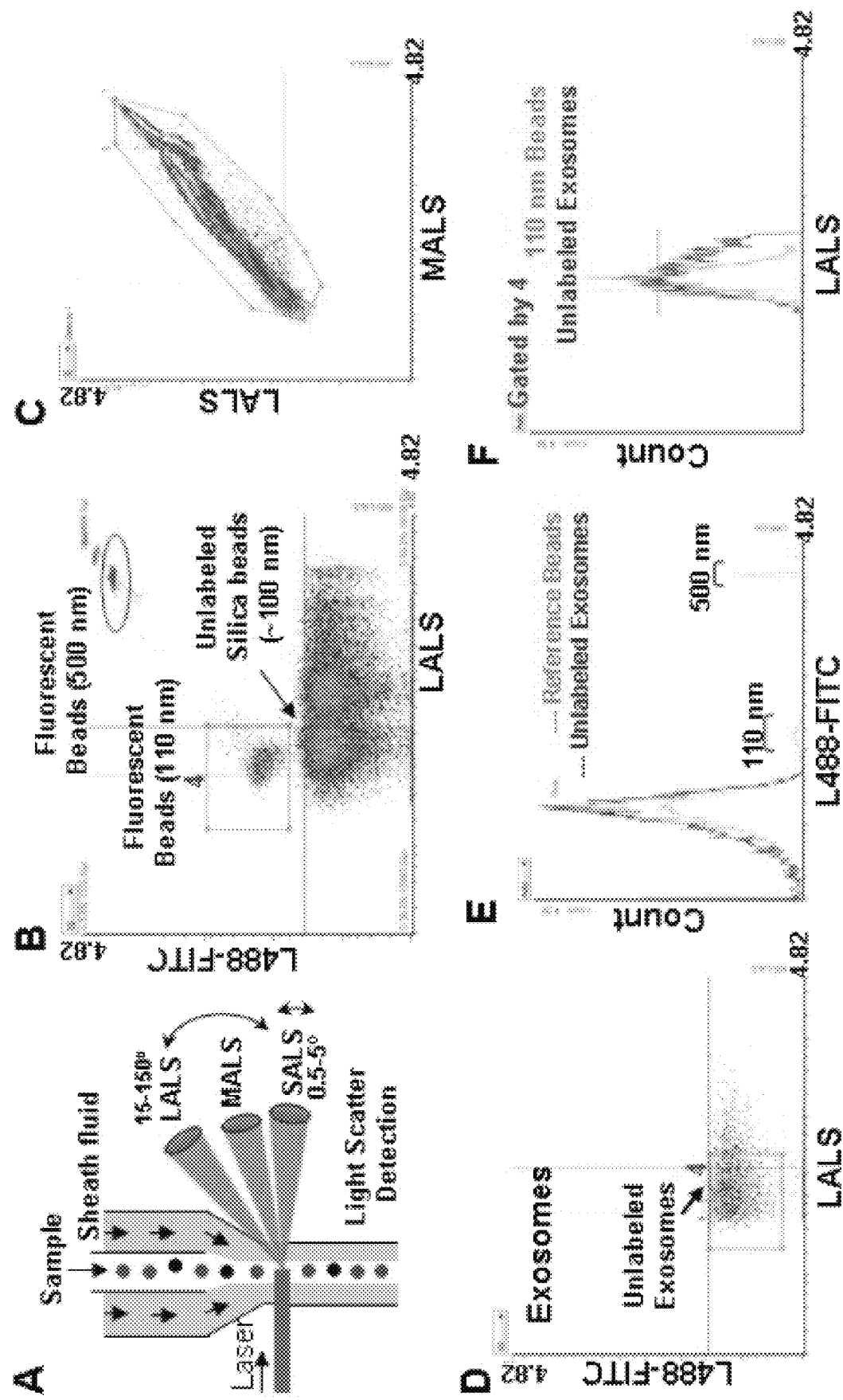
FIGS. 2A-2H. Micro flow cytometry (MFC) detection of the ApogeeMix Beads and blood-derived exosomes. A. Schematic representation of Apogee A50 MFC denoting the mode of action of nanoparticle detection. The sample flows from top to bottom and is surrounded by sheath fluid. The laser intersects with the sample stream, generating 3 different light scatters: Large angle light scatter (LAS); Middle angle light scatter (MALS); Small angle light scatter (SALS); and fluorescence signals. B. Cytogram of the reference beads, an aqueous mixture of the green fluorescent latex and non-fluorescent silica (Si) spheres in 110-1300 nm plotted at green fluorescence (L488-FITC) and LALS signals with minimized background noise. The red rectangle and circled box represent the 110 nm and 500 fluorescence beads respectively. C. Cytogram of the reference Apogee-Mix Beads in 110-1300 nm with similar MALS and LALS signals at the modified high threshold setting. D. Cytogram of the unlabeled exosomes from human blood at green fluorescence and LALS signals. E. Fluorescent signal comparison between the ApogeeMix beads from B and the unlabeled exosomes from D shown at the L488-FITC channel. F. Histogram comparing the size of the gated exosomes from D with that of the gated 110 nm fluorescence beads in B (red rectangles). G. Flow analysis of CD44 expression on exosomes derived from MDA-MB-231 and MCF-12A cells using A50 MFC. H. Immunoblot of CD44 expression in the exosome lysates derived from MDA-MB-231 and MCF-12A cells. β-actin (~42 kDa) serves as a loading control.
Figures 2A, 2B, 2C, 2D, 2E, 2F, 2G, 2H:
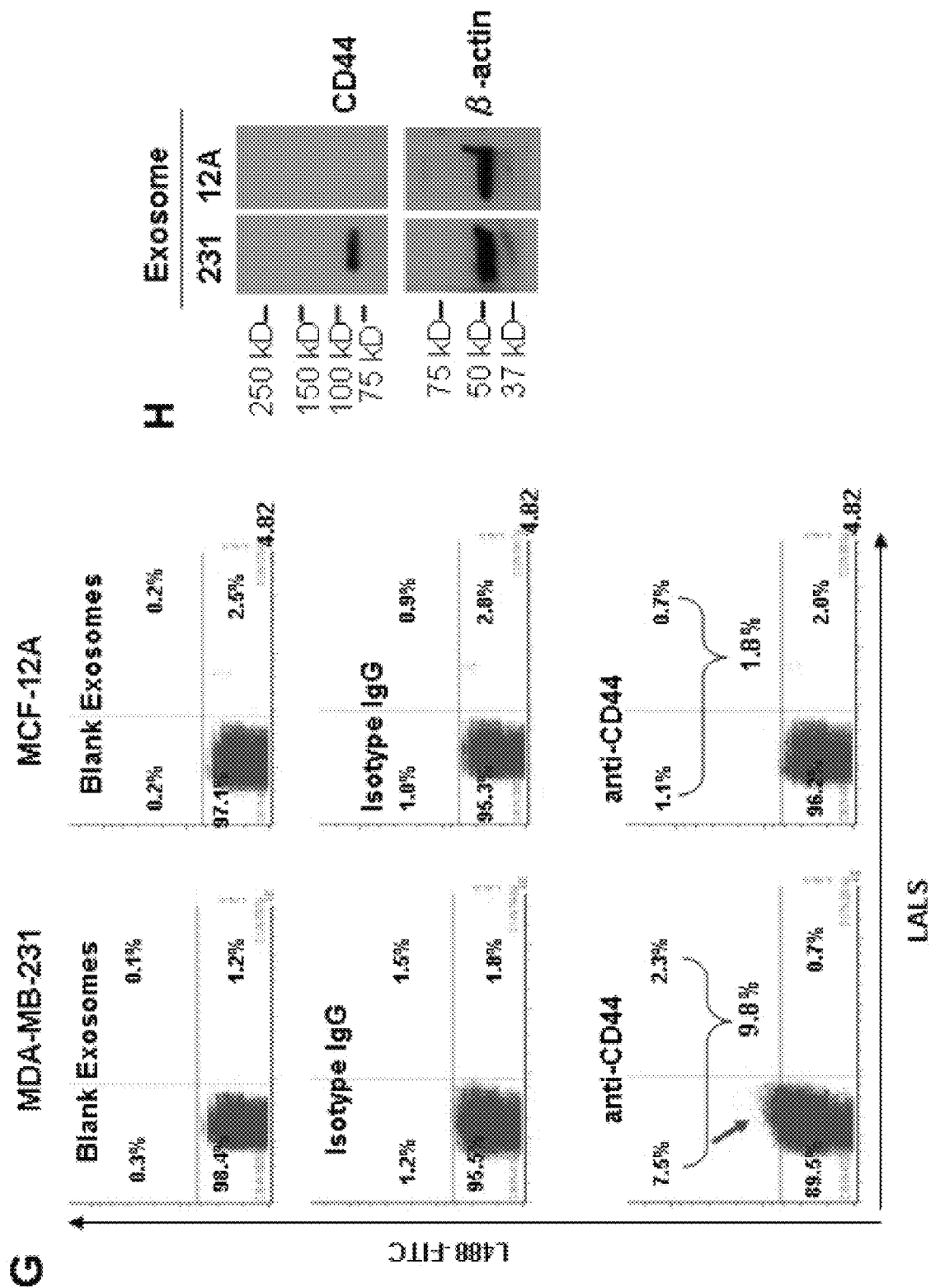

To profile individual circulating exosomes, we utilized the Apogee A50 Micro flow cytometer (MFC) that detects smaller particles with three light scatters: small angle light scatter (SALS), middle angle light scatter (MALS), and large angle light scatter (LALS)[31] (FIG. 2A) as well as fluorescent channels based on the laser(s) of choice. To minimize the background noise of PBS and the reference ApogeeMix beads shown at the default setting (FIG. 7A and the purple box in 7B), we then modified the settings to a higher threshold to run PBS alone (FIG. 7C) and the beads (FIG. 2B-C). We then evaluated the fluorescence and size features of the blood-derived unlabeled circulating exosomes using L488-FITC and LALS signals (FIG. 2D-E). Based on the comparison histograms in FIG. 2F, the size curve of the gated circulating exosomes in FIG. 2D (red rectangle) was found close to or largely overlapping with that of the 110 nm fluorescence beads gated in FIG. 2B (red rectangle).

Figures 7A, 7B, 7C, 7D:
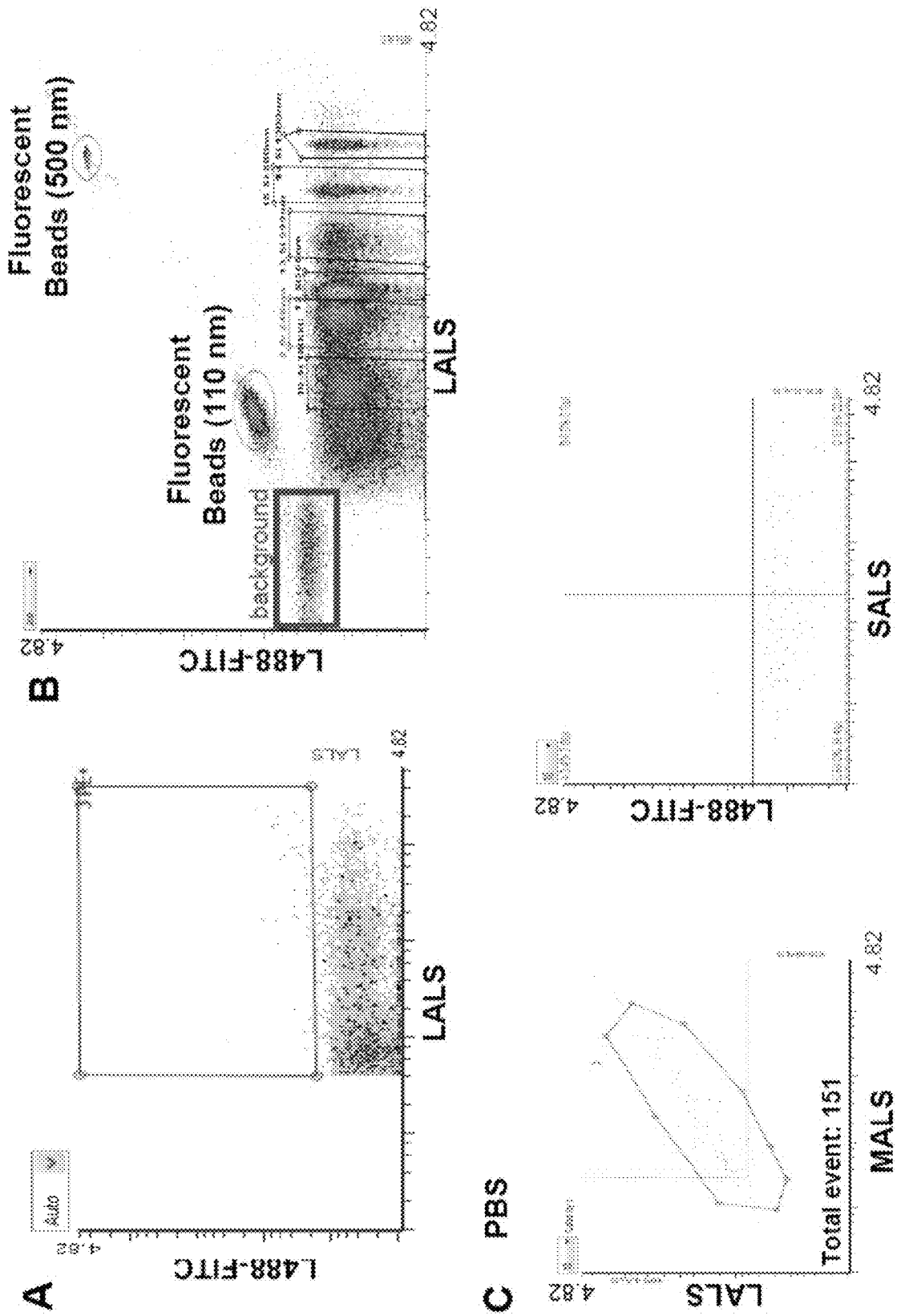
FIGS. 7A-7D. Exosome flow analysis optimizations. A-B. Background particles shown in PBS (A) and the reference beads solution (B) at the default setting of A50 MFC. The reference ApogeeMix beads is an aqueous mixture of 110 nm and 500 nm green fluorescent latex beads with refractive index (RI) η=1.59, and non-fluorescent silica (Si) beads with 180-1300 nm diameter and RI η=1.43. The RI of Si beads is closer to the RI of biological particles (RI of cells and EVs is 1.4). C-D. Analyses of PBS and antibodies using A50 MFC. C. PBS, used for exosome sample preparations, was run at high-threshold setting. Minimal particles in PBS were observed in multiple light scatter and fluorescence L488 channels. D. Cytogram of FITC-CD47 antibody as well as Isotope control FITC-IgG1 before and after centrifugation. Before staining exosomes, antibody bulk solutions were centrifuged at 14000×g for 1 h at 4° C. to remove particles or precipitates.
Figures 8A, 8B:
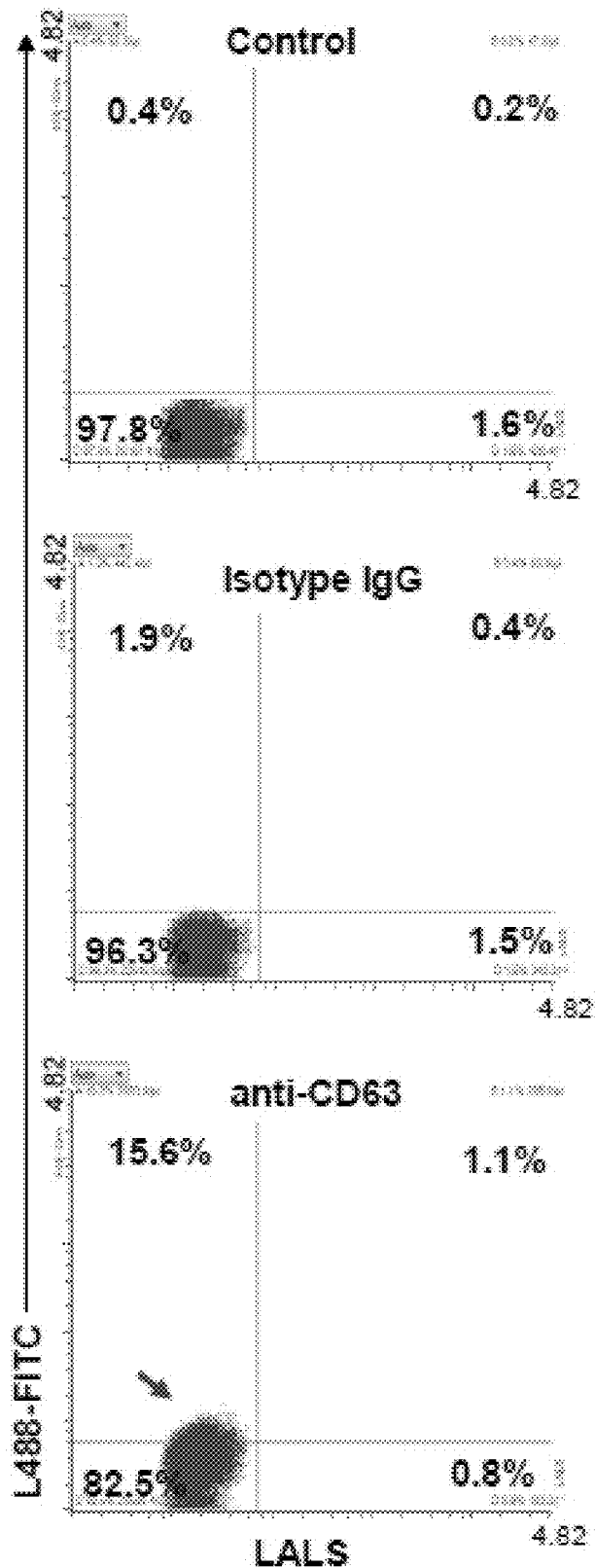
FIGS. 8A-8B. MFC analyses of exosomal CD63 and CD47. A. Detection of CD63 expression on exosomes derived from MDA-MB-231 cells by A50 MFC. Exosomes were stained with the FITC-conjugated mouse anti-human CD63 antibody, followed by dilution with PBS and then detected under Apogee MFC. FITC Isotype IgG staining or unstained were used as background controls. The expression of CD63 was detected (red arrow) in 15.6% of exosomes. B. Evaluation of the effect of total events counted on CD47 detection on circulating exosomes. Cytograms showing the expression of CD47 in 5000 and 10000 counted exosomes isolated from the blood of healthy control. Exosomes were stained with FITC-CD47 antibody, isotype control FITCIgG1, or unstained (control). Between the analyses with 5000 and 10000 counted events, similar % of CD47+ exosomes were observed in the upper two quadrants (Q1+Q4).
Figures 8A, 8B:
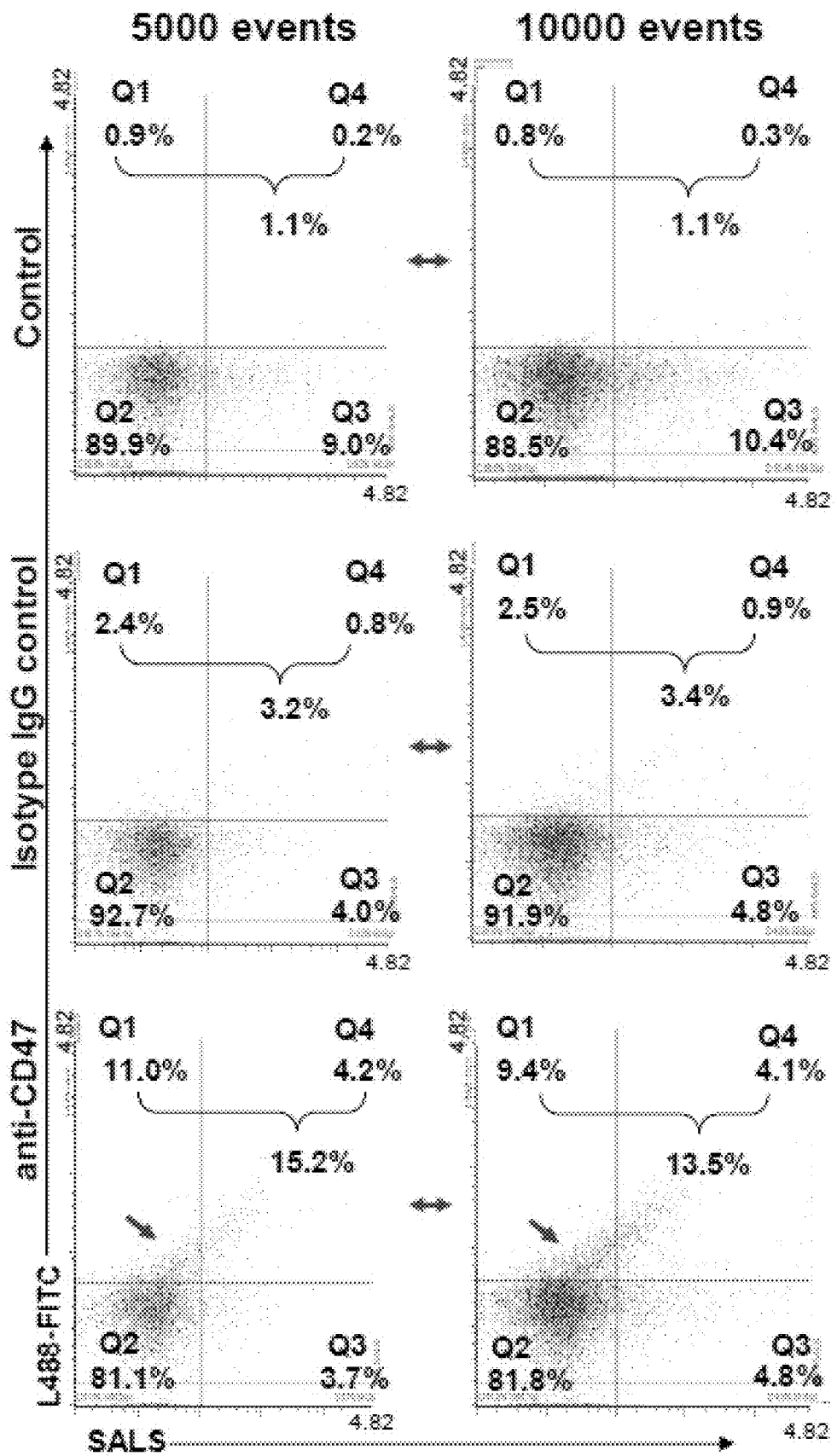

Using fluorophore-conjugated antibodies, we set out to measure expression levels of the exosomal surface marker CD63 and other cancer-related proteins shown in our mass spectrometry analyses of exosomes, such as CD44 and CD47. Prior to incubation or staining with the exosomes, the antibody solutions were centrifuged to eliminate any existing background particles (FIG. 7D). CD63 expression was detectable by MFC in the cell line-derived exosomes that served as a positive control (FIG. 8A). The differential expression of CD44 was detected by A50 MFC on the exosomes derived from MDA-MB-231 cells (mainly CD44 positive) and MCF-12A cells (mainly CD44-negative) (FIG. 2G), and consistently validated by CD44 immunoblotting of these exosomes (FIG. 2H).

We then optimized the detection procedure to measure CD47 and CD44 levels in the circulating exosomes from human blood (cancer patients n=60 and healthy controls n=60). A summary of the clinical characteristics of the breast cancer patients was provided in FIG. 23. For each sample, an aliquot of purified exosomes (based on a total protein of 2 µg) was incubated with a specific antibody, its isotype control, or a blank buffer control for 45 min at 4° C. to avoid aggregations. Upon 25-fold volume dilution, the exosomes were then immediately analyzed on MFC (4500 events collected).

Figures 3A, 3B, 3C, 3D, 3E, 3F:
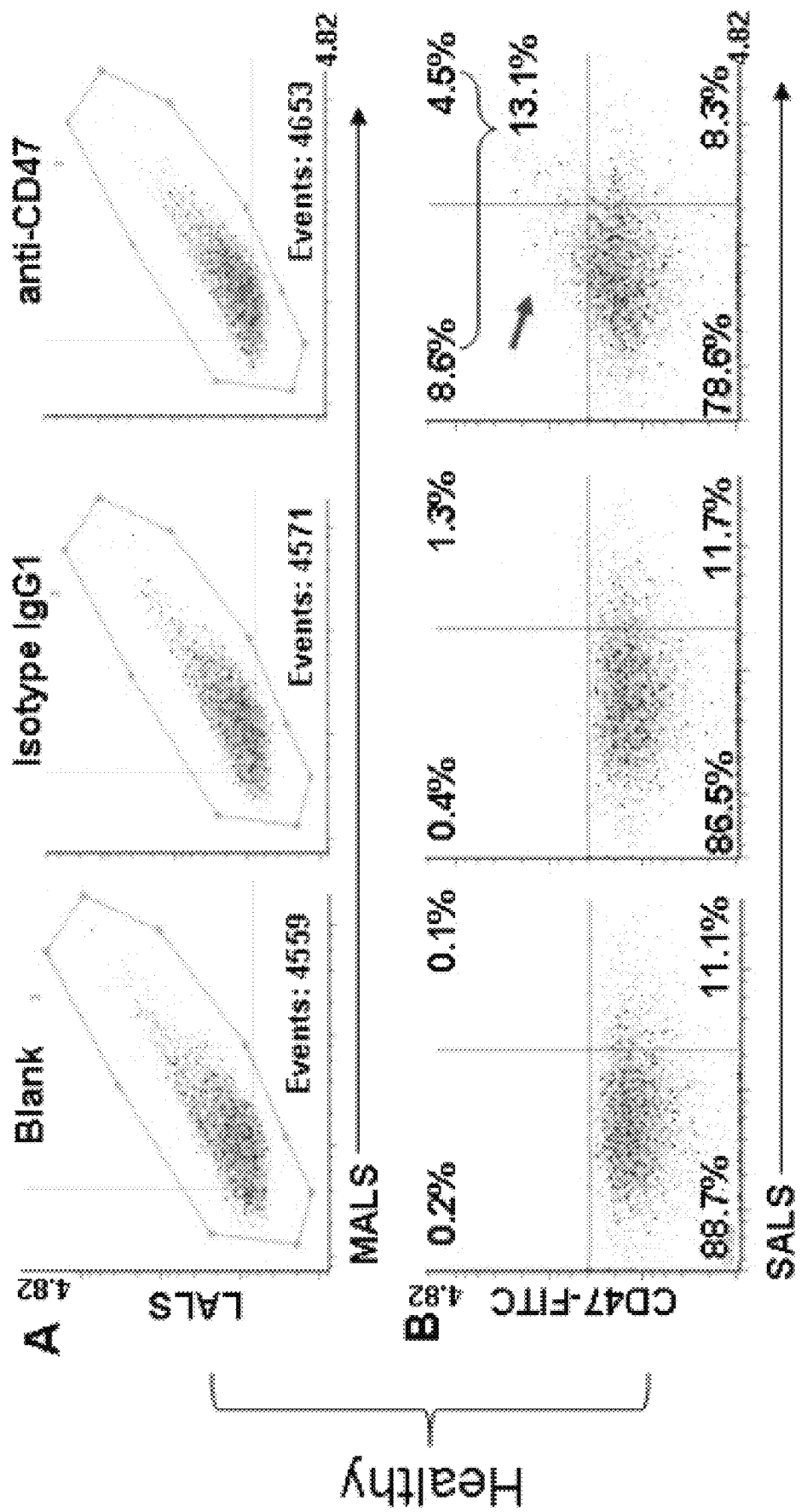
FIGS. 3A-3F. Detection of the surface protein CD47 in circulating exosomes and its correlation with breast cancer. A,C: Representative scattered plots showing MALS and LALS signals of the circulating exosomes isolated from the blood of healthy control and (A) breast cancer patients, (C) 4500 total events collected for each sample: unstained blank control, isotype IgG1, and anti-CD47. B,D: Representative cytograms showing differential expression of CD47 on the exosomes isolated from the blood of healthy control (B) or that of a breast cancer patient (D). Exosomes were stained with FITC-CD47 antibody or isotype control FITC-IgG1, or unstained (control). E. Comparison of MFC-analyzed CD47 expression levels on circulating exosome specimens isolated from the blood of healthy people (representative in B, n=60) and breast cancer patients (representative in D, n=60). Unpaired Student's t-test, p value<0.05. F. Expression of CD47 on circulating exosomes measured by the ELISA. Exosomes isolated from the blood of 40 healthy control and 50 breast cancer patients were treated with the anti-CD47 ELISA antibody. Unpaired Student's t-test, p value<0.01.
Figures 3A, 3B, 3C, 3D, 3E, 3F:
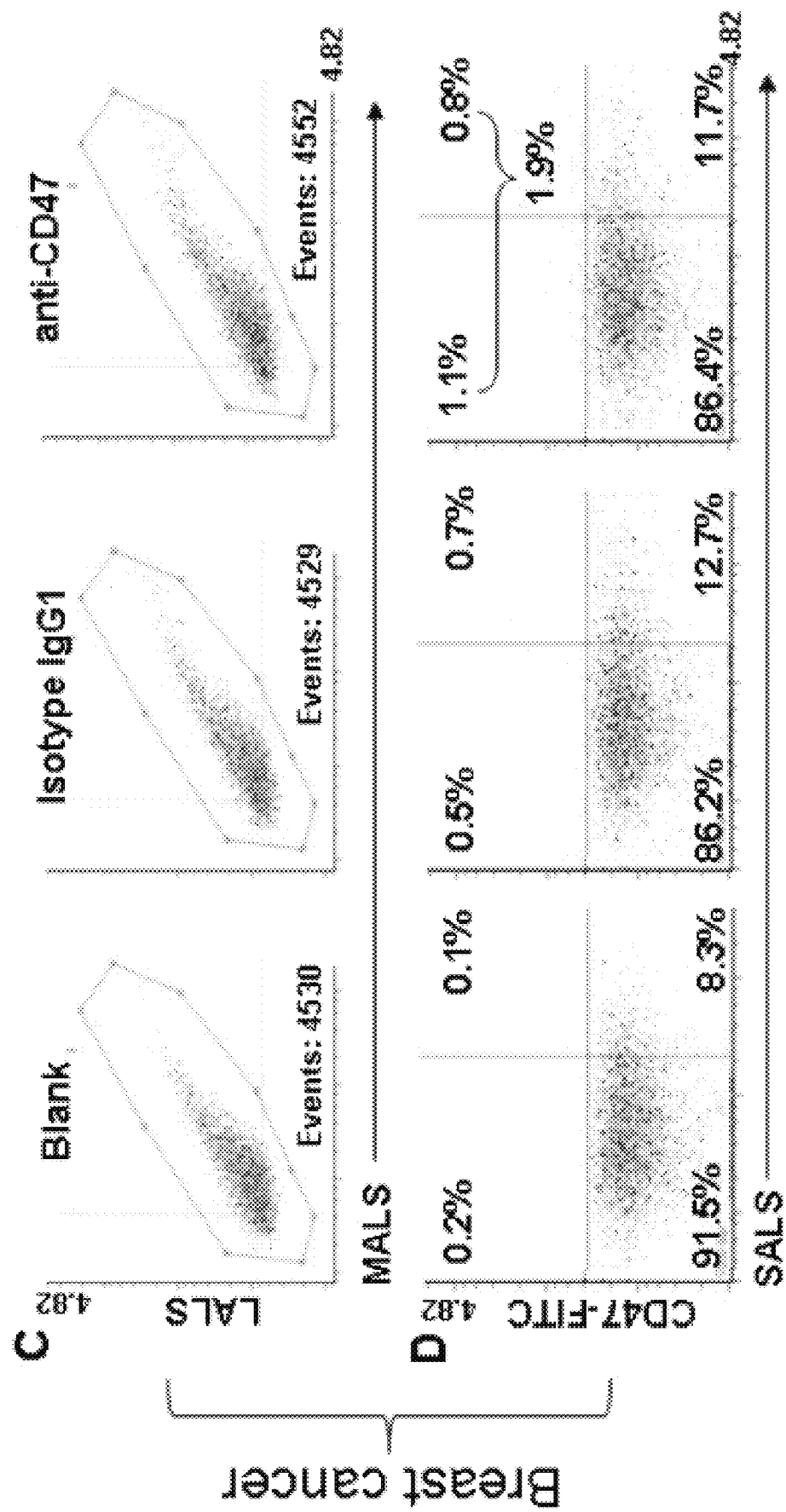
Figures 3A, 3B, 3C, 3D, 3E, 3F:
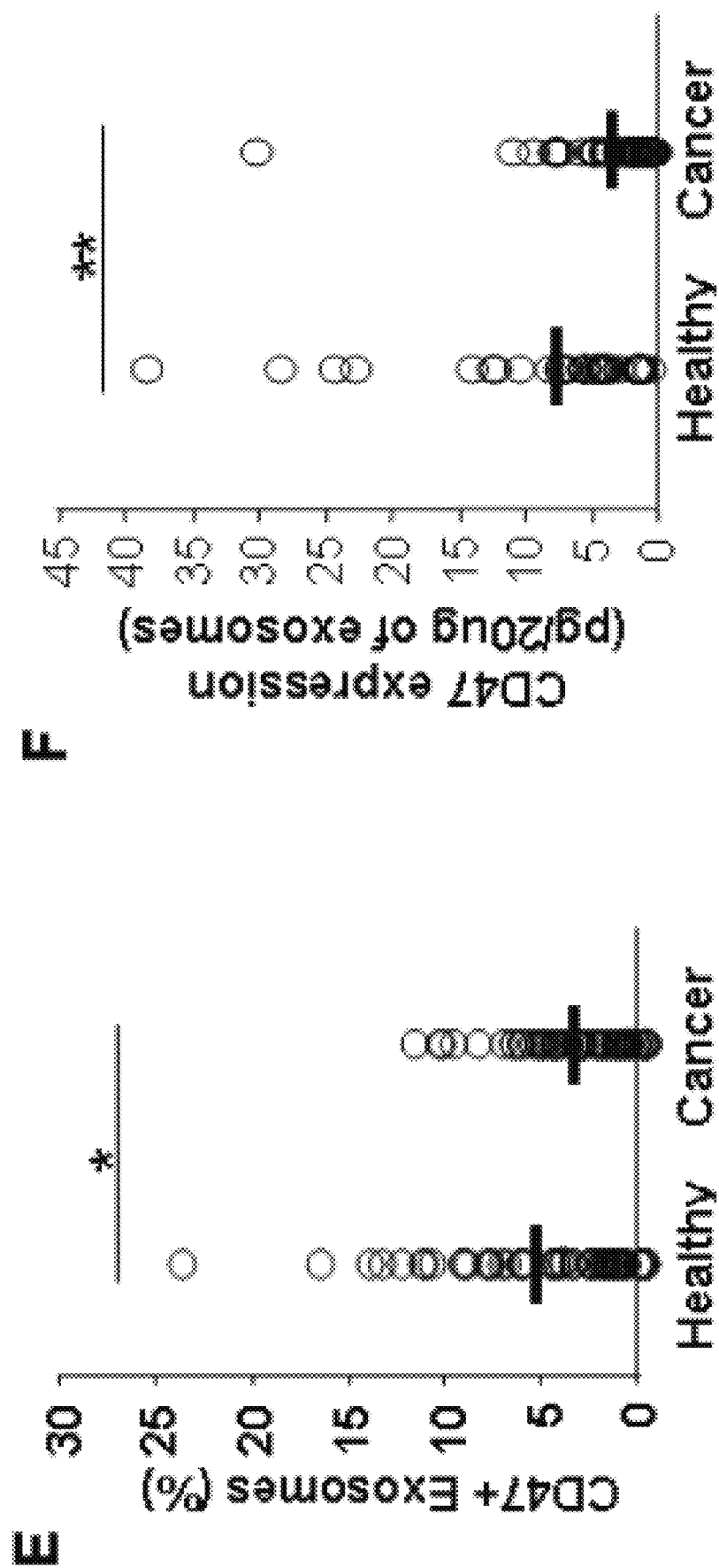
Figure 9:
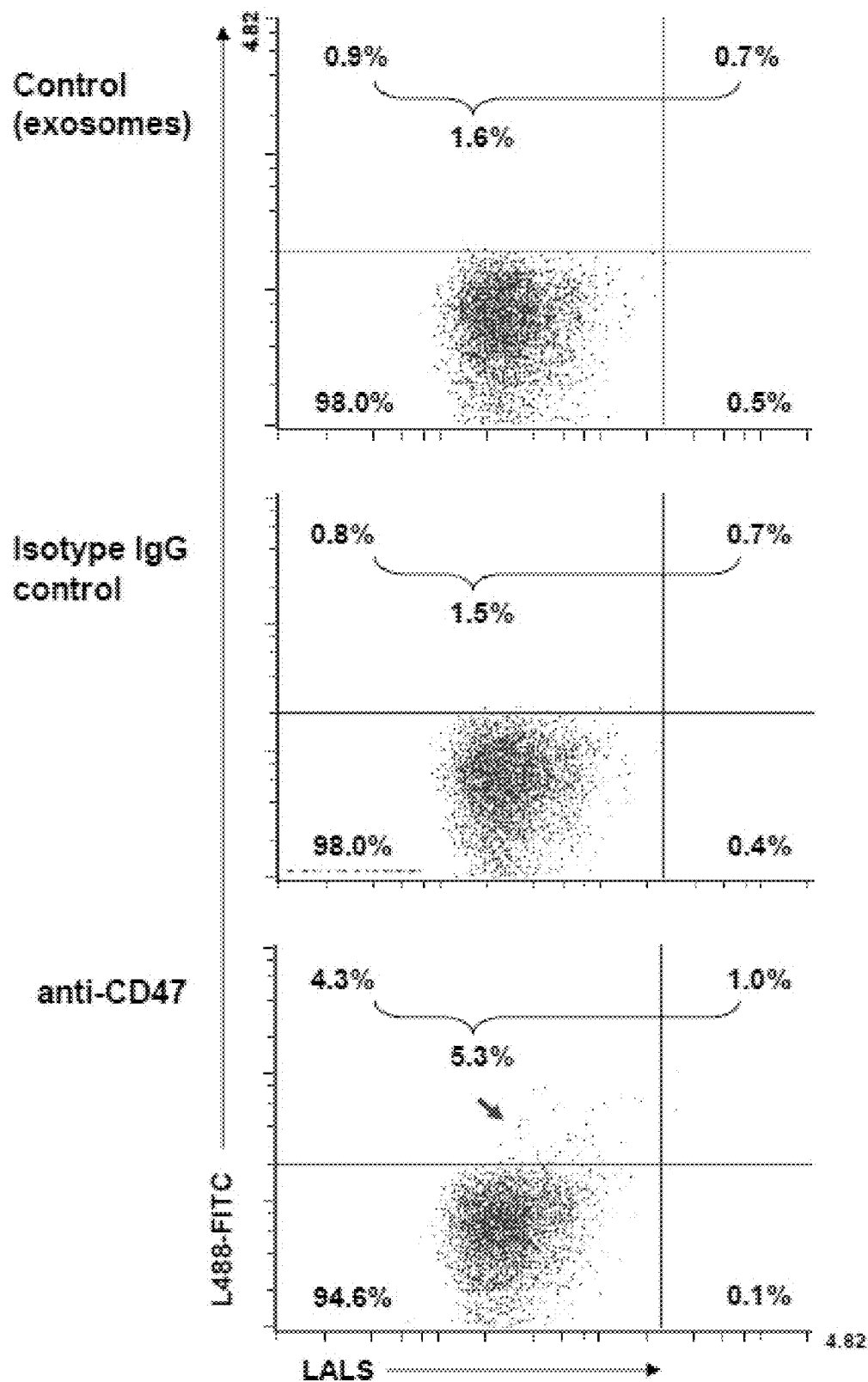
FIG. 9. Detection of CD47 expression on exosomes isolated from human serum (healthy) by using the exosome-isolation kit. Exosomes were stained with FITC-CD47 antibody or isotype control FITC-IgG1, or unstained (control) followed by detection under Apogee MFC.

The exosomes in the three staining conditions had similar profiles of MALS/LALS (FIGS. 3A and C). From the healthy control samples, CD47 expression was remarkably detected in ~10% of individual circulating exosomes whereas minimal CD47 expression (0.7%, after deducting the background signal) was shown in the circulating exosomes from breast cancer patients (FIGS. 3B and D). A significant difference of CD47 expression was observed between exosomes from cancer patients (n=60) versus exosomes from healthy control (n=60, p=0.037) (FIG. 3E). The exosomal CD47 expression profiles were similar between the analyses from 5,000 and 10,000 collected exosome counts (FIG. 8B). Furthermore, the expression of CD47 was detected on exosomes isolated from the human serum by using the exosome-isolation kit, but it required additional clean-up via ultracentrifugation in order to reduce the false-positive noise background for flow analyses (FIG. 9B).

Figures 10A, 10B:
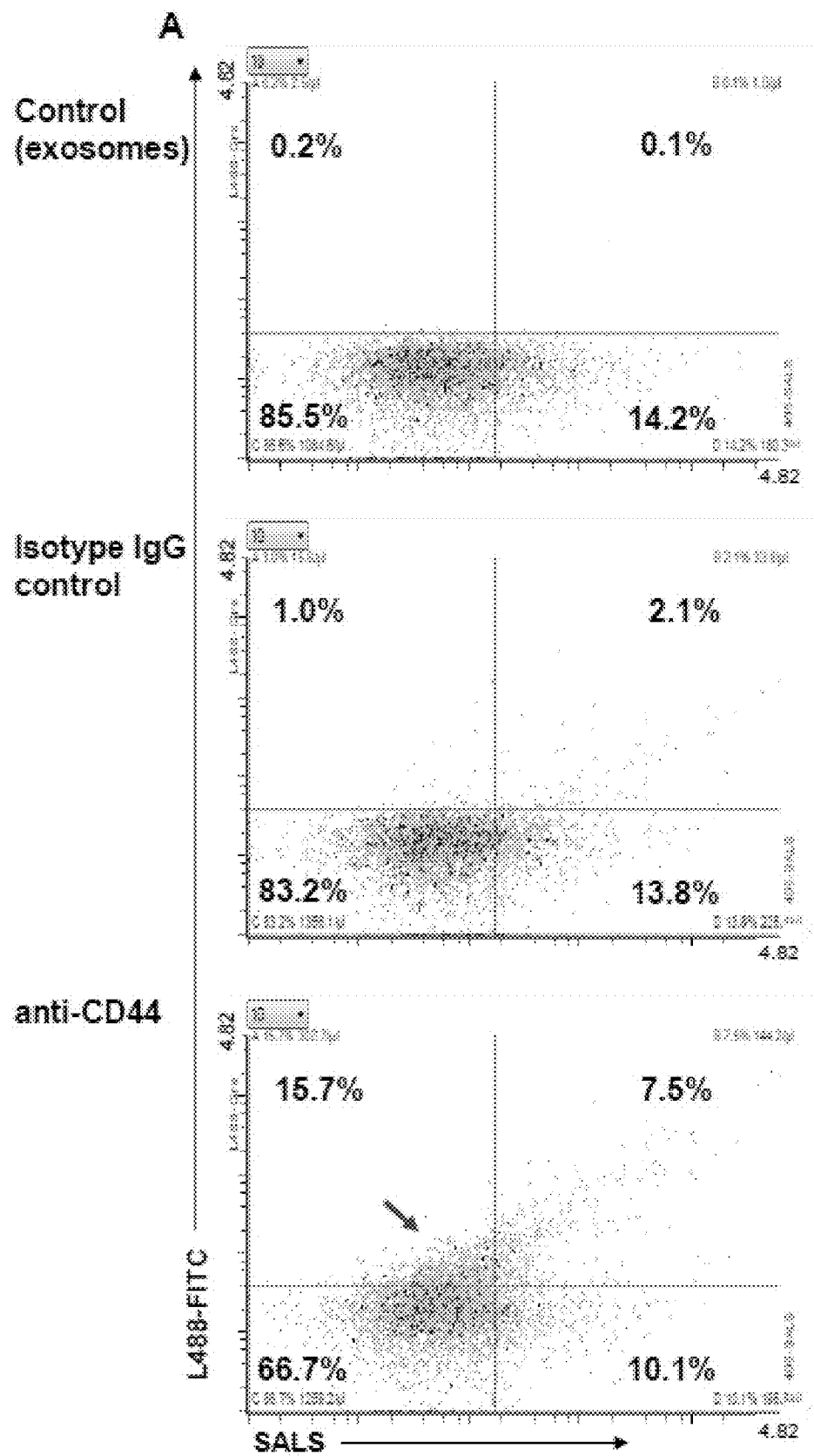
FIGS. 10A-10B. Detection of CD44 on circulating exosomes by MFC. A. Cytograms showing the expression of CD44 on exosomes isolated from the blood of a healthy control. Exosomes were stained with either FITC-CD44 antibody, isotype control FITC-IgG, or unstained (control). Compared to controls, about 20% CD44 positive exosomes were detected (red arrow). B. Comparison of the expression of CD44 in circulating exosomes isolated from the blood of fifteen healthy controls and twenty breast cancer patients. Statistical analysis was done by Unpaired Student's t-test. N.S.: non-significant.
Figures 10A, 10B:
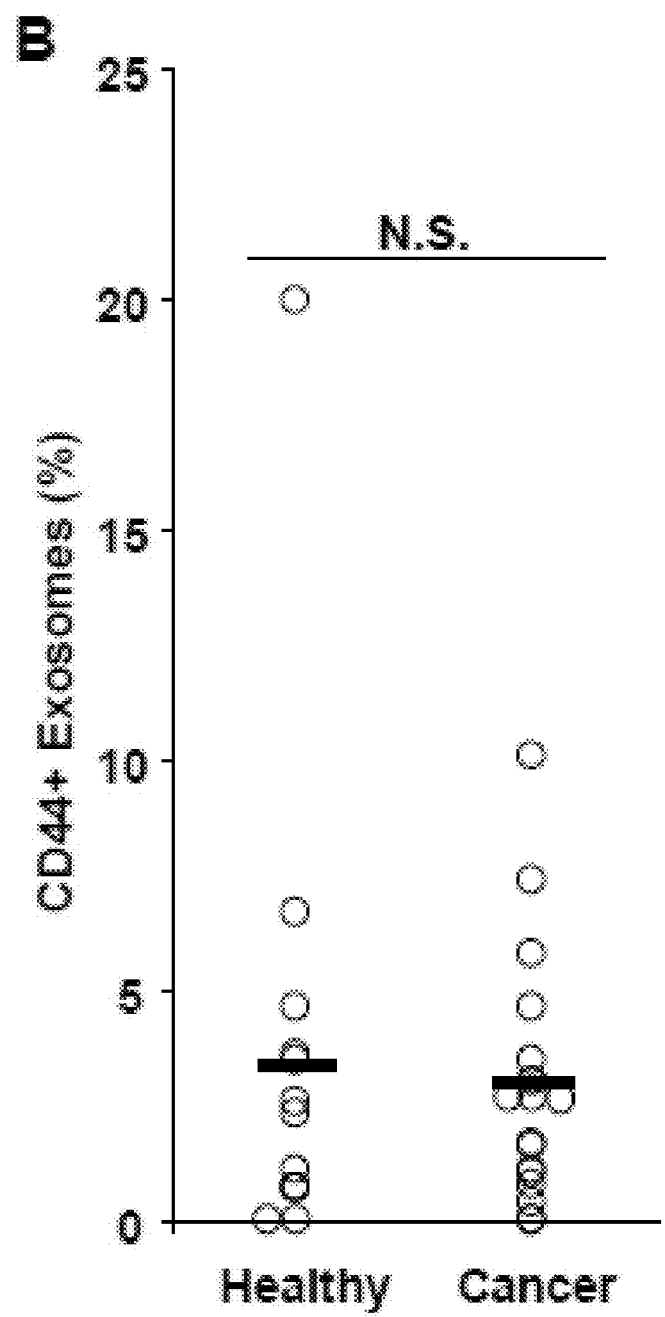

We further validated CD47 expression in exosomes using a second approach, CD47-ELISA which required a minimum of 20 µg proteins of collected exosomes. We also observed a significant difference of CD47 protein levels between two groups of exosome samples derived from healthy people and age-matched breast cancer patients (p=0.004) (FIG. 3F). In contrast to the differential CD47 expression profiles, we did not observe a significant difference of CD44 protein levels between the exosomes from the healthy control group and those from the breast cancer patients (FIG. 10A-B). These results suggest a great potential for single exosome profiling technology in discovering specific novel diagnostic biomarkers in cancer.

DISCUSSION

Due to improved ability to rapidly analyze small particles at an unprecedented sensitivity for fluorescent signals and extreme light scatter performance using three distinct angle ranges, the MFC is capable of measuring surface protein profiles of single exosomes isolated from cell culture or human blood. It may greatly improve high throughput, dynamic analyses of human body fluid-derived extracellular vesicles (such as exosomes and micro vesicles from blood and urine) and will expedite discoveries of novel diagnostic and prognostic biomarkers. The functional importance of differential CD47 expression detected in circulating exosomes from healthy versus cancer populations will be the subject of further study. The related molecular mechanisms contributing to this differential expression profile may involve differential rates of exosome production or exosome clearance.

In addition to proteins, nucleic acids and lipids in exosomes can also be analyzed after appropriate staining with suitable fluorescent reagents. Upon protocol optimization, it might also be possible to detect proteins in the lumen. In this study, we present a unique, sensitive, high throughput platform that can be applied to evaluate exosomes for clinical cancer diagnosis. Future studies can evaluate the potential of this method to characterize proteins in exosomes derived from other patient fluids, such as urine or saliva.

Methods

Human Studies:

All human blood studies were performed in compliance with the US Department of Health and Human Services and approved by The University Hospitals Case Medical Center (UHCMC) Institutional Review Board CASE 9114 (IRB number 01-15-35C) "The role of exosomes in breast cancer". Informed consent was obtained from all subjects when the blood was originally collected.

Cell Culture:

The human breast adenocarcinoma cells (MDA-MB-231) and breast epithelial cells (MCF-12A) were purchased from the American Type Culture Collection, ATCC (Manassas, Va., USA). Before culturing, the cells were tested for *mycoplasma* contamination. The cells were grown in Dulbecco's Modified Eagle's Medium (DMEM) supplemented with 5% (v/v) fetal bovine serum (FBS), 100 U/mL penicillin and 100 mg/mL streptomycin. MCF-12A cells were cultured in a mixture of DMEM and Ham's F12 medium (1:1 v/v) with 20 ng/ml human epidermal growth factor, 100 ng/ml cholera toxin, 0.01 mg/ml bovine insulin, 500 ng/ml hydrocortisone and 5% horse serum (v/v). To prepare the complete medium for cell culture, FBS or horse serum was exosome-depleted by ultracentrifugation at 100,000×g for 16 h at 4° C.

Isolation and Purification of Exosomes from Cells:

Exosomes were isolated from the cell culture supernatant, as described, previously. A scheme of the isolation protocol is given in FIG. 1A. Briefly, the cells were cultured as monolayers for 48 h in respective complete medium under an atmosphere of 5% $CO_2$ at 37° C. When cells reached a confluency of approximately 80% after 48 h, exosomes were isolated by differential centrifugation. First, the culture supernatant was centrifuged at 2,000×g for 10 min followed by 30 min centrifugation at 10,000×g to remove dead cells and cell debris. The clarified supernatant was ultracentrifuged for 2 h at 100,000×g using an SW28 rotor to pellet the exosomes. Exosomes were washed by resuspension in 30 mL of sterile PBS (Hyclone, Utah, USA), and pelleted by ultracentrifugation for 2 h at 100,000×g. The final exosome pellet was resuspended in 100 µl PBS and stored at −80° C.

Isolation and Purification of Exosomes from Human Blood:

Serum was derived from human blood (of healthy volunteers and/or of breast cancer patients) by centrifugation using Thermo IEC Centra-GP8R Centrifuge (Artisan Technology Group, Champaign, Ill., USA) at 3200 RPM for 15 min at 4° C. Blood was drawn from healthy population or age and sex-matched breast cancer patients before they were treated. The samples were then aliquoted and frozen at −80° C. until needed. Serum (0.5 ml) was diluted to 4 ml with PBS and centrifuged at 15,000×g for 30 min at 4° C. using TLA50.1 rotor to remove any remaining cells and debris followed by ultracentrifugation at 100000×g for 2 h at 4° C. to pellet the exosomes. The exosomes were resuspended in 2 ml of PBS and further pelleted by ultracentrifugation for 2 h at 100,000×g. Finally, the exosome pellet was resuspended in 50 µl of PBS and frozen at −80° C.

For isolation of exosomes from serum using the exosome-isolation kit (Thermo Fisher), serum was centrifuged at 2000×g for 30 minutes at 4° C. to remove the cell debris. The supernatant was collected and re-centrifuged at 10,000×g for 30 minutes to remove the apoptotic bodies. The supernatant was transferred to a new tube and incubated with the exosome-isolation kit (Cat #4478360, Life Technologies, Carlsbad, Calif., USA) for 30 min at 4° C. After incubation, the mixture was centrifuged at 10,000×g for 10 min at room temperature to get the exosome pellet. For further purification, exosomes were resuspended in 4 ml of PBS and pelleted by ultracentrifugation for 2 h at 100,000×g. Finally, the pellet was resuspended in PBS and frozen at −80° C.

Electron Microscopy:

Formvar/carbon-coated EM grids (Gilder Nickel Grid, Electron microscopy Sciences, PA, USA) were placed Formvar/carbon side down on top of the exosome sample drops for 10 minutes at room temperature. The grids were removed, blotted with filter paper and placed onto drops of freshly prepared 2.0% uranylacetate aqueous solution for one minute. The excess uranylacetate solution was removed, and air-dried. The images of the exosomes were captured using the FEI Tecnai™ Spirit (T12) transmission electron microscopes (Hillsboro, Oreg., USA) with a Gatan US4000 4k×4k charge coupled device (CCD) camera.

Size Distribution and Zeta-Potential of Exosomes:

The size and Zeta-potential of the exosomes were measured using ZetaView® nanoparticle tracking analyzer (Particle Metrix GmbH, Meerbusch, Germany).

Immunostaining:

Exosomes were mixed with 2% PFA (1:1, v/v in PBS) and placed on a coverslip for 20 min, followed by washing twice with PBS. Exosomes were blocked with 10% Normal Donkey Serum (Cat #017-000-121, Jackson Immunoresearch Labs Inc., West Grove, Pa., USA) for 30 min and washed with PBS. Following this, exosomes were treated with the mouse anti-human CD63 antibody (Cat # ab8219, Abcam, Cambridge, Mass., USA) at a concentration of 4 µg/ml for 20 min at room temperature and then washed with PBS. Finally, the exosomes were incubated with the Alexa 488 goat anti-mouse IgG (Cat # A11001, Invitrogen, Eugene, Oreg., USA) at a dilution of 1:200 for 20 min followed by washing with PBS, and fixed using ProLong® Gold Antifade Mountant (Cat # P10144, Carlsbad, Calif., USA). The treated exosomes were observed under a confocal microscope (DeltaVision Elite, GE Healthcare Life Sciences, PA, USA). Exosomes those were either untreated or treated only with Alexa 488 goat anti-mouse IgG served as background controls.

Rapid Micro Flow Cytometer Analysis of Exosomes:

Before treating the exosomes with the antibodies, the antibody solutions were centrifuged at 14000×g for 1 h at 4° C. to remove any aggregates. To detect surface proteins, exosomes (2 µg protein equivalent amount of exosomes in 20 µl of PBS) were blocked by using 1 µg of IgG from mouse serum (Cat #15381, Sigma, St. Louis, Mo., USA) for 10 min at 4° C. and incubated with 0.1 µg of FITC mouse anti-human CD47 (Cat #556045, BD Biosciences, San Jose, Calif., USA) for 45 min at 4° C. Consequently, the solution was diluted to 500 µL with PBS (Hyclone, Utah, USA). Finally, without any further washing, the samples were run on Apogee A50 Micro Flow Cytometer (MFC) (Apogee Flow Systems, Hertfordshire, UK), a dedicated FC specially developed for the analysis of nanoparticles (http://www.apogeeflow.com/products.php). Exosomes were left untreated or treated with 0.1 µg of FITC Mouse IgG1 κ Isotype Control (Cat #555748, BD Biosciences, San Jose, Calif., USA) was used as background control. Same protocol was followed for the detection of CD44 and CD63 on circulating exosomes and on exosomes from the cell culture supernatants, respectively. For the detection of CD44, after blocking, exosomes were treated with 0.1 µg of FITC mouse anti-human CD44 (Cat #555478, BD Biosciences, San Jose, Calif., USA) or with 0.1 µg of FITC Mouse IgG2b κ Isotype Control (Cat #555742, BD Biosciences, San Jose, Calif., USA) for 45 min at 4° C., followed by dilution to 500 µL with PBS. Similarly, for the detection of CD63, exosomes were incubated with 0.025 µg of FITC mouse anti-human CD63 (Cat #557288, BD Biosciences, San Jose, Calif., USA) or with 0.025 µg of FITC Mouse IgG1 κ Isotype Control (Cat #555748, BD Biosciences, San Jose, Calif., USA) for the same time period followed by dilution to 500 µL with PBS and analysis on Apogee MFC.

The reference ApogeeMix beads (Cat #1493), which are composed of an aqueous mixture of 110 nm and 500 nm green fluorescent latex beads, have refractive index η=1.59, and non-fluorescent silica (Si) beads with diameters 180 nm, 240 nm, 300 nm, 590 nm, 880 nm and 1300 nm diameter which have a refractive index η=1.43, (http://www.apogeeflow.com/products.php), were used to assess the performance of Apogee MFC, and to compare the size distribution of the exosomes. The PBS was run as a background control.

The reference beads and exosomes samples were run following two different settings in Apogee MFC. i). Regular default settings: sample flow rate 0.75 µl/min (total: 130 µl), numerical value set for Laser 405-LALS was 28, numerical value and voltage set for Laser 488-Gre were 26 and 525V, respectively. ii). High-threshold settings (minimizes the background noise): sample flow rate 1.5 µl/min (total: 130 µl), numerical values set for Thresholds & Lasers 405-SALS, 405-MALS, 405-LALS were 1, 31, 67, respectively; numerical value and voltage set for Laser 488-Gre were 1 and 560V, respectively.

Western Blot Analysis:

Cells and exosomes were lysed using lysis buffer. Protein lysates of exosomes (5 µg) were run on 4-20% Mini-PROTEIN TGX gel (Bio-Rad, Hercules, Calif., USA) and transferred to PVDF membrane. The blots were incubated separately either with mouse monoclonal anti-human CD63 antibody (Cat # ab8219, Abcam, Cambridge, Mass., USA) at a dilution of 1:10000, mouse monoclonal anti-human CD81 (Cat # NB100-65805, Novus Biologicals, Littleton, Colo., USA) at a dilution of 15:10000, rabbit polyclonal anti-human LAMP2B (Cat # ab18529, Abcam, Cambridge, Mass., USA) at a dilution of 1:5000, rabbit polyclonal anti-human Grp94 (Cat #2104P, Cell Signaling Technology, Danvers, Mass., USA) at a dilution of 5:10000, or with mouse monoclonal anti-human β-actin (Cat # ab8224, Abcam, Cambridge, Mass., USA) at a dilution of 2.5:10000 (in TBS buffer containing 2% BSA) at room temperature for 1 h followed by washing with TBS buffer. The blots were incubated with secondary antibody (horseradish peroxidase, HRP-conjugated goat anti-mouse (Cat # W402B) or goat anti-rabbit IgG (W401B) from Promega, Madison, Wis., USA) at a dilution of 1:10000 (2% Milk containing TBS buffer) for 1 h at room temperature. The blots were treated with the ECL kit according to the user manual, developed on X-ray film and finally observed using Konica Minolta SRX-101A Medical Film Processor (Konica Minolta Medical & Graphic Inc., (Shanghai, China).

Enzyme-Linked Immunosorbent Assay (ELISA) for CD47

The level of CD47 in the exosomes isolated from serum samples were determined using a DuoSet® ELISA assay kit for human CD47 (R&D Systems, Minneapolis, Minn., USA; Cat # DY4670-05) according to the manufacturer's instruction. Briefly, the flat-bottom polystyrene 96-well microplates were incubated and coated with the capture antibody overnight at room temperature. On the next day, the plate was washed, blocked with reagent diluent for 1 h at room temperature and washed again. The exosome samples (20 µg protein equivalent amount in 100 µl) or standards were then added for 2 h incubation at room temperature and washed prior to the secondary detection antibody incubation for 2 h at room temperature. After extensive washing, the wells were incubated with Sterptavidin-HRP for 20 min, after washing with the substrate solution for 20 min at room temperature in the dark. After adding the Stop solution, the optical density was measured spectrophotometrically at 450 nm and 560 nm using a microplate reader (GloMax®-Multi Detection System, Promega Corporation, Madison, Wis., USA). The concentration of CD47 in the samples was determined based on the standard calibration curve.

Statistical Analysis.

Statistical analysis was done by following Unpaired Student's t-test, Differences among the means were considered to be statistically significant at a p value of $P<0.05$ and $P<0.01$.

REFERENCES

Harding, C. V., Heuser, J. E. & Stahl, P. D. Exosomes: looking back three decades and into the future. *The Journal of cell biology* 200, 367-371, doi:10.1083/jcb.201212113 (2013).

van der Pol, E. et al. Optical and non-optical methods for detection and characterization of microparticles and exosomes. *Journal of thrombosis and haemostasis: JTH* 8, 2596-2607, doi:10.1111/j.1538-7836.2010.04074.x (2010).

Dragovic, R. A. et al. Sizing and phenotyping of cellular vesicles using Nanoparticle Tracking Analysis. *Nanomedicine: nanotechnology, biology, and medicine* 7, 780-788, doi:10.1016/j.nano.2011.04.003 (2011).

Valadi, H. et al. Exosome-mediated transfer of mRNAs and microRNAs is a novel mechanism of genetic exchange between cells. *Nature cell biology* 9, 654-659, doi:10.1038/ncb1596 (2007).

Schorey, J. S. & Bhatnagar, S. Exosome function: from tumor immunology to pathogen biology. *Traffic* 9, 871-881, doi:10.1111/j.1600-0854.2008.00734.x (2008).

Iero, M. et al. Tumour-released exosomes and their implications in cancer immunity. *Cell death and differentiation* 15, 80-88, doi:10.1038/sj.cdd.4402237 (2008).

Kahlert, C. & Kalluri, R. Exosomes in tumor microenvironment influence cancer progression and metastasis. *Journal of molecular medicine* 91, 431-437, doi:10.1007/500109-013-1020-6 (2013).

Hoshino, A. et al. Tumour exosome integrins determine organotropic metastasis. *Nature* 527, 329-335, doi:10.1038/nature15756 (2015).

Silva, J. et al. Analysis of exosome release and its prognostic value in human colorectal cancer. *Genes, chromosomes & cancer* 51, 409-418 (2012).

Melo, S. A. et al. Glypican-1 identifies cancer exosomes and detects early pancreatic cancer. *Nature* 523, 177-182, doi:10.1038/nature14581 (2015).

van der Pol, E. et al. Particle size distribution of exosomes and microvesicles determined by transmission electron microscopy, flow cytometry, nanoparticle tracking analysis, and resistive pulse sensing. *Journal of thrombosis and haemostasis: JTH* 12, 1182-1192, doi:10.1111/jth.12602 (2014).

Lacroix, R. et al. Standardization of platelet-derived microparticle enumeration by flow cytometry with calibrated beads: results of the International Society on Thrombosis and Haemostasis SSC Collaborative workshop. *Journal of thrombosis and haemostasis: JTH* 8, 2571-2574, doi:10.1111/j.1538-7836.2010.04047.x (2010).

Pospichalova, V. et al. Simplified protocol for flow cytometry analysis of fluorescently labeled exosomes and microvesicles using dedicated flow cytometer. *Journal of extracellular vesicles* 4, 25530, doi:10.3402/jev.v4.25530 (2015).

Al-Hajj, M., Wicha, M. S., Benito-Hernandez, A., Morrison, S. J. & Clarke, M. F. Prospective identification of tumorigenic breast cancer cells. *Proc Natl Acad Sci USA* 100, 3983-3988 (2003).

Godar, S. et al. Growth-inhibitory and tumor-suppressive functions of p53 depend on its repression of CD44 expression. *Cell* 134, 62-73, doi:10.1016/j.cell.2008.06.006 (2008).

Mani, S. A. et al. The epithelial-mesenchymal transition generates cells with properties of stem cells. *Cell* 133, 704-715, doi:10.1016/j.cell.2008.03.027 (2008).

Dalerba, P. et al. Phenotypic characterization of human colorectal cancer stem cells. *Proc Natl Acad Sci USA* 104, 10158-10163, doi:10.1073/pnas.0703478104 (2007).

Li, C. et al. Identification of pancreatic cancer stem cells. *Cancer research* 67, 1030-1037, doi:10.1158/0008-5472.CAN-06-2030(2007).

Prince, M. E. et al. Identification of a subpopulation of cells with cancer stem cell properties in head and neck squamous cell carcinoma. *Proc Natl Acad Sci USA* 104, 973-978, doi:10.1073/pnas.0610117104(2007).

Chao, M. P. et al. Anti-CD47 antibody synergizes with rituximab to promote phagocytosis and eradicate non-Hodgkin lymphoma. *Cell* 142, 699-713, doi:10.1016/j.cell.2010.07.044 (2010).

Chao, M. P. et al. Calreticulin is the dominant pro-phagocytic signal on multiple human cancers and is counterbalanced by CD47. *Sci Transl Med* 2, 63ra94, doi:10.1126/scitranslmed.3001375 (2010).

Chao, M. P., Weissman, I. L. & Majeti, R. The CD47-SIRPalpha pathway in cancer immune evasion and potential therapeutic implications. *Curr Opin Immunol* 24, 225-232, doi:10.1016/j.coi.2012.01.010 (2012).

Jaiswal, S. et al. CD47 is upregulated on circulating hematopoietic stem cells and leukemia cells to avoid phagocytosis. *Cell* 138, 271-285, doi:10.1016/j.cell.2009.05.046 (2009).

Majeti, R. et al. CD47 is an adverse prognostic factor and therapeutic antibody target on human acute myeloid leukemia stem cells. *Cell* 138, 286-299, doi:10.1016/j.cell.2009.05.045 (2009).

Chao, M. P., Majeti, R. & Weissman, I. L. Programmed cell removal: a new obstacle in the road to developing cancer. *Nature reviews. Cancer* 12, 58-67, doi:10.1038/nrc3171 (2012).

Kershaw, M. H. & Smyth, M. J. Immunology. Making macrophages eat cancer. *Science* 341, 41-42, doi:10.1126/science.1241716 (2013).

Thery, C., Amigorena, S., Raposo, G. & Clayton, A. Isolation and characterization of exosomes from cell culture supernatants and biological fluids. *Current protocols in cell biology/editorial board, Juan S. Bonifacino . . . [et al.]* Chapter 3, Unit 3 22, doi:10.1002/0471143030.cb0322530(2006).

Momen-Heravi, F. et al. Current methods for the isolation of extracellular vesicles. *Biological chemistry* 394, 1253-1262, doi:10.1515/hsz-2013-0141 (2013).

Lotvall, J. et al. Minimal experimental requirements for definition of extracellular vesicles and their functions: a position statement from the International Society for Extracellular Vesicles. *Journal of extracellular vesicles* 3, 26913, doi:10.3402/jev.v3.26913 (2014).

Simhadri, V. R. et al. Dendritic cells release HLA-B-associated transcript-3 positive exosomes to regulate natural killer function. *PloS one* 3, e3377, doi:10.1371/journal.pone.0003377 (2008).

Shapiro, H. M. *Practical flow cytometry.* 4th edn, (Wiley-Liss, 2003).

Each publication, patent, and patent publication cited in this disclosure is incorporated by reference herein in its entirety. The present disclosure is not intended to be limited to the foregoing examples, but encompasses all such modifications and variations as come within the scope of the appended claims.

Example 2: Engineered Exosomes as a Novel Nano Weapon Targeting Cancer Stem Cells (CSCs) for the Treatment of Breast Cancer and its Metastasis This Example demonstrates how to effectively control and target cancer stem cells for the treatment of cancer. Our previous studies have identified microRNAs (miRNAs), such as miR-200, miR206, and miR-30c, as one of the key factors that regulate breast cancer stem cells (BCSC) functions in tumor initiation, therapy resistance, and metastasis [3-6]. Based on the stability and small molecular weight (~6,000) of miRNAs, targeting CSCs with novel miRNA therapeutics is a promising approach for the treatment of breast cancer metastasis. This example demonstrates the use of bioengineered exosomes for the specific delivery of miRNAs or other chemotherapeutics to CSCs.

Exosomes remain stable natural products in the systemic circulation, therefore they hold a promising potential to overcome the off-targeting issues and toxicity of other traditional nanoparticles [12, 13]. More importantly, exosomes can be biologically engineered to express fused targeting peptides to the exosome surface protein LAMP2B, for targeted therapies [10]. Exosomes are also able to preferentially load and deliver RNAs to other cells [7, 9, 10].

This Example demonstrates the strategic selection a CSC marker for exosome-based targeting. Although CD44 is one the most characterized BCSC markers, it is also highly expressed on normal T cells. In addition to the BCSC markers CD44 and CD24, we recently found that CD47, a common CSC marker for both leukemia and solid tumors [14-16], is also highly expressed in BCSCs. CD47 protects CSCs from macrophage-induced phagocytosis through binding to its natural ligand SIRPα which is expressed on macrophages [14-16]. While the natural ligand displays relatively weak binding affinity to CD47, the mutated extracellular domain of SIRPα (mSIRPα) can increase the binding affinity and inhibit CD47 functions (See, Weiskopf K, Ring A M, Ho C C M, et al. Engineered SIRPα variants as immunotherapeutic adjuvants to anti-cancer antibodies. Science (New York, N.Y.). 2013; 341(6141):10.1126/science.1238856. doi:10.1126/science.1238856., incorporated by reference in its entirety).

In this example, we engineered exosomes to express the fusion product LAMP2B-mSIRPα (XPepα, FIG. 12), able to load and deliver miRNA therapeutics to CD47$^+$ CSCs. This strategy utilizes the mutated version of the single domain SIRPα, which has 50,000 times improved binding affinity to CD47 compared to the wild-type. The SIRPα domain allows for targeting of CSCs while the LAMP2B domain localizes the fusion peptide to the exosome membrane during exosome production. The bioengineered exosomes can be loaded with therapeutic miRNAs (miR-200, miR-30c, miR206) or chemotherapeutics to specifically and effectively block the function of BCSCs. Through the development of bioengineered exosomes that target breast CSCs, we can use such exosomes in patient-derived breast cancer metastasis models in vivo through inhibiting metastasis as well as in improving the life span of breast cancer patients in the clinics. Collectively, CSC targeted exosome-based nanomedicine is an innovative and effective tool for the treatment of breast cancer clinically.

Results

Figures 12A, 12B, 12C:
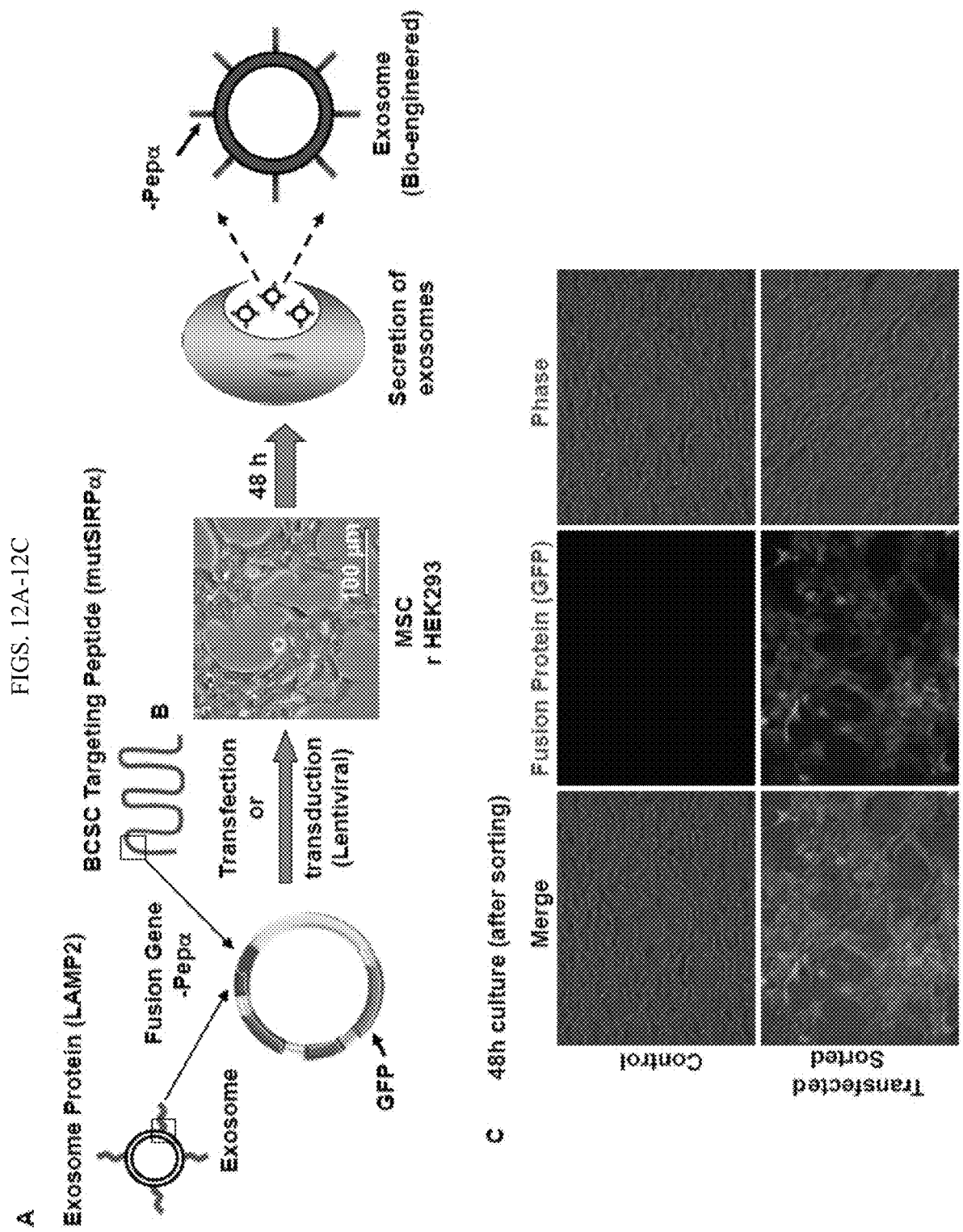
FIGS. 12A-12C is a depiction of one embodiment of the present disclosure describing the design and synthesis of bio-engineered exosomes targeting CD47+ BCSCs. A. Structure of fusion gene (XPepα) in a lentiviral vector tagged with Luc2-eGFP. The BCSC targeted fusion gene XPepα is comprised of the transmembrane and cytoplasmic tail of exosome specific peptide Lamp 2B which extracellular domain was replaced by mutant SIRPα extracellular domain (See SEQ ID NO:2, FIG. 25). B. Basic principle showing the transfection and lentiviral based transduction from HEK293FT or MSC cells for the biogenesis of engineered exosomes. C. Culture of transfected (green) cells for 48 h in exosome-depleted media to synthesize the bio-engineered exosomes.
Figures 13A, 13B, 13C, 13D, 13E:
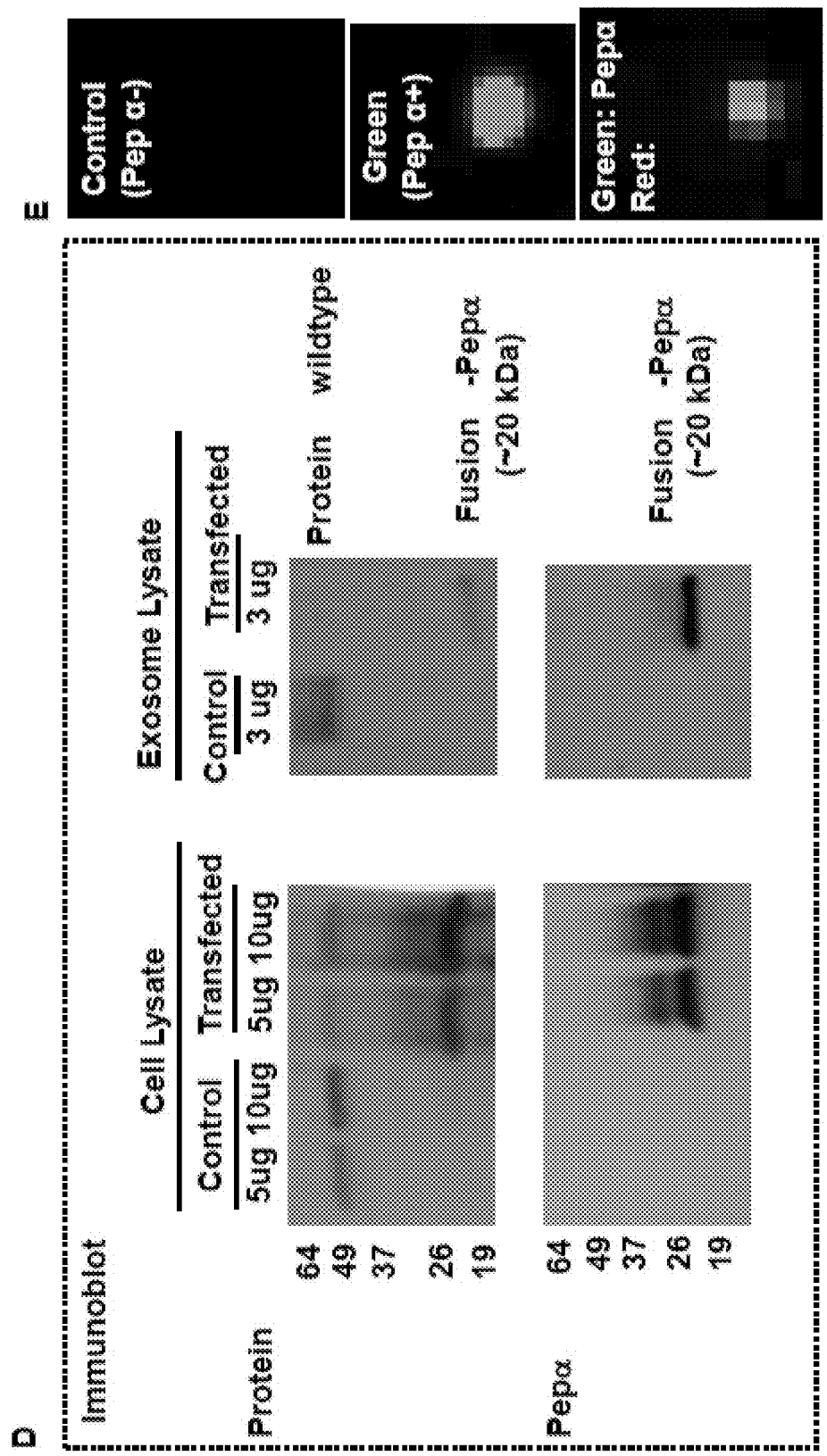
FIGS. 13A-13E demonstrates the exosome isolation, purification and characterization of bioengineered exosomes. A. Flow chart representing the isolation and purification of exosomes from the cell culture supernatant. B. ZetaView measurement of the size distribution of reference Polystyrene beads (60 nm, 200 nm) and HEK293FT cell-derived exosomes. C. Expression of Protein X (50 kDa), CD63 (43 kDa) in isolated exosomes observed by western blotting, β-actin (42 kDa) serves as background control. D. Evaluation of the expression of Protein X (50 kDa), and fusion protein XPepα (20 kDa) in control (untransfected) as well as fusion gene transfected HEK293FT cells and their secreted exosomes observed by western blotting. The expression of XPepα was observed only in exosomes secreted by the transfected cells, as compared to control. E. Immunofluorescence assay showing the expression of fusion protein XPepα (green) and exosomal protein X on the bioengineered exosome.

Development and Characterization of Bio-Engineered Exosomes for Targeting BCSCs In Vitro A lentiviral vector that expresses the fused LAMP2B-mSIRPα (XPepα) along with a Luc2-eGFP reporter gene was cloned (FIG. 12A-B). We utilized HEK293FT cell-produced lentiviruses to transduce HEK293FT or mesenchymal stromal cells (MSCs) cells followed by sorting and culture in exosome-depleted medium for 48 h (FIG. 12C) for the production of exosomes. Exosomes from cell culture supernatant were isolated and purified following differential ultracentrifugation method (FIG. 13A). The mean diameter of the isolated exosomes was found ~80 nm (range 40-120 nm) as measured by the ZetaView nanoparticle analyzer (FIG. 13B). Size of the reference polystyrene beads (60 nm, 200 nm) was found ~65 nm and ~185 nm, respectively. The immunoblotting analysis confirmed the expression of exosome specific markers ProteinX and CD63 (FIG. 13C) in the exosome lysate (3 µg protein). Furthermore, we performed immunoblotting assay using the cell and exosome lysates (control and transfected) where the expression of wildtype Protein X was mostly found in the lysates of control cells and its secreted exosomes (FIG. 13D). On the other hand, the expression of fusion Protein XPepα was found only in the lysates of transfected cells and its secreted exosomes (bioengineered) (FIG. 13D). Moreover, the expression of XPepα (green) along with wildtype Protein X (red) were confirmed on the surface of bioengineered exosomes by immunofluorescence assay (FIG. 13E).

Targeting and Internalization of Bioengineered Exosomes (XPepα+) into BCSCs

Figure 14A:
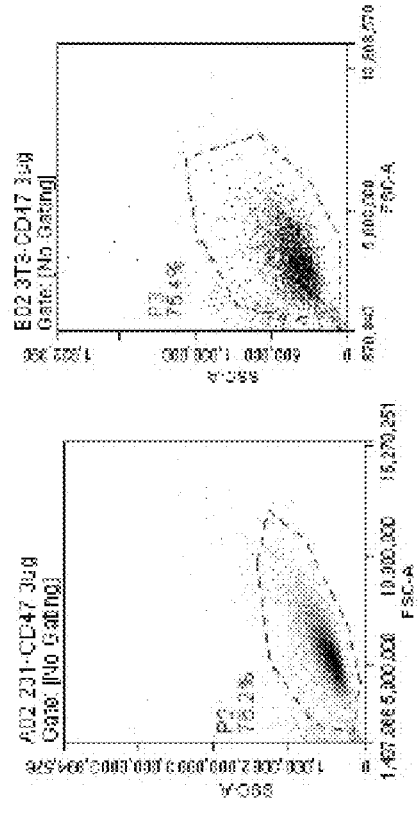
FIGS. 14A-14C demonstrate the ability to load and target bioengineered exosomes. A. Expression of CD47 in BCSCs, no CD47 was detected in NIH3T3 cells. B. Specific uptake of bio-engineered exosomes (XPepα+) by CD44+CD47+ BCSCs. BCSCs show higher cellular uptake shift (red line, left panel) as compared to NIH3T3 cells observed by flow cytometer. C. Qualitative analysis showing a substantial amount of bio-engineered exosomes (XPepα+) internalization into BCSCs over the regular exosomes (XPepα−), indicating the specific targeting of CD44+CD47+ BCSCs by Xpepα+ bio-engineered exosomes.
Figure 14B:
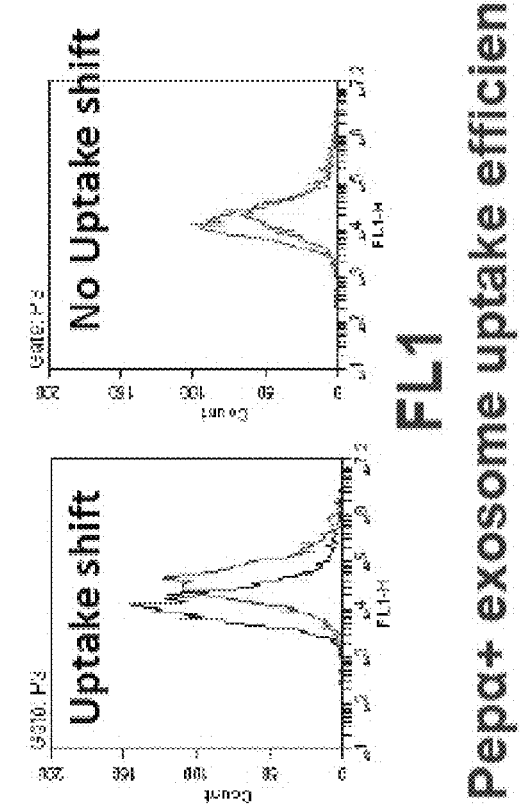
Figure 14C:
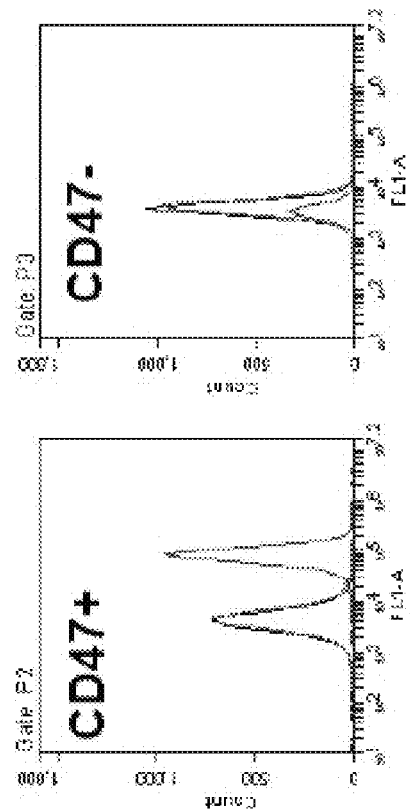
Figures 14A, 14B, 14C:
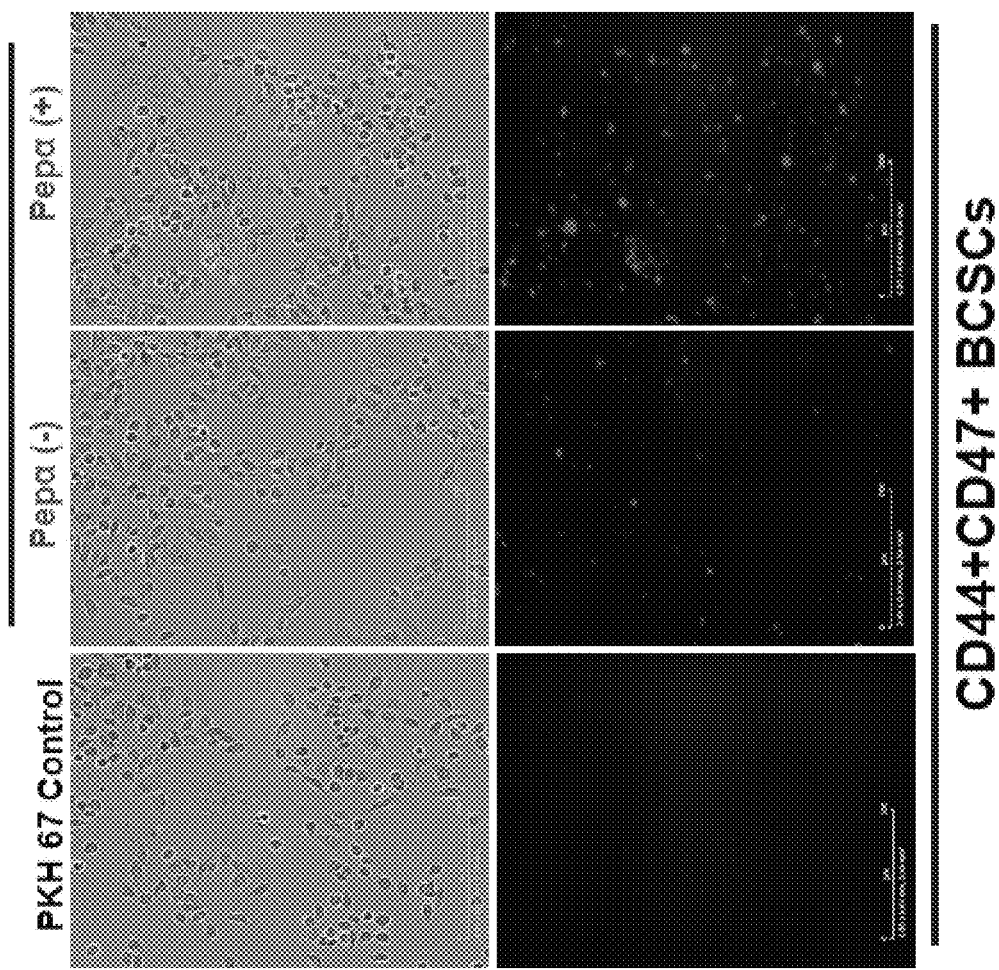

The internalization efficiency of the prepared bioengineered exosomes was evaluated using two different cell lines BCSCs and NIH3T3, where CD47 expression was found in BCSCs but not in the NIH3T3 cells (FIG. 14A). The bioengineered exosomes were labeled with PKH67 green dye followed by incubation with BCSCs and NIH3T3 cells. Based on flow cytometry analyses, a specific cellular uptake shift of bioengineered exosomes was observed in BCSCs as compared to that observed in NIH3T3 cells (FIG. 14B). Furthermore, bioengineered exosomes resulted in strong fluorescence signals inside the BCBSCs as compared to the regular exosomes (FIG. 14C), indicating that bioengineered exosomes was efficiently recognized and internalized by BCSCs. This result indicated the specific targeting of BCSCs by the bioengineered exosomes.

Cellular Internalization Pathway of Bioengineered Exosomes

Figures 15A, 15B:
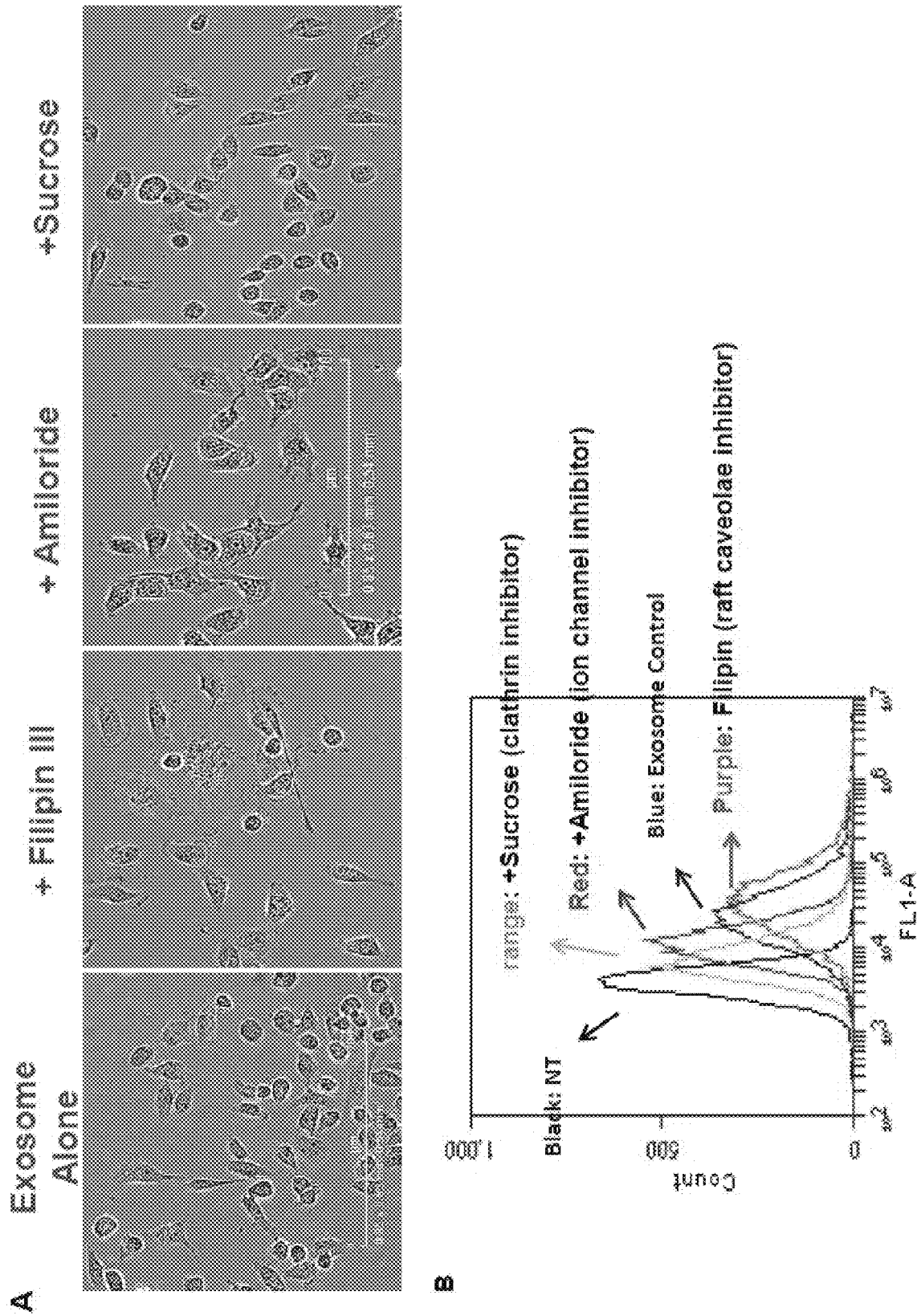
FIGS. 15A-15B demonstrate the mechanism of internalization of bio-engineered exosomes (XPepα+) into CD44+ CD47+ BCSCs. BCSCs were treated with different inhibitors to specifically inhibit different endocytosis routes. Both of the qualitative by confocal microscope (A) and quantitative by flow cytometry (B) analyses indicated that the cellular uptake of XPepα+ exosomes was inhibited by Amiloride and Sucrose, indicating that the endocytosis of XPepα+ Exosomes is dependent on clathrin and Na(+)/H(+) exchange.

The mode of cellular internalization of the bioengineered exosomes was examined by using different endocytic pathway inhibitors. BCSCs were pretreated with different inhibitors including sucrose (inhibitor of clathrin-mediated endocytosis), amiloride (inhibitor of macropinocytosis), and filipin (inhibitor of caveolar uptake pathway), followed by the incubation with PKH67 labeled exosomes. The cellular internalization of exosomes was inhibited by amiloride as well as by sucrose as indicated by microscopic observation as we all flow cytometry (FIG. 15A-B), demonstrating that the developed bioengineered exosomes are internalized into BCSCs by macropinocytosis and clathrin-mediated endocytosis pathways.

Biodistribution and Tumor Accumulation Study of Bioengineered Exosomes

Figure 16:
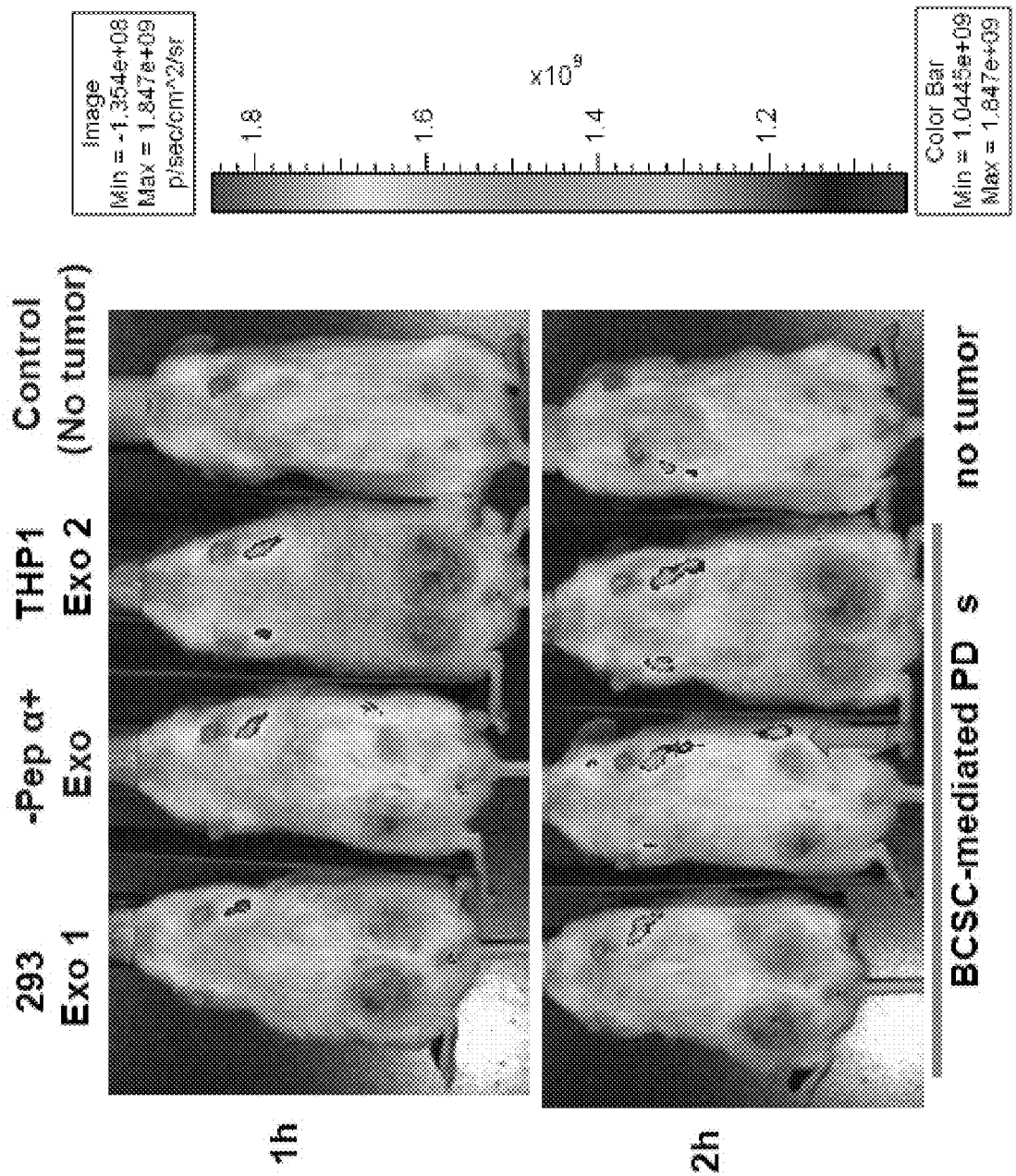
FIG. 16 demonstrates in vivo biodistribution and targeting CD44+CD47+ BCSCs by XPepα+ bio-engineered exosomes. Regular exosomes (Xpepα−) from HEK293FT, THP1 cells as well as bio-engineered exosomes (XPepα+) were labeled with PKH67 dye and injected into patient-tumor-derived xenograft (M1) mice via tail vein. IVIS images of mice were captured at 1 h and 2 h post-injection of exosomes. Compared to other exosomes, bio-engineered exosomes show its promise to home to specific cancer cells.

After in vitro characterization, the biodistribution, including the intra-tumoral accumulation of bioengineered, was evaluated in mice bearing the human-in-mouse metastatic breast tumors. In this regard, control exosomes (from HEK293FT, THP1 cells) as well as bioengineered exosomes were labeled with PKH67 green dye and were injected into mice via the tail vein. Compared to the control exosomes, only the bioengineered exosomes show its promise to accumulate into the tumors (FIG. 16), indicating the possibility of homing and targeting of BCSCs by the bioengineered exosomes.

Loading of miRNA into Bio-Engineered Exosomes

Figure 17:
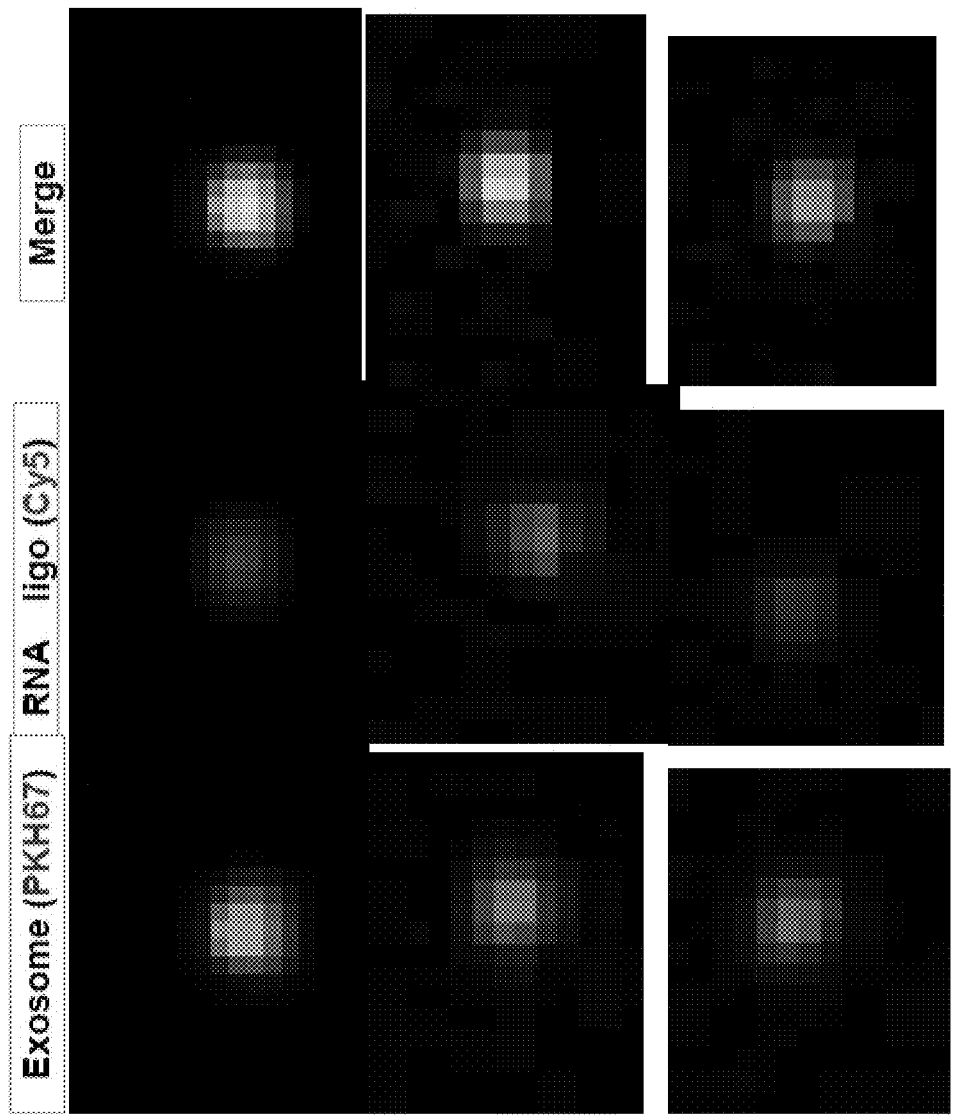
FIG. 17 demonstrates loading of RNA oligo into bio-engineered exosomes. Cy5 labeled RNA oligo (red) was loaded into exosomes by electroporation in presence of Bio-Rad electroporation buffer. The RNA loaded exosomes were labeled with PKH67 dye (green). The co-localization of green and red colors indicated successful loading of RNA into exosomes.

Electroporation has been used to load RNA into bioengineered exosomes (FIG. 17). Exosomes (3 µg protein equivalent amount) were mixed with cy5 labeled RNA oligo (0.77 µg) and electroporation was performed in 10 µl electroporation buffer (Bio-Rad). The RNA loaded exosomes were labeled with PKH67 dye (green). The co-localization of green and red colors indicated successful loading of RNA into exosomes. We expect that miR-30c, as a potential tumor suppressing therapeutic, will be efficiently loaded into bioengineered exosomes and specifically delivered to BCSCs.

The therapeutic effect of the exosomes are to be evaluated by observing the inhibition of tumor metastasis via selective inhibition of the function of BCSCs present either in the breast tumor tissues or in the systemic circulation. We expect that miR-30c-exosomes will have a great therapeutic effect on breast cancer metastasis compared to the scramble-exosome control or negative-treatment control.

Significance

BCSCs play an important role in generating breast tumors through the processes of self-renewal and differentiation into multiple cell types. In the solid tumor tissues, BCSCs remain a distinct population that can cause relapse and metastasis of tumor cells. By selectively targeting BCSCs, it would be possible to treat patients with aggressive, non-resectable tumors, as well as preventing patients from metastasizing. Therefore, the development of BCSC targeted exosome-based therapy holds great promise for its implication in clinics, such as the improvement of survival and quality of life for cancer patients, especially those with metastasis.

REFERENCES FROM EXAMPLE 2

1. Liu, H., et al., Cancer stem cells from human breast tumors are involved in spontaneous metastases in orthotopic mouse models. Proc Natl Acad Sci USA, 2010. 107(42): p. 18115-20.
2. Al-Hajj, M., et al., Prospective identification of tumorigenic breast cancer cells. Proc Natl Acad Sci USA, 2003. 100(7): p. 3983-8.
3. Bockhorn, J., et al., MicroRNA-30c inhibits human breast tumour chemotherapy resistance by regulating TWF1 and IL-11. Nat Commun, 2013. 4: p. 1393.
4. Bockhorn, J., et al., MicroRNA-30c targets cytoskeleton genes involved in breast cancer cell invasion. Breast Cancer Res Treat, 2013. 137(2): p. 373-82.
5. Liu, H., MicroRNAs in breast cancer initiation and progression. Cell Mol Life Sci, 2012.
6. Shimono, Y., et al., Downregulation of miRNA-200c links breast cancer stem cells with normal stem cells. Cell, 2009. 138(3): p. 592-603.
7. Valadi, H., et al., Exosome-mediated transfer of mRNAs and microRNAs is a novel mechanism of genetic exchange between cells. Nat Cell Biol, 2007. 9(6): p. 654-9.
8. Harding, C. V., J. E. Heuser, and P. D. Stahl, Exosomes: looking back three decades and into the future. J Cell Biol, 2013. 200(4): p. 367-71.
9. Skog, J., et al., Glioblastoma microvesicles transport RNA and proteins that promote tumour growth and provide diagnostic biomarkers. Nat Cell Biol, 2008. 10(12): p. 1470-6.
10. Alvarez-Erviti, L., et al., Delivery of siRNA to the mouse brain by systemic injection of targeted exosomes. Nat Biotechnol, 2011. 29(4): p. 341-5.
11. Verweij, F. J., et al., LMP1 association with CD63 in endosomes and secretion via exosomes limits constitutive NF-kappaB activation. EMBO J, 2011. 30(11): p. 2115-29.
12. Ruoslahti, E., S. N. Bhatia, and M. J. Sailor, Targeting of drugs and nanoparticles to tumors. J Cell Biol, 2010. 188(6): p. 759-68.
13. Zhang, L., et al., Nanoparticles in medicine: therapeutic applications and developments. Clin Pharmacol Ther, 2008. 83(5): p. 761-9.
14. Chao, M. P., et al., Extranodal dissemination of non-Hodgkin lymphoma requires CD47 and is inhibited by anti-CD47 antibody therapy. Blood, 2011. 118(18): p. 4890-901.
15. Majeti, R., et al., CD47 is an adverse prognostic factor and therapeutic antibody target on human acute myeloid leukemia stem cells. Cell, 2009. 138(2): p. 286-99.
16. Willingham, S. B., et al., The CD47-signal regulatory protein alpha (SIRPα) interaction is a therapeutic target for human solid tumors. Proc Natl Acad Sci USA, 2012. 109(17): p. 6662-7.
17. Weiskopf, K., et al., Engineered SIRPalpha variants as immunotherapeutic adjuvants to anticancer antibodies. Science, 2013. 341(6141): p. 88-91.

Example 3: Blood Biomarker Analysis for Early Detection, Treatment Response and Disease Progression of Breast Cancer Since 90% of women diagnosed with BC at the earliest stage have a 5 year survival rate compared to about 15% for women diagnosed at the most advanced stage, there is a need for early diagnosis of BC by routine screening. In this example, we focus on discovering biomarkers using "Exosomes" for diagnosis of BC.

Exosomes, the cell secreted about 30 to about 150 nm vesicles, carry different kinds of functional molecules (proteins, lipids and nucleic acids such as mRNA, miRNA etc.), play a critical role in intercellular communication and modulation of several physiological and pathological functions including, for example, tumor progression and metastasis (2-7). Recent studies demonstrate that enrichment of glypican-1 (GPC1), a cell surface proteoglycan, on pancreatic cancer-cell-derived exosomes is correlated with the tumor burden and the survival of pre- and post-surgical patients (8). Moreover, expression of exosomal integrins dictate the organ-specific metastasis of cancer cells (9). BC cell-derived exosomes may carry specific protein molecules that can be applied into clinics for diagnosis of BC, and are related to phenotypes and status of BC. Circulating exosomes provide a promising approach to assess novel and dynamic biomarkers in human disease, due to their stability, accessibility and representation of molecules from source cells.

The purpose of this example is to analyze the exosomes secreted by the BC cells as well as normal breast epithelial cells (BECs) as well as to explore the protein molecules specifically carried out by the BC exosomes those can be utilized into clinics for the diagnosis of BC.

Methods

Isolation of Human Bone Marrow-Derived Mesenchymal Stem Cells (hMSCs)

Bone marrow is isolated. The marrow aspirate is transferred from the syringes to sterile 50 ml centrifuge tubes and add 20 ml of PBS and mix. Centrifuge suspensions at 2000 RPM for 10 minutes at 20±3° C. Aspirate supernatant and resuspend the pellets using 10 ml of PBS. Load cell suspension gently using a 10 ml pipette onto a sterile tube containing 1.073 g/ml Percoll gradient. Centrifuge at 2500 RPM (1300 g) for 30 minutes at 20±3° C. Remove top layer and cell band (approximate 5 ml volume) and transfer into a sterile 50 ml centrifuge tube. Add 25 ml of PBS, mix gently and centrifuge cell suspensions at 2500 RPM for 10 minutes at 20±3° C. Aspirate supernatant, resuspend pellets in pre-warmed complete hMSC culture medium, and incubate the cells in 175 cm$^2$ flask at 37° C. in 5% $CO_2$ incubator.

Cell Culture

Before starting cell culture, all cell lines were tested for *mycoplasma* contamination. The human breast adenocarcinoma cell lines SKBR-3, BT-474, MDA-MB-231, and MCF-7, and breast epithelial cell lines MCF-10A and MCF-12A were obtained from the American Type Culture Collection, ATCC (Manassas, Va., USA). MCF-7, MDA-MB-231, BT-474, and HEK293FT cells were cultured in Dulbecco's Modified Eagle's Medium (DMEM) supplemented with 5% (v/v) fetal bovine serum (FBS), 100 U/ml penicillin and 100 mg/ml streptomycin. SKBR-3 cells were cultured in ATCC-formulated McCoy's SA Medium supplemented with 5% (v/v) FBS and 100 U/ml penicillin and 100 mg/ml streptomycin. MCF-10A cells were cultured in Mammary Epithelium Basal Medium (MEBM) supplemented with additive kits ((MEGM, Lonza CC-3150, without no gentamicin-amphotericin B mix (GA-1000) was added)) 100 U/ml penicillin, 100 mg/ml streptomycin and 100 μg/ml cholera toxin. MCF-12A cells were cultured in a mixture of DMEM and Ham's F12 medium (1:1 v/v) with 20 μg/ml human epidermal growth factor, 100 μg/ml cholera toxin, 0.01 mg/ml bovine insulin, 500 μg/ml hydrocortisone and 5% horse serum (v/v). Human bone marrow-derived Mesenchymal Stem Cells (MSCs) were grown in low glucose containing DMEM (Gibco) supplemented with 5% (v/v) MSC Qualified Plus Cell Culture Supplement (Compass Biomedical, Cleveland, Ohio, USA), and 1% (v/v) L-Glutamine. For the preparation of all of the above complete medium; FBS, horse serum or MSC Qualified Plus Cell Culture Supplement was pre-depleted of exosomes by ultracentrifugation at 100,000×g for 16 hours at 4° C.

Isolation and Purification of Exosomes from Cells

Figures 18A, 18B, 18C, 18D:
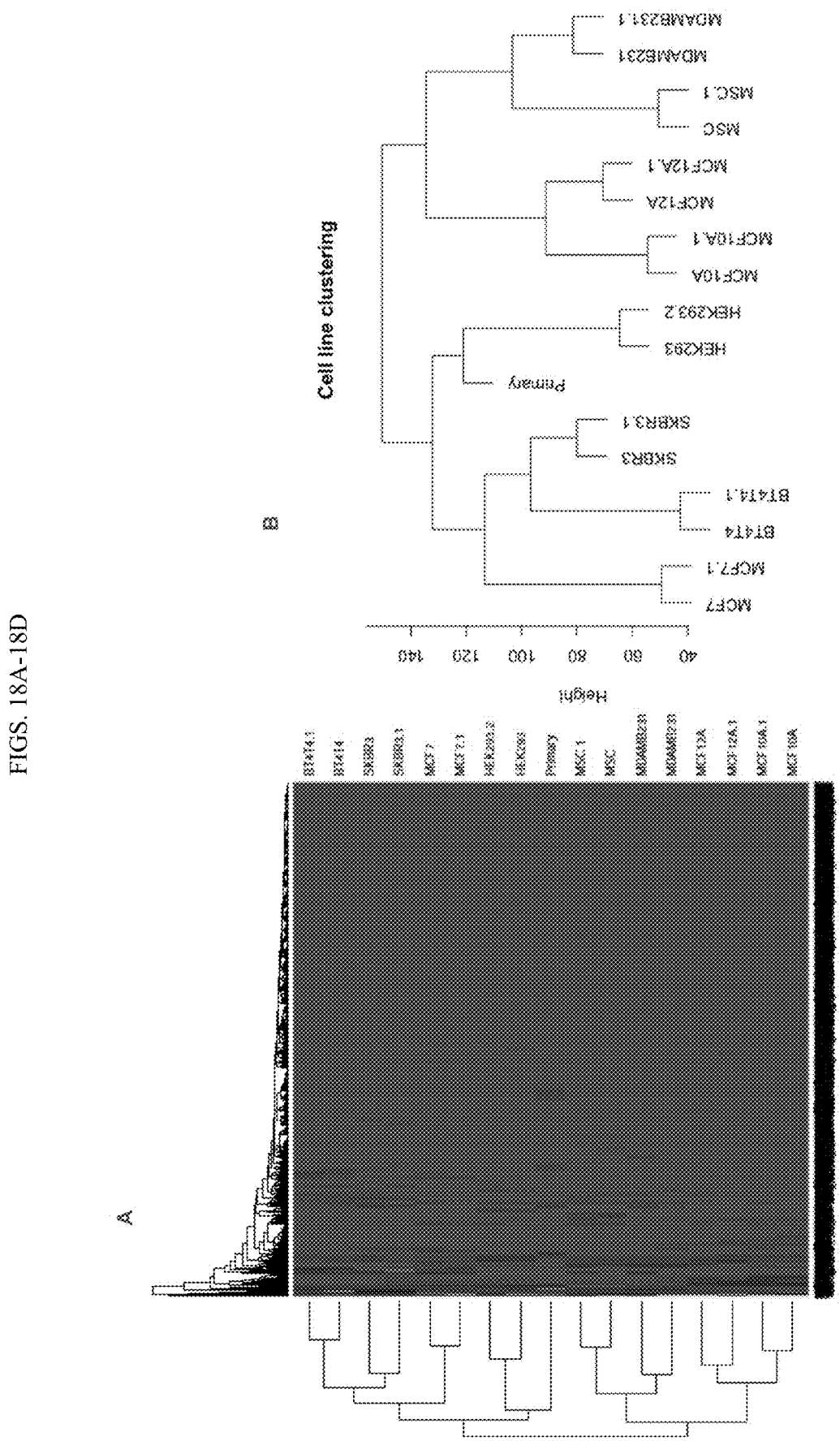
FIGS. 18A-18D show mass spec-based proteomic profiling of cancer cell-secreted exosomes versus other cell-produced exosomes. Exosomes were isolated from 9 different cell lines, and proteomics analyses of exosomes were performed. A. Heatmap analysis of exosomal proteins. B. Cell-clustering assay showing the clusters of cells of different phenotypes. C. Mass-spectrometry analysis of exosomes revealed the presence of ~1500 proteins out of which 35 proteins up-regulated in exosomes from breast cancer cells as compared to exosomes from immortalized normal cells (the list of 35 proteins is presented in FIG. 23). D. Histograms showing relative mass spec expression of HER2 in cancer exosomes from SKBR-3 (HER2+), BT-474 (HER2+), MDAMB-231 (TNBC), and MCF7 (ER+) cells compared to normal healthy exosomes from MCF-12A, MCF-10A, and MSCs. N=2 for each cell line, p=0.0003 for the signature comparison.
Figures 18A, 18B, 18C, 18D:
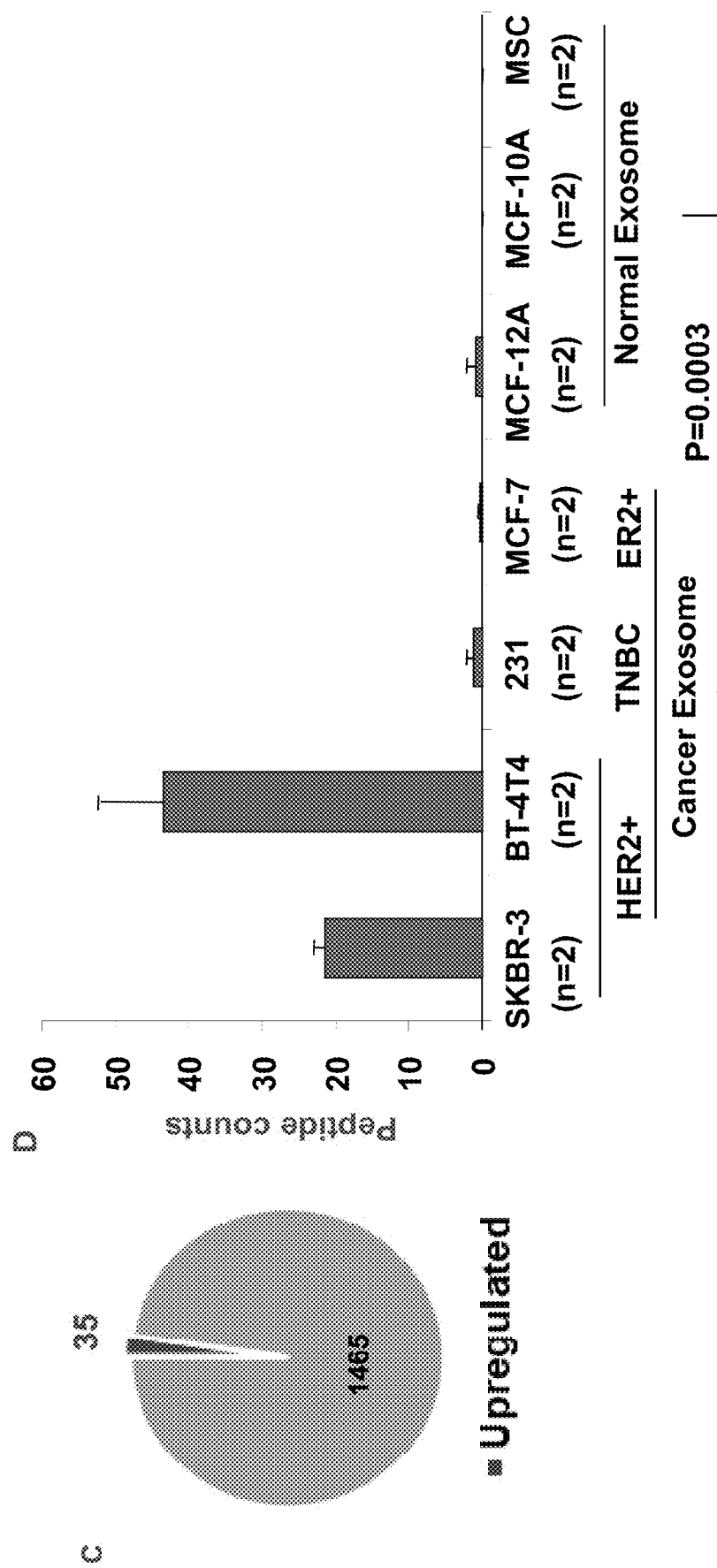

Exosomes were isolated from the cell culture supernatant, as described previously in our article (10), incorporated by reference herein. Briefly, the cultured cells monolayers were cultured as monolayers were maintained for 48 h in respective complete medium under an atmosphere of 5% $CO_2$ at 37° C. for 48 h. When the cells reached confluency of approximately 80% confluent after 48 h, exosomes were isolated by differential centrifugation. First, the culture supernatant was centrifuged at 2,000×g for 10 min followed by 30 min centrifugation at 10,000×g to remove dead cells and cell debris, respectively. The clarified supernatant was ultracentrifuged for 2 h at 100,000×g for 2 h using a SW28 rotor to pellet the exosomes. Exosomes were washed by resuspending them in with 30 ml of sterile PBS (Hyclone, Utah, USA), and then ultracentrifuged pelleted by at 100,000×g for 2 h. The final resulting exosome pellet was resuspended in 100 μl PBS and stored at −80° C. A scheme of the isolation process is represented in FIG. 18A.

FACS Analysis of Exosomes

For the detection of surface proteins, exosomes were attached on the surface of incubated and thoroughly mixed with about 3 μg of exosomal protein equivalent amounts of exosomes with and 0.1 μl of beads Aldehyde/Sulfate Latex Beads (4 μm, Thermo Fisher Scientific Inc., MA USA) by at room temperature for 1 h with and continuous mixing. The reaction is stopped by adding Glycine to block the remaining binding sites. The mixer was then diluted with PBS to 200 μl in PBS and centrifuged at 3000×g, for 5 min at 4° C. The exosome-bound beads were blocked with 10% BSA at room temperature for 30 min, and centrifuged at 3000×g for 5 min at 4° C., followed by washing with PBS, and were recentrifuged. Exosomes-bound beads were incubated with the corresponding fluorescent tagged antibodies in PBS for 20 min at 4° C. and washed twice with PBS. A final round of centrifugation was performed at 3000×g for 5 min at 4° C. Finally, the exosomes were diluted in PBS and flow cytometry analysis was performed using BD-LSR II (BD Biosciences, CA, USA). Exosome-bound beads remain untreated or treated with fluorescent tagged Isotype control IgG were used served as background controls.

Rapid Micro Flow Cytometer Analysis of Human Plasma

Plasma samples from the breast cancer patient were diluted with PBS (1:100) followed by incubation with the respective antibodies for the detection of FITC or PE labeled CD81, CD47, CD109, HER2 (BD Biosciences, San Jose, Calif., USA) for 30 min on ice. The samples were run on Apogee A50 Micro Flow Cytometer (MFC) (Apogee Flow Systems, Hertfordshire, UK), a dedicated FC specifically developed for the analysis of nanoparticles (http://www.apogeeflow.com/products.php). The above diluted plasma samples were left untreated or treated with FITC or PE labeled corresponding Mouse IgG κ Isotype Controls (BD Biosciences, San Jose, Calif., USA) for the same time and used as background controls.

Western Blot Analysis

Cells and exosomes were lysed using a lysis buffer. Protein lysates of exosomes (5 μg) were run on 4-20% Mini-PROTEIN TGX gel (Bio-Rad, Hercules, Calif., USA)

and transferred to a PVDF membrane. The blots were incubated either with a mouse monoclonal anti-human CD63 antibody (Cat # ab8219, Abcam, Cambridge, Mass., USA) at a dilution of 1:10000, or with a mouse monoclonal anti-human β-actin (Cat # ab8224, Abcam, Cambridge, Mass., USA) at a dilution of 2.5:10000 (in TBS buffer containing 2% BSA) for 1 h at room temperature. After washing with a TBS buffer, the blots were incubated with secondary antibody (horseradish peroxidase, HRP-conjugated goat anti-mouse (Cat # W402B) from Promega, Madison, Wis., USA) at a dilution of 1:10000 (2% Milk containing TBS buffer) for 1 h at room temperature. The blots were treated with the ECL kit following the user manual. Protein bands were detected on X-ray film using Konica Minolta SRX-101A Medical Film Processor (Konica Minolta Medical & Graphic Inc., Shanghai, China).

Electron Microscopy

Formvar/carbon-coated EM grids (Gilder Nickel Grid, Electron microscopy Sciences, PA, USA) were placed on Formvar/carbon side down on top of the exosome sample drops for 10 minutes at room temperature. Once the grids were removed and blotted with filter paper, they were placed onto drops of freshly prepared 2% uranyl acetate aqueous solution for one minute. The excess uranylacetate solution was removed, and then air-dried. The images of the exosomes were captured using the FEI Tecnai™ Spirit (T12) transmission electron microscope (Hillsboro, Oreg., USA) with a Gatan US4000 4k×4k charge coupled device (CCD) camera.

Size Distribution of Exosomes

The size and Zeta-potential of the exosomes were measured using ZetaView® nanoparticle tracking analyzer (Particle Metrix GmbH, Meerbusch, Germany).

Liquid Chromatography and Mass Spectrometry (LC/MS) Analysis of Exosomes

Samples were diluted 1:1 with 2% SDS followed by 30 minute incubation on ice. Aliquots were sonicated at 50% amplitude followed by vortexing; this cycle was repeated 2 times with samples sitting on ice between each round. SDS detergent removal and reduction and alkylation were performed using the Filter Assisted Sample Preparation method (FASP) as reported before (11). Total protein concentration was determined using a modified Bradford assay (Bio-Rad Laboratories), and 5 μg of protein was digested as previously described (12). LC/MS/MS was performed using a Waters ultra high-pressure liquid chromatography NanoAcquity (Waters Corporation, Milford, Mass.) and an LTQ Orbitrap Velos (ThermoFisher Scientific, Waltham, Mass.). The instrument was mass calibrated immediately before the analysis using the instrument protocol. Mobile phase A (aqueous) contained 0.1% formic acid and mobile phase B (organic) contained 0.1% formic acid. Samples were trapped and desalted on-line in mobile phase A at 10 μL/min for 10 minutes using a Waters UPLC PST C18 nanoACQUITY 300 (75 μl×25 cm) reversed phase column with 5% mobile phase B. Separation was obtained by employing a gradient of 0% to 99% mobile B at 0.300 μL/min over 120 minutes. The column was washed at 99% mobile phase B for 10 minutes, followed by a re-equilibration at 100% A for 15 minutes. Positive mode electrospray was conducted using a nanospray source and the mass spectrometer was operated at a resolution of 60,000. Quantitative and qualitative data were acquired using alternating full MS scan and MS/MS scans in normal mode. Survey data were acquired from m/z of 300 to 1800 and up to 20 precursors based on intensity were interrogated by MS/MS per switch. Two micro scans were acquired for every precursor interrogated and MS/MS was acquired as centroid data. The MS/MS peak lists were searched by Mascot (version 2.4.1, Uniprot_12_2012) (Matrix Science, London, UK). The database used was mouse Uniprot_12_2012 (20233 sequences). Search settings were as follows: trypsin enzyme specificity; mass accuracy window for precursor ion, 10 ppm; mass accuracy window for fragment ions, 0.8 Da; variable modifications including carbamidomethlylation of cysteins, 1 missed cleavage and oxidation of methoinine.

Cellular Uptake of Exosomes

For the cellular uptake study of the exosomes, 100,000 MCF-12A cells were seeded on a 35-mm glass-bottom dish for 24 h. The next day, the cells were washed with PBS and then incubated with PKH67 labeled SKBR-3 exosomes (50 μg protein equivalent amount) for 1 h at 37° C. After 50 min of incubation, Hoechst 33342 was added to stain the nuclei and the suspension reincubated for an additional 10 min. The cells were washed twice with PBS and were observed under Leica DMI6000 confocal microscope (Leica Microsystems Inc., Buffalo Grove, Ill., USA) in presence of culture media. The cells remain untreated with exosomes was used as control.

Cell Count and Transwell Cell Migration Assay

For these studies, 50,000 MCF-12A cells were seeded on a 12-well plate for 24 h. The next day, the cells were washed with PBS and then incubated with SKBR-3 exosomes (50 μg protein equivalent amount) for the next 48 h at 37° C. The same process was followed at every $3^{rd}$ day and continued for 30 days. For cell count analysis, cells were stained with Trypan blue and counted on hemocytometer at day 30. Same process of exosome treatment was followed for transwell cell migration assay. In vitro transwell cell migration assay for MCF-12A cells (control, SKBR-3 exosome treated was performed according to the migration assay reagent manufacturer's protocol.

Results

Characterization of Exosomes

Figures 22A, 22B, 22C, 22D:
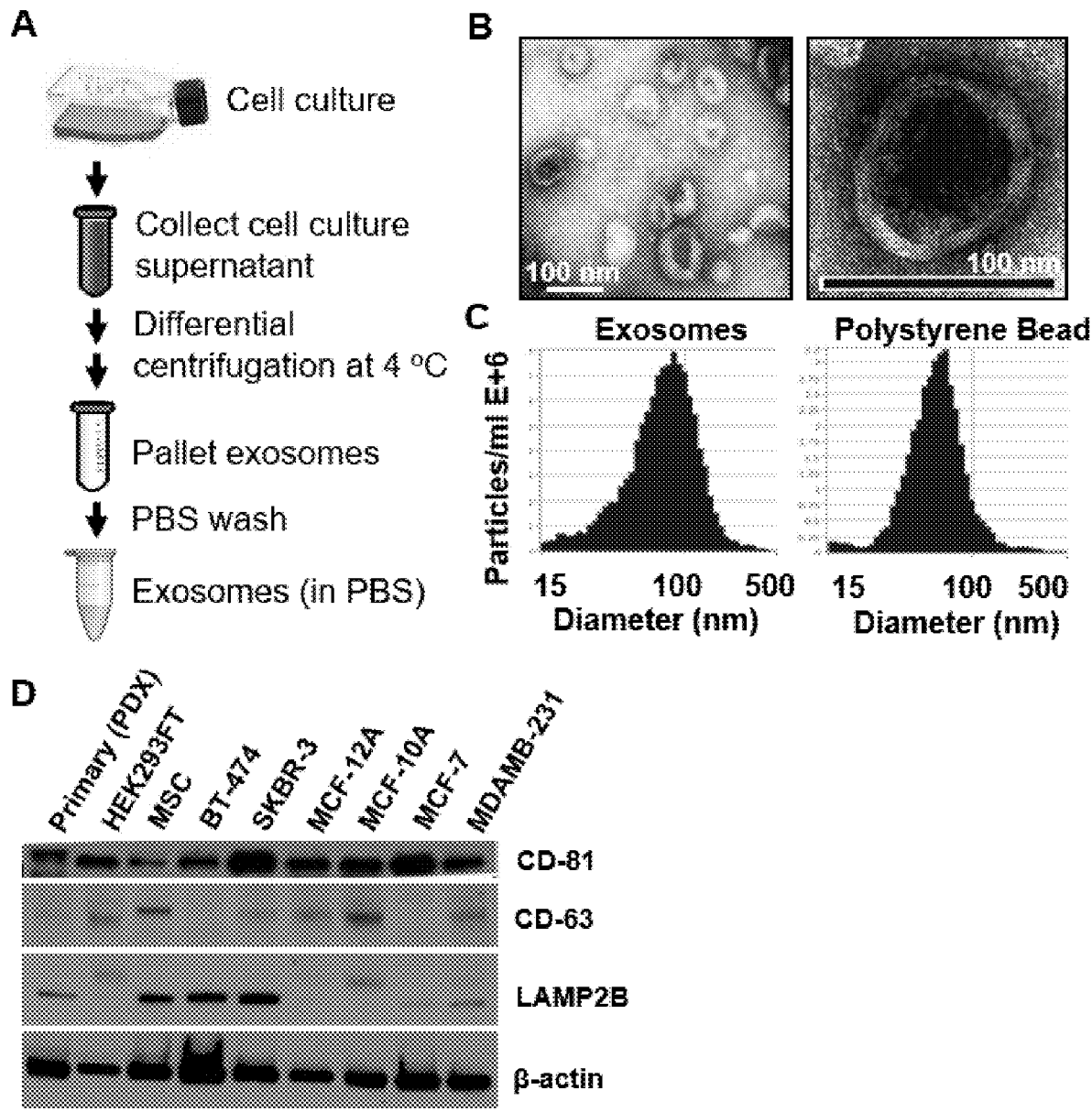
FIG. 22A-22D shows isolation and characterization of exosomes by TEM, ZetaView, and Western blots. A. Flow chart representing the isolation and purification of exosomes from the cell culture supernatant. B. Electron microscopy of exosomes secreted by MDAMB-231 cells. The size of the exosomes is ~100 nm in diameter, and are surrounded by a lipid bilayer. C. ZetaView measurement of the size distribution of MDAMB-231 exosomes and reference Polystyrene beads (60 nm). D. Expression of CD81 (~30 kDa), CD63 (~55 kDa), and LAMP2B (~50 kDa) in exosomes isolated from 9 different cell lines observed by western blotting of exosome lysates (5 µg lysates), β-actin (~42 kDa) serves as background control.

In this study, we used a differential centrifugation approach (FIG. 22A) to isolate and purify exosomes from 9 different cell lines having different phenotypes. The cell-derived exosomes were characterized based on their size, shape and the presence of exosome-specific markers. We confirmed our exosome isolation technique using transmission electron microscopy (TEM) where MDAMB-231 cell-derived exosomes measured ~100 nm in diameter where lipid bilayer was evident around the surface of exosomes, a hallmark of exosomes (FIG. 22B). Additionally, we used ZetaView nanoparticle analyzer to compare size of exosomes and the reference 60 nm polystyrene beads, finding each ranged 79+/−35 nm and 65+/−28 nm in mean diameter, respectively (FIG. 22C). Finally, we identified 3 common exosome markers, CD81 and CD63, LAMP2B, in most of the isolated exosomes by western blot analysis (FIG. 22D), indicated the presence of exosomes in the pellets observed at the end of the differential centrifugation.

MS Analysis of Exosomes

To profile the protein content of the exosomes secreted by different types of cells, we perform proteomics analyses using Mascot database system, and a heatmap analysis was performed showing the differential expression of exosomal proteins (FIG. 18A). The non-supervised clustering of proteomic data on exosomes revealed that the normal breast epithelial cells (MCF-10A, MCF-12A) derived exosomes are clustered together (FIG. 18B), so do the HER2+ cells (SKBR-3, BT-474) derived exosomes have clustered/grouped profiling. The linkage of MDAMB-231 cells derived exosomes to MSC exosomes might indicate the stem-like feature of MDAMB-231 cells derived exosomes. This study revealed the presence of about 1500 different types of proteins differentially expressed in the isolated exosomes (FIG. 18C). Based on 2-fit change FDR<0.05, we found 35 proteins exclusively up-regulated in the exosomes derived from the breast cancer (BC) cells (MCF-7, MDA-MB-231, BT-474, SKBR-3) as compared to the normal breast epithelial cells (BECs) (MCF-10A, MCF-12A) (FIG. 23). Among the above 35 proteins, the HER2 expression was found specifically up-regulated in exosomes secreted by the HER2+BC cells (FIG. 18D), indicating the possibility of its specific expression on HER2+BC cell-secreted exosomes.

Figures 19A, 19B, 19C, 19D, 19E:
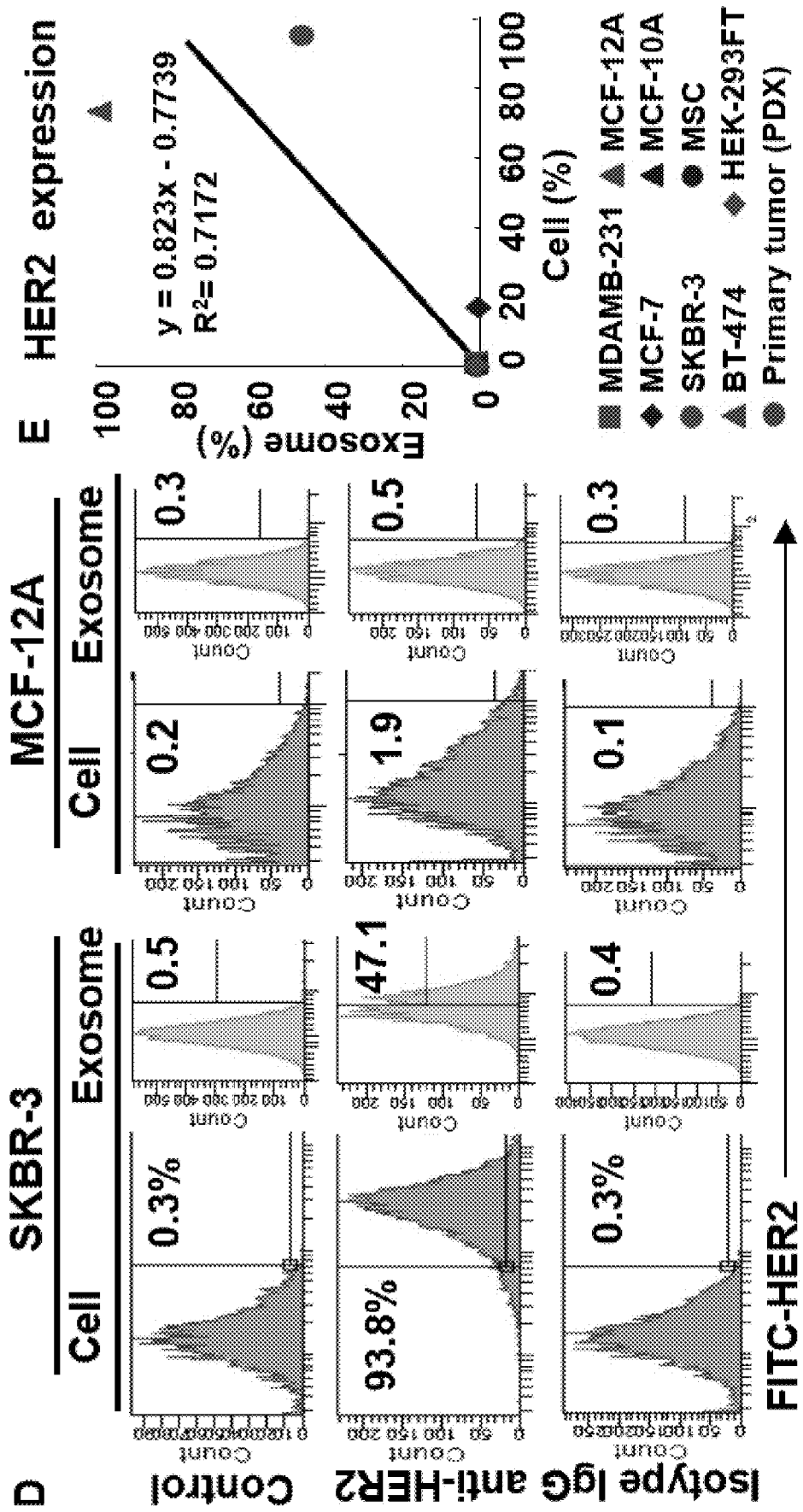
FIGS. 19A-19E shows evaluation of the expression of exosomal/cellular surface proteins by flow cytometry (FC). A. Bead-assisted flow cytometry. A diagram showing the process of (1) exosomes binding to 4 μm latex bead, (2) blocking of the bead/exosome complex with BSA, and (3) recognition of surface proteins with specific antibodies. B. TEM of bead and MDAMB-231 exosome conjugated bead representing the successful conjugation exosome around the surface of the beads as evidenced by the lipid bilayer of exosomes. C. Bead assisted FC detection of CD63 on the surface of MDAMB-231 exosomes. D. Expression of HER2 on SKBR-3 cell and its exosomes as compared to MCF-12A, detected by FC. E. Correlation of HER2 expression observed on various cells and their secreted exosomes, detected by FC and MFC respectively. P<0.0001.

Expression of HER2 on Cells and Cell-Secreted Exosomes, and it's Specificity to Cancer Exosome For this analysis, exosomes were conjugated to the surface of the latex beads (4 µm), as illustrated in FIG. 19A, and the conjugation was confirmed by the presence of exosome bilayer observed around the surface of the bead (FIG. 19B). We then validated exosome detection using this bead-assisted flow cytometry approach by identifying expression of the exosome marker, CD63, in MDA-MB-231 cell-derived exosomes by incubating the exosome-bead conjugation with FITC-anti hCD63 (FIG. 19C). Similarly, for the detection of HER2, the cells and cell-secreted exosomes were incubated with FITC-anti hHER2 and analyzed for evaluating the expression of HER2 by regular flow cytometry (BD-LSR-II). Compared to other tested cell lines, the expression of HER2 was found only in SKBR-3 and BT-474 cells and their secreted exosomes (FIG. 1D).

Correlation Study on her-2 Expression by Cells and Cell-Secreted Exosomes

We further analyzed the flow cytometry data in order to observe the correlation between the expression of Her-2 on the cell lines and their corresponding exosomes. After statistical analysis, $R^2$ values greater than 0.30 were selected as significant. Her-2/ErbB2 positive BC cell lines, SKBR-3 and BT-474 predictably showed high levels of Her2 expression on both their corresponding cells and exosomes. A good correlation ($R^2$=0.7, $p<0.0001$) was observed in the expression of Her2 on the cell and exosome surface (FIG. 19E).

Detection of Circulating Breast Cancer Biomarkers Using Human Plasma

Figure 20:
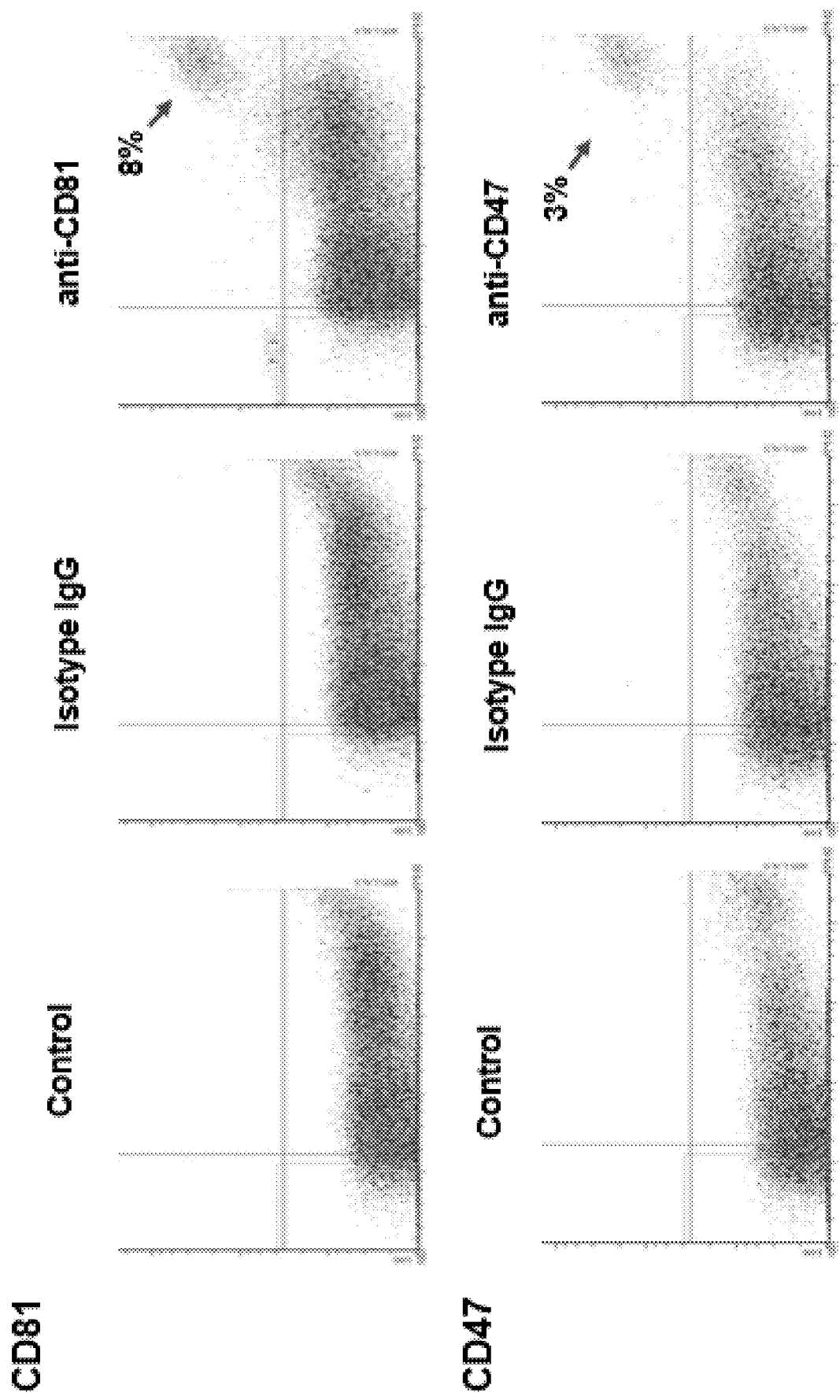
FIG. 20 shows detection of circulating EV/exosome surface markers using plasma from human breast cancer patients. Apogee A50 Micro Flow Cytometer (MFC) analyses demonstrates the detection of the expression of exosome specific marker CD81 and cancer specific markers CD47, CD109, HER2 in the crude plasma of human breast cancer patients in the absence of the tedious exosome purification procedure.
Figure 20:
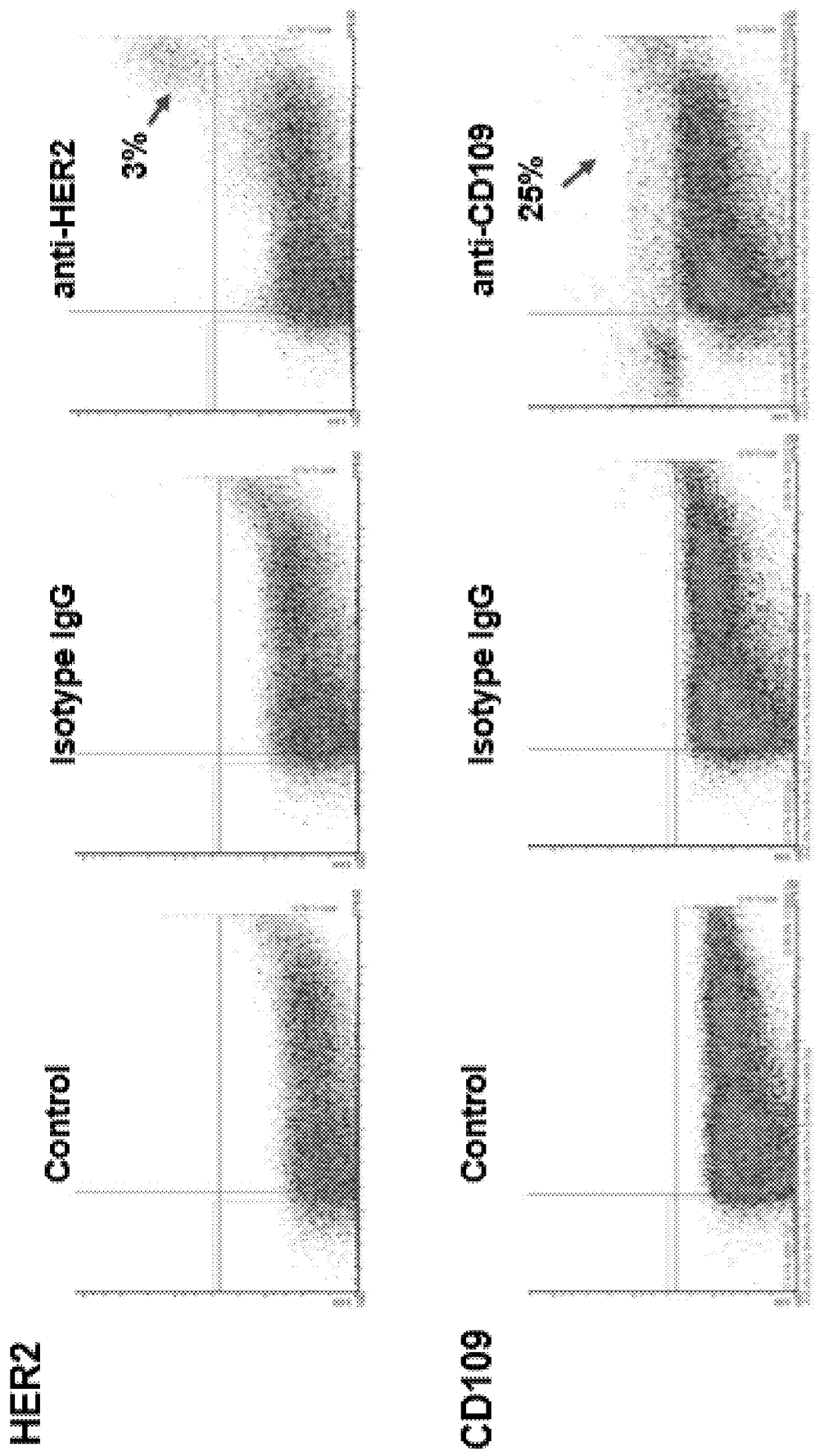

For the detection of circulating breast cancer biomarkers using plasma from breast cancer patient, plasma samples were diluted with PBS and treated with the antibodies for the detection of CD81, CD47, CD109, HER2 by Apogee A50 Micro Flow Cytometer (MFC). The expression of exosome specific marker CD81 was detected on the plasma samples as observed by MFC analyses (FIG. 20). Furthermore, the MFC analyses demonstrated the presence of cancer specific markers CD47, CD109, HER2 in the plasma (FIG. 20), indicating the suitability and detection of cancer biomarkers directly using the plasma from human breast cancer patients by advance MFC technology.

Role of Cancer Exosome on Phenotypic Changes of Normal Breast Epithelial Cells

Cancer cells and tumor microenvironment (TME) are known to communicate or "cross talk" with each other through several mediators including exosomes (EVs) (13-15). In TME, cancer cell secreted exosomes transfer their content to other cell types, thereby modifying, for example, immune responses, cell growth, angiogenesis and metastasis (16). In the breast TME, the BC exosomes may be taken up by the BECs that may lead the phenotypic changes and the expression of certain molecules in the recipient cells, as postulated in the FIG. 21A. The purpose of this study is to evaluate the role of cancer exosomes on the phenotypic changes and functional properties of BECs as well as the identification of protein molecules in BC exosomes responsible for the changes of BECs.

Figures 21A, 21B, 21C, 21D, 21E, 21F, 21G, 21H, 21I, 21J:
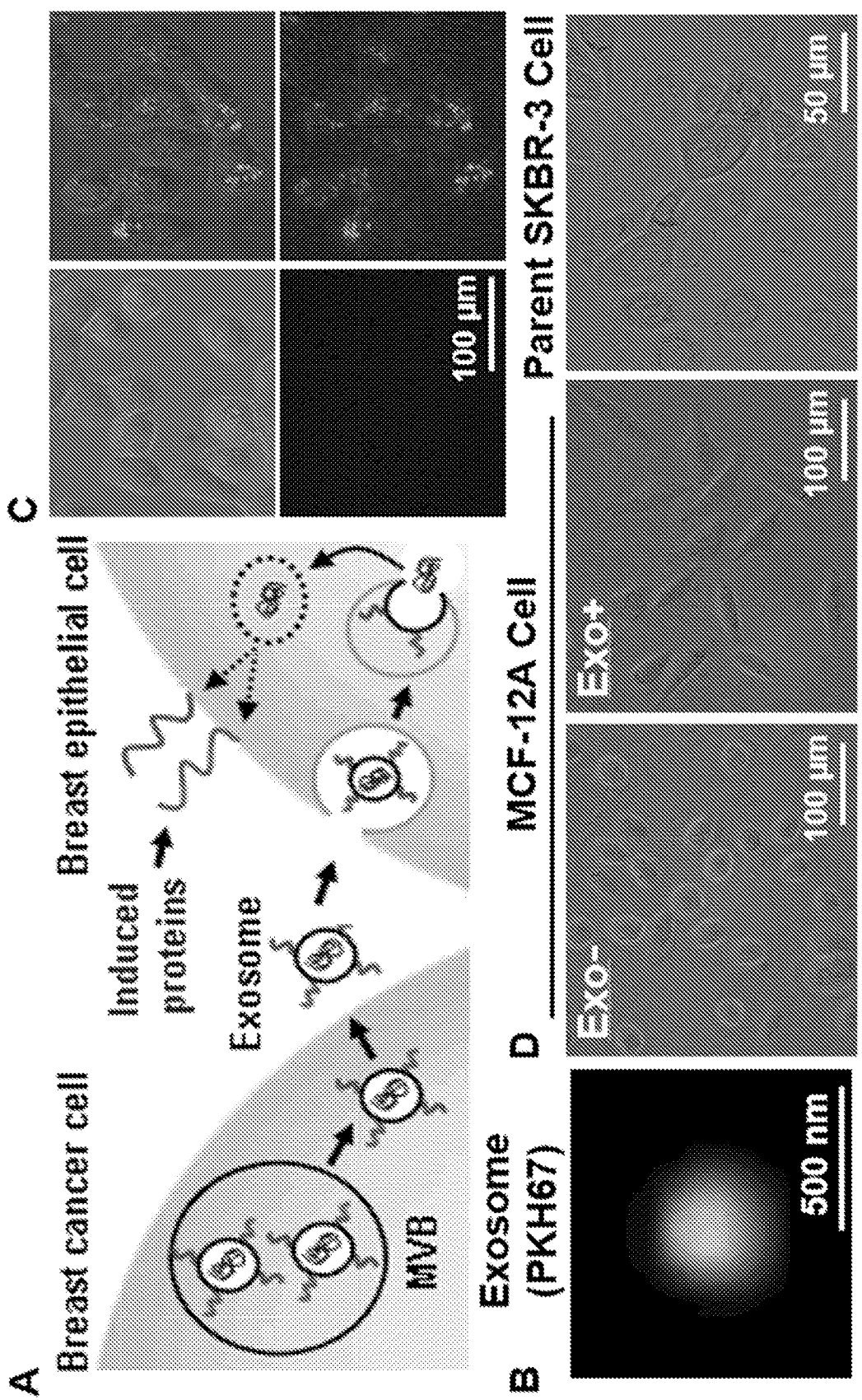
FIGS. 21A-21J show the effect of breast cancer (BC) exosomes on normal breast epithelial cells (BECs). A. Schematic representation of the BC exosome-mediated delivery of genetic materials/signals and subsequent induction of protein molecules in the recipient MCF-12A cells. B-C. Internalization of PKH67 labeled (green) SKBR-3 exosomes (B) to MCF-12A cells (C). D. Phenotypic changes of MCF-12A cells induced by the SKBR-3 exosomes. E-F. Induction of cell growth and migration of MCF-12A cells by SKBR-3 exosomes. Qualitative and quantitative immunoblot (G-H) and Mass-spec (I) analyses using the lysates of MCF12A cells (SKBR-3 exosome treated or untreated) determine the expression of CD44, HER2, F-actin, Vimentin etc. in MCF-12A cells treated with SKBR-3 exosomes as compared to the untreated cells (the list shown in FIG. 23). J. Pathway analysis using MetaCore from Thomson Reuters (version 6.32) identifies five pathways significantly enriched in MCF-12A cells treated with BC exosomes, compared to untreated cells.
Figures 21A, 21B, 21C, 21D, 21E, 21F, 21G, 21H, 21I, 21J:
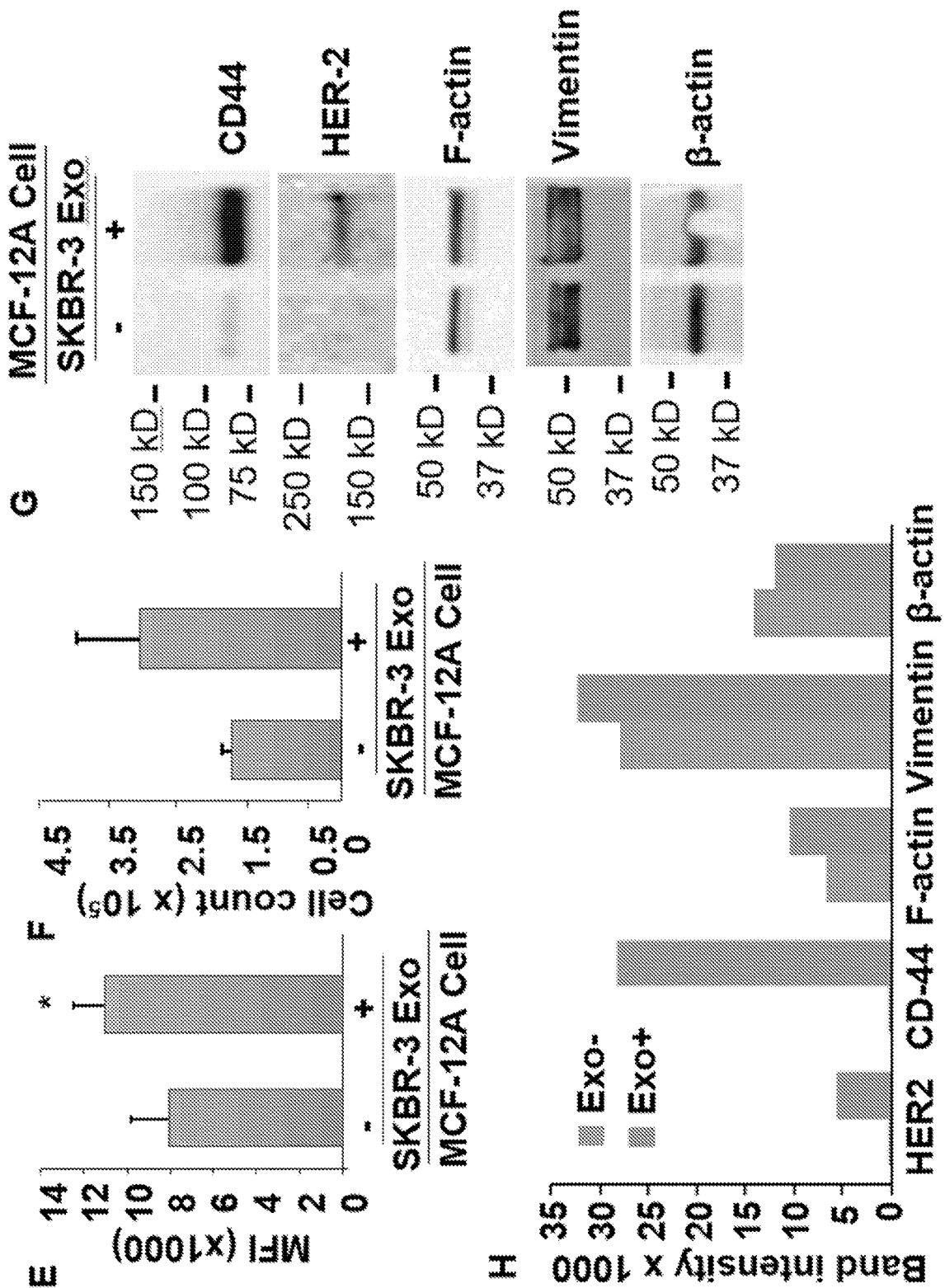
Figures 21A, 21B, 21C, 21D, 21E, 21F, 21G, 21H, 21I, 21J:
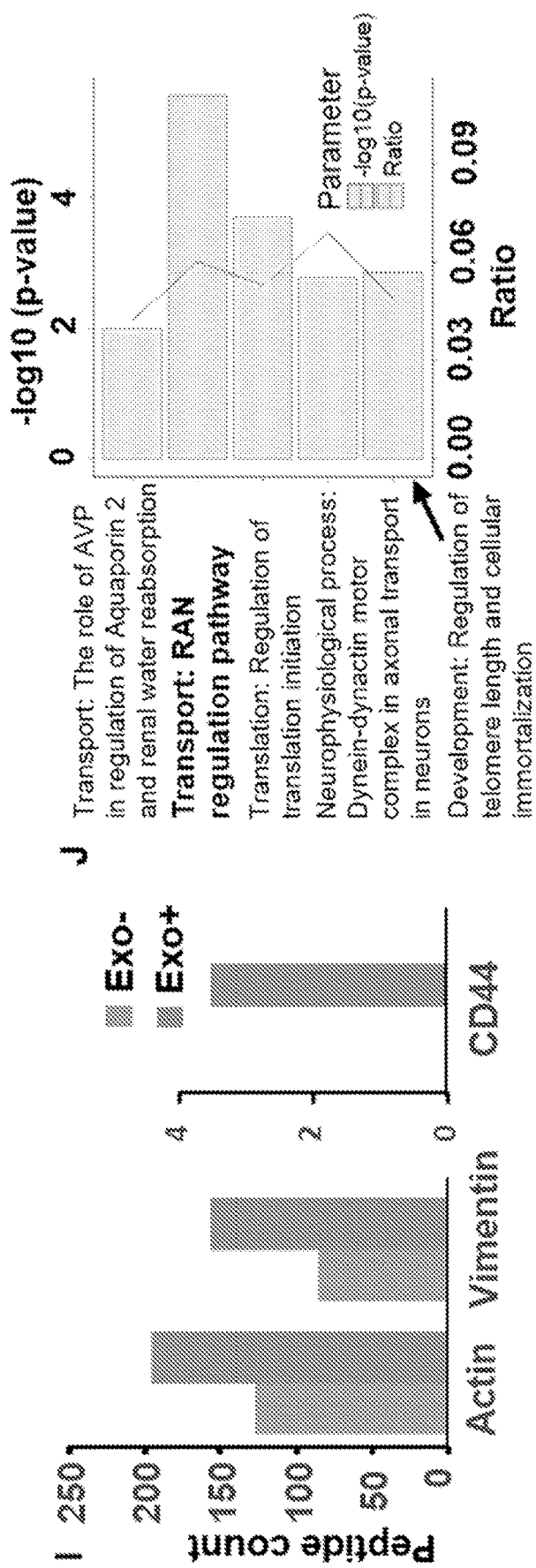

Intracellular Delivery of Breast Cancer Exosomes to Normal Breast Epithelial Cells The SKBR-3 cell (HER2+, metastatic to lung) derived exosomes were labeled with PKH67 (green) lipid marker (FIG. 21B) followed by incubation of MCF-12A cells with the labeled-exosomes for 1 h at 37° C., where the cancer exosomes were found readily taken up and internalized into the MCF-12A cells (FIG. 21C). To evaluate the effect of cancer exosomes on phenotypic changes of normal cells, MCF-12A cells were treated and incubated with SKBR-3 exosomes (50 µg protein) at every $3^{rd}$ day for a month at 37° C. Exosome treatment induces the phenotypic changes of MCF-12A cells (from oval to spindle) as compared to the control (no treatment with exosomes) (FIG. 21D). Furthermore, exosomes treatment significantly increases the MCF-12A cell growth and cell migration (FIG. 21E).

Identification of Potential Protein Molecules Responsible for Phenotypic Changes of Normal Breast Epithelial Cells To explore the possible mechanism by which BC exosome induces the phenotypic changes of normal BECs, the expression of several predominating protein molecules including the epithelial to mesenchymal transition (EMT) markers β-Catenin, Vimentin, E-cadherin, F-actin as well as stemness-related markers CD44, CD47, EGFR, HER2 etc. on exosome treated MCF-12 cells were evaluated. The immunoblot and mass-spectrometry analyses using the cell lysates indicated the upregulated expression of HER2, CD44, Vimentin, F-actin in MCF-12A cells treated with BC exosomes, as compared to the untreated cells (FIGS. 21G, and 4H, quantitative data of 4G), where β-Catenin and EGFR expressions on exosome treated cells were down-regulated and no expression of CD47 was observed (data not shown). Furthermore, the proteomics analyses using the lysates of the MCF-12A cells (untreated or exosome-treated) also revealed the overexpression of Actin, Vimentin and CD44 in the exosome-treated MCF-12A cells as compared to the untreated control (FIG. 21I). Using mass-spectrometry data, pathway analysis by following MetaCore from Thomson Reuters (version 6.32) was performed identifying the top five pathways, including the pathways related to nuclear transportation of protein molecules significantly enriched in BC exosome treated MCF-12A cells (FIG. 21J). These results suggest the potential role of BC exosomes on phenotypic changes of non-malignant BECs to stem like or pre-tumorigenic cells which can be triggered by the proteins (HER2, CD44 etc.) or signals carried by the BC exosomes.

CONCLUSION

This study reveals that cancer cell-derived exosomes contain various cancer-associated surface markers. Compared to all other tested cell lines and the exosomes, the expression of HER2 was found in SKBR-3 and BT-474 cells as well as in their secreted exosomes, indicating the utilization of HER2 as potential diagnostic and screening tool to detect BC in clinics. Furthermore, this study will help to elucidate the pathophysiological functions of tumor-derived exosomes in the tumor microenvironment. Therefore, this study demonstrates that BC cell-derived exosomes may provide diagnostic information and aid in therapeutic decisions for cancer patients through a blood test.

REFERENCES FOR EXAMPLE 3

1. Anonymous (2015) Breast cancer survival statistics 2015, Cancer Research UK.
2. Valadi H, et al. (2007) Exosome-mediated transfer of mRNAs and microRNAs is a novel mechanism of genetic exchange between cells. *Nat Cell Biol* 9(6):654-659.
3. Harding C V, Heuser J E, & Stahl P D (2013) Exosomes: looking back three decades and into the future. *The Journal of cell biology* 200(4):367-371.
4. Wang Z, Gerstein M, & Snyder M (2009) RNA-Seq: a revolutionary tool for transcriptomics. *Nature reviews* 10(1):57-63.
5. McCabe M T, et al. (2012) EZH2 inhibition as a therapeutic strategy for lymphoma with EZH2-activating mutations. *Nature* 492(7427):108-112.
6. Vire E, et al. (2006) The Polycomb group protein EZH2 directly controls DNA methylation. *Nature* 439(7078): 871-874.
7. Schorey J S & Bhatnagar S (2008) Exosome function: from tumor immunology to pathogen biology. *Traffic* 9(6):871-881.
8. Melo S A, et al. (2015) Glypican-1 identifies cancer exosomes and detects early pancreatic cancer. *Nature* 523(7559):177-182.
9. Hoshino A, et al. (2015) Tumour exosome integrins determine organotropic metastasis. *Nature* 527(7578): 329-335.
10. Kibria G, et al. (2016) A rapid, automated surface protein profiling of single circulating exosomes in human blood. *Sci Rep* 6:36502.
11. Wisniewski J R, Zougman A, Nagaraj N, & Mann M (2009) Universal sample preparation method for proteome analysis. *Nat Methods* 6(5):359-362.
12. Schlatzer D M, Sugalski J, Dazard J E, Chance M R, & Anthony D D (2012) A quantitative proteomic approach for detecting protein profiles of activated human myeloid dendritic cells. *J Immunol Methods* 375(1-2):39-45.
13. Marcucci F, Bellone M, Caserta C A, & Corti A (2014) Pushing tumor cells towards a malignant phenotype: stimuli from the microenvironment, intercellular communications and alternative roads. *Int J Cancer* 135(6):1265-1276.
14. Paltridge J L, Belle L, & Khew-Goodall Y (2013) The secretome in cancer progression. *Biochim Biophys Acta* 1834(11):2233-2241.
15. Svensson K J & Belting M (2013) Role of extracellular membrane vesicles in intercellular communication of the tumour microenvironment. *Biochem Soc Trans* 41(1): 273-276.
16. Azmi A S, Bao B, & Sarkar F H (2013) Exosomes in cancer development, metastasis, and drug resistance: a comprehensive review. *Cancer Metastasis Rev* 32(3-4): 623-642.

Each publication, patent, and patent publication cited in this disclosure is incorporated in reference herein in its entirety. The present invention is not intended to be limited to the foregoing examples, but encompasses all such modifications and variations as come within the scope of the appended claims.

The invention claimed is:

1. A method of bioengineering exosomes for targeting cancer cells, the method comprising:
   (a) expressing a XPepα fusion protein encoded by SEQ ID NO:2 in a host cell;
   (b) isolating secreted exosomes comprising the fusion protein; and
   (c) loading the isolated exosomes with a least one RNA oligonucleotide or chemotherapeutic agent.

2. The method of claim 1, wherein step (a) comprises transducing the host cell with a viral vector encoding the fusion protein.

3. A bioengineered exosome made by the method of claim 1.

4. A therapeutic bioengineered exosome comprising a XPepα fusion protein encoded by SEQ ID NO:2.

5. The therapeutic bioengineered exosome of claim 4 further comprising at least one RNA oligonucleotide or chemotherapeutic agent.

6. The therapeutic bioengineered exosome of claim 5, wherein the RNA oligonucleotide is a siRNA or miRNA specific for cancer.

7. The therapeutic bioengineered exosome of claim 6, wherein the cancer is breast cancer and wherein the miRNA is miR-200, miR30c, or miR206.

8. A method of treating a patient with cancer, the method comprising administering an effective amount of the therapeutic bioengineered exosome of claim 5 to the patient with cancer.

9. The method of claim 8, wherein the patient has a solid tumor cancer.

10. The method of claim 1, wherein step (c) comprises loading the at least one RNA oligonucleotide or chemotherapeutic agent by electroporation of the exosomes.

11. The method of claim 1, wherein the RNA oligonucleotide is a siRNA or miRNA specific for breast cancer.

12. The method of claim 8, wherein the cancer is breast cancer and wherein the at least one RNA oligonucleotide is a miRNA selected from the group consisting of miR-200, miR30c, and miR206.

* * * * *

SEQUENCE LISTING

```
<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: synthetic

<400> SEQUENCE: 1
acaagtttgt acaaaaaagc aggct                                            25

<210> SEQ ID NO 2
<211> LENGTH: 606
<212> TYPE: DNA
<213> ORGANISM: Artificial Sequence
<220> FEATURE:
<223> OTHER INFORMATION: synthetic - fusion protein

<400> SEQUENCE: 2
accatggtgt gcttccgcct cttccggtt ccgggctcag ggctcgttct ggtctgccta        60
gtcctgggag ctgtgcggtc ttatgcagga ggtggcagtg gaggtggcag tgaggaggag      120
ctgcagatta ttcagcctga caagtccgtg ttggttgcag ctggagagac agccactctg      180
cgctgcacta ttacctctct gtttcctgtg gggcccatcc agtggttcag aggagctgga      240
ccaggccggg ttttaatcta caatcaacgc caaggccctt ccccccgggt aacaactgtt      300
tcagacacta caaagagaaa caacatggac ttttccatcc gcatcggtaa catcaccca      360 gcagatgccg gcacctacta ctgtattaag ttccggaaag ggagccccga tgacgtggag      420
tttaagtctg gagcaggcac tgagctgtct gtgcgcgcca aaccctctgc ccccggaggt      480
```

| | |
|---|---|
| agtggcggag gtagtggcct aatcccaatt atagttggtg ctggtctttc aggcttgatt | 540 |
| atcgttatag tgattgctta cgtaattggc agaagaaaaa gttatgctgg atatcagact | 600 |
| ctgtaa | 606 |

<210> SEQ ID NO 3
<211> LENGTH: 25
<212> TYPE: DNA
<213> ORGANISM: Artificial Sequence
<220> FEATURE:
<223> OTHER INFORMATION: synthetic

<400> SEQUENCE: 3

| | |
|---|---|
| acccagcttt cttgtacaaa gtggt | 25 |

<210> SEQ ID NO 4
<211> LENGTH: 3150
<212> TYPE: DNA
<213> ORGANISM: Artificial Sequence
<220> FEATURE:
<223> OTHER INFORMATION: synthetic

<400> SEQUENCE: 4

| | |
|---|---|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt cccagtcac gacgttgtaa | 540 |
| aacgacggcc agtcttaagc tcgggcccca ataatgatt tattttgac tgatagtgac | 600 |
| ctgttcgttg caacacattg atgagcaatg ctttttata tgccaactt tgtacaaaaa | 660 |
| agcaggctac catggtgtgc ttccgcctct tcccggttcc gggctcaggg ctcgttctgg | 720 |
| tctgcctagt cctgggagct gtgcggtctt atgcaggagg tggcagtgga ggtggcagtg | 780 |
| aggaggagct gcagattatt cagcctgaca gtccgtgtt ggttgcagct ggagagacag | 840 |
| ccactctgcg ctgcactatt acctctctgt tcctgtggg gcccatccag tggttcagag | 900 |
| gagctggacc aggccgggtt ttaatctaca atcaacgcca aggccctttc cccgggtaa | 960 |
| caactgtttc agacactaca aagagaaaca acatggactt ttccatccgc atcggtaaca | 1020 |
| tcaccccagc agatgccggc acctactact gtattaagtt ccggaaaggg agcccgatg | 1080 |
| acgtggagtt taagtctgga gcaggcactg agctgtctgt gcgcgccaaa ccctctgccc | 1140 |
| ccggaggtag tggcggaggt agtggcctaa tcccaattat agttggtgct ggtctttcag | 1200 |
| gcttgattat cgttatagtg attgcttacg taattggcag aagaaaagt tatgctggat | 1260 |
| atcagactct gtaaacccag cttcttgta caagttggc attataagaa agcattgctt | 1320 |
| atcaatttgt tgcaacgaac aggtcactat cagtcaaaat aaaatcatta tttgccatcc | 1380 |
| agctgatatc ccctatagtg agtcgtatta catggtcata gctgtttcct ggcagctctg | 1440 |
| gcccgtgtct caaaatctct gatgttacat tgcacaagat aaaataatat catcatgaac | 1500 |
| aataaaactg tctgcttaca taaacagtaa tacaaggggt gttatgagcc atattcaacg | 1560 |

```
ggaaacgtcg aggccgcgat taaattccaa catggatgct gatttatatg ggtataaatg    1620
ggctcgcgat aatgtcgggc aatcaggtgc gacaatctat cgcttgtatg ggaagcccga    1680
tgcgccagag ttgtttctga acatggcaa aggtagcgtt gccaatgatg ttacagatga    1740
gatggtcaga ctaaactggc tgacggaatt tatgcctctt ccgaccatca agcattttat    1800
ccgtactcct gatgatgcat ggttactcac cactgcgatc cccggaaaaa cagcattcca    1860
ggtattagaa gaatatcctg attcaggtga aatattgtt gatgcgctgg cagtgttcct    1920
gcgccggttg cattcgattc ctgtttgtaa ttgtccttt aacagcgatc gcgtatttcg    1980
tctcgctcag gcgcaatcac gaatgaataa cggtttggtt gatgcgagtg attttgatga    2040
cgagcgtaat ggctggcctg ttgaacaagt ctggaaagaa atgcataaac ttttgccatt    2100
ctcaccggat tcagtcgtca ctcatggtga tttctcactt gataaccttat ttttgacga    2160 ggggaaatta ataggttgta ttgatgttgg acgagtcgga atcgcagacc gataccagga    2220
tcttgccatc ctatggaact gcctcggtga gttttctcct tcattacaga aacggctttt    2280
tcaaaaatat ggtattgata atcctgatat gaataaattg cagtttcatt tgatgctcga    2340
tgagtttttc taatcagaat tggttaattg gttgtaacac tggcagagca ttacgctgac    2400
ttgacgggac ggcgcaagct catgaccaaa atcccttaac gtgagttacg cgtcgttcca    2460
ctgagcgtca gacccgtag aaaagatcaa aggatcttct tgagatcctt ttttctgcg    2520 cgtaatctgc tgcttgcaaa caaaaaaacc accgctacca gcggtggttt gtttgccgga    2580
tcaagagcta ccaactcttt ttccgaaggt aactggcttc agcagagcgc agataccaaa    2640
tactgttctt ctagtgtagc cgtagttagg ccaccacttc aagaactctg tagcaccgcc    2700
tacatacctc gctctgctaa tcctgttacc agtggctgct gccagtggcg ataagtcgtg    2760
tcttaccggg ttggactcaa gacgatagtt accggataag gcgcagcggt cgggctgaac    2820
ggggggttcg tgcacacagc ccagcttgga gcgaacgacc tacaccgaac tgagatacct    2880
acagcgtgag ctatgagaaa gcgccacgct tcccgaaggg agaaaggcgg acaggtatcc    2940
ggtaagcggc agggtcggaa caggagagcg cacgagggag cttccagggg gaaacgcctg    3000
gtatctttat agtcctgtcg ggtttcgcca cctctgactt gagcgtcgat ttttgtgatg    3060
ctcgtcaggg gggcggagcc tatggaaaaa cgccagcaac gcggcctttt tacggttcct    3120
ggccttttgc tggccttttg ctcacatgtt                                    3150

<210> SEQ ID NO 5
<211> LENGTH: 12865
<212> TYPE: DNA
<213> ORGANISM: Artificial Sequence
<220> FEATURE:
<223> OTHER INFORMATION: synthetic

<400> SEQUENCE: 5
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
```

```
tccattgacg tcaatgggtg gactatttac ggtaaactgc ccacttggca gtacatcaag    480
tgtatcatat gccaagtacg cccctattg acgtcaatga cggtaaatgg cccgcctggc     540
attatgccca gtacatgacc ttacgggact ttcctacttg gcagtacatc tacgtattag    600
tcatcgctat taccatggtg atgcggtttt ggcagtacac caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctctg tactgggtct ctctggttag accagatctg    840
agcctgggag ctctctggct aactagggaa cccactgctt aagcctcaat aaagcttgcc    900
ttgagtgctt caagtagtgt gtgcccgtct gttgtgtgac tctggtaact agagatccct    960 cagaccctt tagtcagtgt ggaaaatctc tagcagtggc gcccgaacag ggacttgaaa    1020
gcgaaaggga accagagga gctctctcga cgcaggactc ggcttgctga agcgcgcacg    1080
gcaagaggcg aggggcggcg actggtgagt acgccaaaaa ttttgactag cggaggctag    1140
aaggagagag atgggtgcga gagcgtcagt attaagcggg ggagaattag atcgcgatgg    1200
gaaaaaattc ggttaaggcc agggggaaag aaaaaatata aattaaaaca tatagtatgg    1260
gcaagcaggg agctagaacg attcgcagtt aatcctggcc tgttagaaac atcagaaggc    1320
tgtagacaaa tactgggaca gctacaacca tcccttcaga caggatcaga gaacttaga    1380 tcattatata atacagtagc aaccctctat tgtgtgcatc aaaggataga gataaaagac    1440
accaaggaag ctttagacaa gatagaggaa gagcaaaaca aaagtaagac caccgcacag    1500
caagcggccg ctgatcttca gacctggagg aggagatatg agggacaatt ggagaagtga    1560
attatataaa tataaagtag taaaaattga accattagga gtagcaccca ccaaggcaaa    1620
gagaagagtg gtgcagagag aaaaaagagc agtgggaata ggagctttgt tccttgggtt    1680
cttgggagca gcaggaagca ctatgggcgc agcgtcaatg acgctgacgg tacaggccag    1740
acaattattg tctggtatag tgcagcagca gaacaatttg ctgagggcta ttgaggcgca    1800
acagcatctg ttgcaactca cagtctgggg catcaagcag ctccaggcaa gaatcctggc    1860
tgtggaaaga tacctaaagg atcaacagct cctggggatt tggggttgct ctggaaaact    1920
catttgcacc actgctgtgc cttggaatgc tagttggagt aataaatctc tggaacagat    1980
ttggaatcac acgacctgga tggagtggga cagagaaatt aacaattaca caagcttaat    2040
acactcctta attgaagaat cgcaaaacca gcaagaaaag aatgaacaag aattattgga    2100
attagataaa tgggcaagtt tgtggaattg gtttaacata acaaattggc tgtggtatat    2160
aaaattattc ataatgatag taggaggctt ggtaggttta agaatagttt ttgctgtact    2220
ttctatagtg aatagagtta ggcagggata ttcaccatta tcgtttcaga cccacctccc    2280
aaccccgagg ggacccgaca ggcccgaagg aatagaagaa gaaggtggag agagagacag    2340
agacagatcc attcgattag tgaacggatc ggcactgcgt gcgccaattc tgcagacaaa    2400
tggcagtatt catccacaat tttaaaagaa aggggggat tggggggtac agtgcagggg    2460
aaagaatagt agaaataata gcaacagaca tacaaactaa agaattacaa aaacaaatta    2520
caaaaattca aaattttcgg gtttattaca gggacagcag agatccagtt tggttaatta    2580 accgtgtcg gctccagatc tggcctccgc gccgggtttt ggcgcctccc gcgggcgccc     2640
ccctcctcac ggcgagcgct gccacgtcag acgaagggcg cagcgagcgt cctgatcctt    2700
ccgcccggac gctcaggaca gcggcccgct gctcataaga ctcggcctta gaaccccagt    2760
atcagcagaa ggacatttta ggacgggact tgggtgactc tagggcactg gttttctttc    2820
```

```
cagagagcgg aacaggcgag gaaaagtagt cccttctcgg cgattctgcg gagggatctc   2880
cgtggggcgg tgaacgccga tgattatata aggacgcgcc gggtgtggca cagctagttc   2940
cgtcgcagcc gggatttggg tcgcggttct tgtttgtgga tcgctgtgat cgtcacttgg   3000
tgagtagcgg gctgctgggc tggccggggc tttcgtggcc gccgggccgc tcggtgggac   3060
ggaagcgtgt ggagagaccg ccaagggctg tagtctgggt ccgcgagcaa ggttgccctg   3120
aactgggggt tgggggggagc gcacaaaatg gcggctgttc ccgagtcttg aatgaaagac   3180
gcttgtgagg cgggctgtga ggtcgttgaa acaaggtggg gggcatggtg ggcggcaaga   3240
acccaaggtc ttgaggcctt cgctaatgcg ggaaagctct tattcgggtg agatgggctg   3300
gggcaccatc tggggacccc tgacgtgaag tttgtcactg actggagaaa ctcgggtttg   3360
tcgtctgttg cggggcggc agttatggcg gtgccgttgg gcagtgcacc cgtacctttg   3420
ggagcgcgcg ccctcgtcgt gtcgtgacgt cacccgttct gttggcttat aatgcagggt   3480
ggggccacct gccggtaggt gtgcggtagg cttttctccg tcgcaggacg cagggttcgg   3540
gcctagggta ggctctcctg aatcgacagg cgccggacct ctggtgaggg gagggataag   3600
tgaggcgtca gtttctttgg tcggttttat gtacctatct tcttaagtag ctgaagctcc   3660
ggttttgaac tatgcgctcg gggttggcga gtgtgtttg tgaagttttt taggcacctt   3720
ttgaaatgta atcatttggg tcaatatgta attttcagtg ttagactagt aaattgtccg   3780
ctaaattctg gccgtttttg gctttttgt tagacgaagc ttgggctgca ggtcgactct   3840
agagcggccc cgaattatca caagtttgta caaaaaagca ggctaccatg gtgtgcttcc   3900
gcctcttccc ggttccgggc tcagggctcg ttctggtctg cctagtcctg ggagctgtgc   3960
ggtcttatgc aggaggtggc agtggaggtg gcagtgagga ggagctgcag attattcagc   4020
ctgacaagtc cgtgttggtt gcagctggag agacagccac tctgcgctgc actattacct   4080
ctctgtttcc tgtggggccc atccagtggt tcagaggagc tggaccaggc cgggttttaa   4140
tctacaatca acgccaaggc cctttccccc gggtaacaac tgtttcagac actacaaaga   4200
gaaacaacat ggacttttcc atccgcatcg gtaacatcac cccagcagat gccggcacct   4260
actactgtat taagttccgg aaagggagcc ccgatgacgt ggagtttaag tctggagcag   4320
gcactgagct gtctgtgcgc gccaaaccct ctgccccgg aggtagtggc ggaggtagtg   4380
gcctaatccc aattatagtt ggtgctggtc tttcaggctt gattatcgtt atagtgattg   4440
cttacgtaat tggcagaaga aaaagttatg ctggatatca gactctgtaa acccagcttt   4500
cttgtacaaa gtggtgatcg cgttctaccg ggtaggggag gcgcttttcc caaggcagtc   4560
tggagcatgc gctttagcag ccccgctggg cacttggcgc tacacaagtg gcctctggcc   4620
tcgcacacat tccacatcca ccggtaggcg ccaaccggct ccgttctttg gtggcccctt   4680
cgcgccacct tctactcctc ccctagtcag gaagttcccc ccgccccgc agctcgcgtc   4740 gtgcaggacg tgacaaatgg aagtagcacg tctcactagt ctcgtgcaga tggacagcac   4800
cgctgagcaa tggaagcggg taggcctttg gggcagcggc caatagcagc tttgctcctt   4860
cgctttctgg gctcagaggc tgggaagggg tgggtccggg ggcgggctca ggggcgggct   4920 cagggcggg gcgggcgccc gaaggtcctc cggaggcccg gcattctgca cgcttcaaaa   4980
gcgcacgtct gccgcgctgt tctcctcttc ctcatctccg ggcctttcga cctgcagccc   5040
aagcttactc tagaggatca aacttaagct tggcaatccg gtactgttgg taaagccacc   5100
atggaagatg ccaaaaacat taagaagggc ccagcgccat tctacccact cgaagacggg   5160
```

```
accgccggcg agcagctgca caaagccatg aagcgctacg ccctggtgcc cggcaccatc    5220
gcctttaccg acgcacatat cgaggtggac attacctacg ccgagtactt cgagatgagc    5280
gttcggctgg cagaagctat gaagcgctat gggctgaata caaaccatcg gatcgtggtg    5340
tgcagcgaga atagcttgca gttcttcatg cccgtgttgg gtgccctgtt catcggtgtg    5400
gctgtggccc cagctaacga catctacaac gagcgcgagc tgctgaacag catgggcatc    5460
agccagccca ccgtcgtatt cgtgagcaag aaagggctgc aaaagatcct caacgtgcaa    5520
aagaagctac cgatcataca aaagatcatc atcatggata gcaagaccga ctaccagggc    5580
ttccaaagca tgtacacctt cgtgacttcc catttgccac ccggcttcaa cgagtacgac    5640 tcgtgcccg agagcttcga ccgggacaaa accatcgccc tgatcatgaa cagtagtggc    5700
agtaccggat tgcccaaggg cgtagcccta ccgcaccgca ccgcttgtgt ccgattcagt    5760
catgcccgcg accccatctt cggcaaccag atcatccccg acaccgctat cctcagcgtg    5820
gtgccatttc accacggctt cggcatgttc accacgctgg gctacttgat ctgcggcttt    5880
cgggtcgtgc tcatgtaccg cttcgaggag gagctattct tgcgcagctt gcaagactat    5940
aagattcaat ctgccctgct ggtgcccaca ctatttagct tcttcgctaa gagcactctc    6000
atcgacaagt acgacctaag caacttgcac gagatcgcca gcggcggggc gccgctcagc    6060
aaggaggtag gtgaggccgt ggccaaacgc ttccacctac caggcatccg ccagggctac    6120
ggcctgacag aaacaaccag cgccattctg atcaccccg aaggggacga caagcctggc    6180
gcagtaggca aggtggtgcc cttcttcgag gctaaggtgg tggacttgga caccggtaag    6240
acactgggtg tgaaccagcg cggcgagctg tgcgtccgtg gccccatgat catgagcggc    6300
tacgttaaca ccccgaggc tacaaacgct ctcatcgaca aggacggctg gctgcacagc    6360
ggcgacatcg cctactggga cgaggacgag cacttcttca tcgtggaccg gctgaagagc    6420
ctgatcaaat acaagggcta ccaggtagcc ccagccgaac tggagagcat cctgctgcaa    6480
caccccaaca tcttcgacgc cggggtcgcc ggcctgcccg acgacgatgc cggcgagctg    6540
cccgccgcag tcgtcgtgct ggaacacggt aaaaccatga ccgagaagga gatcgtggac    6600
tatgtggcca gccaggttac aaccgccaag aagctgcgcg gtggtgttgt gttcgtggac    6660
gaggtgccta aaggactgac cggcaagttg gacgcccgca agatccgcga gattctcatt    6720
aaggccaaga agggcggcaa gatcgccgtg cctctgctg cctctgccat ggtgagcaag    6780
ggcgaggagc tgttcaccgg ggtggtgccc atcctggtcg agctggacgg cgacgtaaac    6840
ggccacaagt tcagcgtgtc cggcgagggc gagggcgatg ccacctacgg caagctgacc    6900
ctgaagttca tctgcaccac cggcaagctg cccgtgccct ggcccaccct cgtgaccacc    6960
ctgacctacg gcgtgcagtg cttcagccgc taccccgacc acatgaagca gcacgacttc    7020
ttcaagtccg ccatgcccga aggctacgtc caggagcgca ccatcttctt caaggacgac    7080
ggcaactaca agacccgcgc cgaggtgaag ttcgagggcg acaccctggt gaaccgcatc    7140
gagctgaagg gcatcgactt caaggaggac ggcaacatcc tggggcacaa gctggagtac    7200
aactacaaca gccacaacgt ctatatcatg gccgacaagc agaagaacgg catcaaggtg    7260
aacttcaaga tccgccacaa catcgaggac ggcagcgtgc agctcgccga ccactaccag    7320
cagaacaccc ccatcggcga cggccccgtg ctgctgcccg acaaccacta cctgagcacc    7380
cagtccgccc tgagcaaaga ccccaacgag aagcgcgatc acatggtcct gctggagttc    7440
gtgaccgccg ccgggatcac tctcggcatg gacgagctgt acaagtaaag cggccgcgac    7500
gctagagggc ccgtttaatt cgatatcaag cttatcgata atcaacctct ggattacaaa    7560
```

```
atttgtgaaa gattgactgg tattcttaac tatgttgctc cttttacgct atgtggatac   7620
gctgctttaa tgcctttgta tcatgctatt gcttcccgta tggctttcat tttctcctcc   7680
ttgtataaat cctggttgct gtctctttat gaggagttgt ggcccgttgt caggcaacgt   7740
ggcgtggtgt gcactgtgtt tgctgacgca accccactg gttggggcat tgccaccacc    7800
tgtcagctcc tttccgggac tttcgctttc ccctcccta ttgccacggc ggaactcatc    7860
gcccgcctgc cttgcccgct gctggacagg ggctcggctg ttgggcactg acaattccgt   7920
ggtgttgtcg gggaaatcat cgtcctttcc ttggctgctc gcctgtgttg ccacctggat   7980
tctgcgcggg acgtccttct gctacgtcct tcggccctca atccaagcgg accttccttc   8040
ccgcggcctg ctgccggctc tgcgggcctc ttccgcgtct ttcgccttcg ccctcagacg   8100
agtcggatct cccctttggg gctccccgca tcgatgtcga cctcgagacc ggccgaactc   8160
gaagacctag aaaaaacatt ggagcaatca caagtagcaa tacagcagct accaatgctg   8220
attgtgcctg gctagaagca caagaggagg aggaggtggg ttttccagtc acacctcagg   8280 taccctttaag accaatgact tacaaggcag ctgtagatct tagccacttt ttaaaagaaa   8340 agggggact ggaagggcta attcactccc aacgaagaca agatatcctt gatctgtgga    8400
tctaccacac acaaggctac ttccctgatt ggcagaacta cacaccaggg ccagggatca   8460
gatatccact gacctttgga tggtgctaca agctagtacc agttgagcaa gagaaggtag   8520
aagaagccaa tgaaggagag aacacccgct tgttacaccc tgtgagcctg catgggatgg   8580
atgacccgga gagagaagta ttagagtgga ggtttgacag ccgcctagca tttcatcaca   8640
tggcccgaga gctgcatccg gactgtactg gtctctctg gttagaccag atctgagcct    8700
gggagctctc tggctaacta gggaacccac tgcttaagcc tcaataaagc ttgccttgag   8760
tgcttcaagt agtgtgtgcc cgtctgttgt gtgactctgg taactagaga tccctcagac   8820 cctttagtc agtgtggaaa atctctagca gggcccgttt aaacccgctg atcagcctcg    8880
actgtgcctt ctagttgcca gccatctgtt gtttgcccct cccccgtgcc ttccttgacc   8940
ctggaaggtg ccactcccac tgtcctttcc taataaaatg aggaaattgc atcgcattgt   9000
ctgagtaggt gtcattctat tctggggggt ggggtggggc aggacagcaa gggggaggat   9060
tgggaagaca atagcaggca tgctgggat gcggtgggct ctatggcttc tgaggcggaa     9120
agaaccagct ggggctctag ggggtatccc cacgcgccct gtagcggcgc attaagcgcg   9180
gcgggtgtgg tggttacgcg cagcgtgacc gctacacttg ccagcgccct agcgcccgct   9240 ccttttcgctt tcttcccttc ctttctcgcc acgttcgccg gctttccccg tcaagctcta   9300
aatcggggca tccctttagg gttccgattt agtgctttac ggcacctcga ccccaaaaaa   9360
cttgattagg gtgatggttc acgtagtggg ccatcgccct gatagacggt ttttcgccct   9420
ttgacgttgg agtccacgtt ctttaatagt ggactcttgt tccaaactgg aacaacactc   9480
aaccctatct cggtctattc ttttgattta agggattt tggggatttc ggcctattgg     9540
ttaaaaaatg agctgattta acaaaaattt aacgcgaatt aattctgtgg aatgtgtgtc   9600 agttaggggtg tggaaagtcc ccaggctccc cagcaggcag aagtatgcaa agcatgcatc   9660
tcaattagtc agcaaccagg tgtggaaagt ccccaggctc cccagcaggc agaagtatgc   9720
aaagcatgca tctcaattag tcagcaacca tagtcccgcc cctaactccg cccatcccgc   9780
ccctaactcc gcccagttcc gcccattctc cgccccatgg ctgactaatt ttttttattt   9840
atgcagaggc cgaggccgcc tcggcctctg agctattcca gaagtagtga ggaggctttt   9900
```

```
ttggaggcct aggcttttgc aaaaagctcc cgggagcttg tatatccatt ttcggatctg    9960
atcagcacgt gttgacaatt aatcatcggc atagtatatc ggcatagtat aatacgacaa   10020
ggtgaggaac taaaccatgg ccaagttgac cagtgccgtt ccggtgctca ccgcgcgcga   10080
cgtcgccgga gcggtcgagt tctgaccgac ccggctcggg ttctcccggg acttcgtgga   10140
ggacgacttc gccggtgtgg tccgggacga cgtgaccctg ttcatcagcg cggtccagga   10200
ccaggtggtg ccggacaaca ccctggcctg ggtgtgggtg cgcggcctgg acgagctgta   10260
cgccgagtgg tcggaggtcg tgtccacgaa cttccgggac gcctccgggc cggccatgac   10320
cgagatcggc gagcagccgt gggggcggga gttcgccctg cgcgacccgg ccggcaactg   10380
cgtgcacttc gtggccgagg agcaggactg acacgtgcta cgagatttcg attccaccgc   10440
cgccttctat gaaaggttgg gcttcggaat cgttttccgg gacgccggct ggatgatcct   10500
ccagcgcggg gatctcatgc tggagttctt cgcccacccc aacttgttta ttgcagctta   10560
taatggttac aaataaagca atagcatcac aaatttcaca aataaagcat ttttttcact   10620
gcattctagt tgtggtttgt ccaaactcat caatgtatct tatcatgtct gtataccgtc   10680
gacctctagc tagagcttgg cgtaatcatg gtcatagctg tttcctgtgt gaaattgtta   10740
tccgctcaca attccacaca acatacgagc cggaagcata aagtgtaaag cctggggtgc   10800
ctaatgagtg agctaactca cattaattgc gttgcgctca ctgcccgctt tccagtcggg   10860
aaacctgtcg tgccagctgc attaatgaat cggccaacgc gcggggagag gcggtttgcg   10920
tattgggcgc tcttccgctt cctcgctcac tgactcgctg cgctcggtcg ttcggctgcg   10980
gcgagcggta tcagctcact caaaggcggt aatacggtta tccacagaat cagggggataa   11040 cgcaggaaag aacatgtgag caaaaggcca gcaaaaggcc aggaaccgta aaaaggccgc   11100
gttgctggcg ttttttccata ggctccgccc ccctgacgag catcacaaaa atcgacgctc   11160
aagtcagagg tggcgaaacc cgacaggact ataaagatac caggcgtttc ccctggaag   11220 ctccctcgtg cgctctcctg ttccgaccct gccgcttacc ggatacctgt ccgcctttct   11280
cccttcggga agcgtggcgc tttctcaatg ctcacgctgt aggtatctca gttcggtgta   11340
ggtcgttcgc tccaagctgg gctgtgtgca cgaaccccc gttcagcccg accgctgcgc   11400
cttatccggt aactatcgtc ttgagtccaa cccggtaaga cacgacttat cgccactggc   11460
agcagccact ggtaacagga ttagcagagc gaggtatgta ggcggtgcta cagagttctt   11520
gaagtggtgg cctaactacg gctacactag aaggacagta tttggtatct gcgctctgct   11580
gaagccagtt accttcggaa aaagagttgg tagctcttga tccggcaaac aaaccaccgc   11640
tggtagcggt ggttttttttg tttgcaagca gcagattacg cgcagaaaaa aaggatctca   11700
agaagatcct ttgatctttt ctacgggtc tgacgctcag tggaacgaaa actcacgtta   11760
agggattttg gtcatgagat tatcaaaaag gatcttcacc tagatccttt taaattaaaa   11820
atgaagtttt aaatcaatct aaagtatata tgagtaaact tggtctgaca gttaccaatg   11880
cttaatcagt gaggcaccta tctcagcgat ctgtctattt cgttcatcca tagttgcctg   11940
actccccgtc gtgtagataa ctacgatacg ggagggctta ccatctggcc ccagtgctgc   12000
aatgataccg cgagacccac gctcaccggc tccagattta tcagcaataa accagccagc   12060
cggaagggcc gagcgcagaa gtggtcctgc aactttatcc gcctccatcc agtctattaa   12120
ttgttgccgg gaagctagag taagtagttc gccagttaat agtttgcgca acgttgttgc   12180
cattgctaca ggcatcgtgg tgtcacgctc gtcgtttggt atggcttcat tcagctccgg   12240
ttcccaacga tcaaggcgag ttacatgatc ccccatgttg tgcaaaaaag cggttagctc   12300
```

```
                                                         -continued cttcggtcct ccgatcgttg tcagaagtaa gttggccgca gtgttatcac tcatggttat  12360
ggcagcactg cataattctc ttactgtcat gccatccgta agatgctttt ctgtgactgg  12420
tgagtactca accaagtcat tctgagaata gtgtatgcgg cgaccgagtt gctcttgccc  12480
ggcgtcaata cgggataata ccgcgccaca tagcagaact ttaaaagtgc tcatcattgg  12540
aaaacgttct tcggggcgaa aactctcaag gatcttaccg ctgttgagat ccagttcgat  12600
gtaacccact cgtgcaccca actgatcttc agcatctttt actttcacca gcgtttctgg  12660
gtgagcaaaa acaggaaggc aaaatgccgc aaaaaaggga ataagggcga cacggaaatg  12720
ttgaatactc atactcttcc tttttcaata ttattgaagc atttatcagg gttattgtct  12780
catgagcgga tacatatttg aatgtattta gaaaaataaa caaatagggg ttccgcgcac  12840
atttccccga aaagtgccac ctgac                                        12865
```